(12) United States Patent
Ando et al.

(10) Patent No.: US 9,405,183 B2
(45) Date of Patent: Aug. 2, 2016

(54) RADIATION IMAGE CAPTURING SYSTEM

(75) Inventors: Takanori Ando, Tokyo (JP); Chikako Tokuno, Tokyo (JP); Koji Takemura, Tokyo (JP); Akira Kurahashi, Tokyo (JP)

(73) Assignee: KONICA MINOLTA, INC., Tokyo (JP)

( * ) Notice: Subject to any disclaimer, the term of this patent is extended or adjusted under 35 U.S.C. 154(b) by 493 days.

(21) Appl. No.: 13/643,589

(22) PCT Filed: Feb. 25, 2011

(86) PCT No.: PCT/JP2011/054269
§ 371 (c)(1),
(2), (4) Date: Oct. 26, 2012

(87) PCT Pub. No.: WO2011/142157
PCT Pub. Date: Nov. 17, 2011

(65) Prior Publication Data
US 2013/0038738 A1 Feb. 14, 2013

(30) Foreign Application Priority Data

May 12, 2010 (JP) ................................. 2010-109818
Jul. 2, 2010 (JP) ................................. 2010-151525

(51) Int. Cl.
*A61B 6/00* (2006.01)
*G03B 42/02* (2006.01)
(Continued)

(52) U.S. Cl.
CPC .............. *G03B 42/02* (2013.01); *A61B 6/4233* (2013.01); *A61B 6/4266* (2013.01);
(Continued)

(58) Field of Classification Search
CPC ....... H04N 5/30; H04N 5/35; H04B 17/0042; H04B 17/005; H04B 17/0057; H04B 17/009; H04W 16/18; A61B 6/4233; A61B 6/4266; A61B 6/4283; A61B 6/4405; A61B 6/4494; A61B 6/463; A61B 6/464; A61B 6/465; A61B 6/488; A61B 6/5294; A61B 6/542; A61B 6/545; A61B 6/548; A61B 6/563; A61B 6/585; A61B 6/587; A61B 6/4291; A61B 6/46; G03B 42/02; G03B 42/025; G03B 42/04; G06F 19/3481

USPC .................. 378/64, 98.8, 115, 116, 174, 186; 348/162, E05.085

See application file for complete search history.

(56) References Cited

U.S. PATENT DOCUMENTS 7,426,261 B2 * 9/2008 Spahn .................. A61B 6/4283
250/363.08
8,172,461 B2 * 5/2012 Liu ...................... A61B 6/4283
378/114

(Continued)

FOREIGN PATENT DOCUMENTS

JP 6-342099 A 12/1994
JP 9-73144 A 3/1997

(Continued)

OTHER PUBLICATIONS

Japanese Decision of Refusal corresponding to Application No. 2012-514731; Date of Mailing: Jul. 7, 2015, with English translation.

(Continued)

*Primary Examiner* — Thomas R Artman
(74) *Attorney, Agent, or Firm* — Cantor Colburn LLP

(57) ABSTRACT

According to one implementation of the present invention, there is provided a radiation image capturing system. The system includes, a radiation source; a plurality of radiation image capturing devices; and a console. The console manages which of the radiation image capturing devices is in a state where image capturing is possible. The console registers image capturing order information including information of which radiation image capturing device is used in the image capturing, or obtains the registered image capturing order information. When there is a radiation image capturing device in a state where image capturing is possible, regardless of a predetermined order, the console displays the icon corresponding to the image capturing order information including information of the radiation image capturing device in a manner different from the other icons.

13 Claims, 33 Drawing Sheets

(51) Int. Cl.
   *G03B 42/04* (2006.01)
   *G06F 19/00* (2011.01)

(52) U.S. Cl.
   CPC ............ *A61B 6/4283* (2013.01); *A61B 6/4291* (2013.01); *A61B 6/4405* (2013.01); *A61B 6/4494* (2013.01); *A61B 6/463* (2013.01); *A61B 6/464* (2013.01); *A61B 6/465* (2013.01); *A61B 6/488* (2013.01); *A61B 6/5294* (2013.01); *A61B 6/542* (2013.01); *A61B 6/545* (2013.01); *A61B 6/548* (2013.01); *A61B 6/563* (2013.01); *A61B 6/585* (2013.01); *A61B 6/587* (2013.01); *G03B 42/025* (2013.01); *G03B 42/04* (2013.01); *G06F 19/3481* (2013.01)

(56) References Cited

U.S. PATENT DOCUMENTS

| | | | | |
|---|---|---|---|---|
| 8,295,439 | B2* | 10/2012 | Yonekawa | A61B 6/00 378/115 |
| 8,644,454 | B2* | 2/2014 | Yonekawa | A61B 6/00 378/115 |
| 8,848,872 | B2* | 9/2014 | Lee | A61B 6/4494 250/370.09 |
| 9,072,484 | B2* | 7/2015 | Yonekawa | A61B 6/00 |
| 9,186,118 | B2* | 11/2015 | Yonekawa | A61B 6/4233 |
| 9,289,182 | B2* | 3/2016 | Yonekawa | A61B 6/465 |
| 2006/0188071 | A1* | 8/2006 | Spahn | 378/196 |
| 2009/0189761 | A1* | 7/2009 | Nishino et al. | 340/540 |
| 2009/0279764 | A1* | 11/2009 | Kaji et al. | 382/132 |
| 2011/0026676 | A1* | 2/2011 | Takekoshi | A61B 6/06 378/98.2 |
| 2011/0110494 | A1* | 5/2011 | Lee | 378/98 |
| 2013/0038738 | A1* | 2/2013 | Ando | A61B 6/4266 348/162 |

FOREIGN PATENT DOCUMENTS

| | | | | |
|---|---|---|---|---|
| JP | 2000-166908 | A | | 6/2000 |
| JP | 2000-308630 | A | | 11/2000 |
| JP | 2002-272719 | A | | 9/2002 |
| JP | 2003290200 | A | | 10/2003 |
| JP | 2006-58124 | A | | 3/2006 |
| JP | 2007007243 | A | | 1/2007 |
| JP | 2008-142314 | A | | 6/2008 |
| JP | 2008142314 | | * 6/2008 | ............... A61B 6/00 |
| JP | 2010-110433 | A | | 5/2010 |
| JP | 2010110433 | | * 5/2010 | ............... A61B 6/00 |

OTHER PUBLICATIONS

Japanese Notification of Refusal corresponding to Application No. 2012-514731; Date of Dispatch: Jan. 6, 2015, with English translation.

International Search Report for International Application No. PCT/JP2011/054269, dated May 24, 2011, with English translation.

International Preliminary Report on Patentability for International Application No. PCT/JP2011/054269, issued Dec. 10, 2012, with English translation.

* cited by examiner

FIG.13

| CAPTURING ORDER ID | PATIENT ID | PATIENT NAME | SEX | AGE | DEPARTMENT | CAPTURING PORTION | CAPTURING DIRECTION | BUCKY ID |
|---|---|---|---|---|---|---|---|---|
| 001 | 100085 | A | MALE | 25 | ORTHOPEDICS DEPARTMENT | ABDOMEN REGION | FRONT FACE P→A | 002 |
| 002 | 100085 | A | MALE | 25 | ORTHOPEDICS DEPARTMENT | CHEST REGION | FRONT FACE P→A | 001 |
| 003 | 100085 | A | MALE | 25 | ORTHOPEDICS DEPARTMENT | CERVICAL VERTEBRA | FRONT FACE P→A | 001 |
| 004 | 100085 | A | MALE | 25 | ORTHOPEDICS DEPARTMENT | BRACHIAL REGION | L | 003 |
| 005 | 100101 | B | MALE | 45 | SURGICAL DEPARTMENT | CHEST REGION | SIDE FACE R→L | 001 |
| 006 | 100063 | C | FEMALE | 32 | SURGICAL DEPARTMENT | ABDOMEN REGION | FRONT FACE A→P | 002 |

PLEASE INPUT IMAGE CAPTURING ORDER INFORMATION OF CAPTURING TO BE PERFORMED

| CAPTURING ORDER ID | PATIENT ID | PATIENT NAME | SEX | AGE | DEPARTMENT | CAPTURING PORTION | CAPTURING DIRECTION | BUCKY ID |
|---|---|---|---|---|---|---|---|---|
| 001 | 100085 | A | MALE | 25 | ORTHOPEDICS DEPARTMENT | ABDOMEN REGION | FRONT FACE P → A | 002 |
| 002 | 100085 | A | MALE | 25 | ORTHOPEDICS DEPARTMENT | CHEST REGION | FRONT FACE P → A | 001 |
| 003 | 100085 | A | MALE | 25 | ORTHOPEDICS DEPARTMENT | CERVICAL VERTEBRA | FRONT FACE P → A | 001 |
| 004 | 100085 | A | MALE | 25 | ORTHOPEDICS DEPARTMENT | BRACHIAL REGION | L | 003 |
| 005 | 100101 | B | MALE | 45 | SURGICAL DEPARTMENT | CHEST REGION | SIDE FACE R → L | 001 |
| 006 | 100063 | C | FEMALE | 32 | SURGICAL DEPARTMENT | ABDOMEN REGION | FRONT FACE A → P | 002 |

RETURN    ENTER

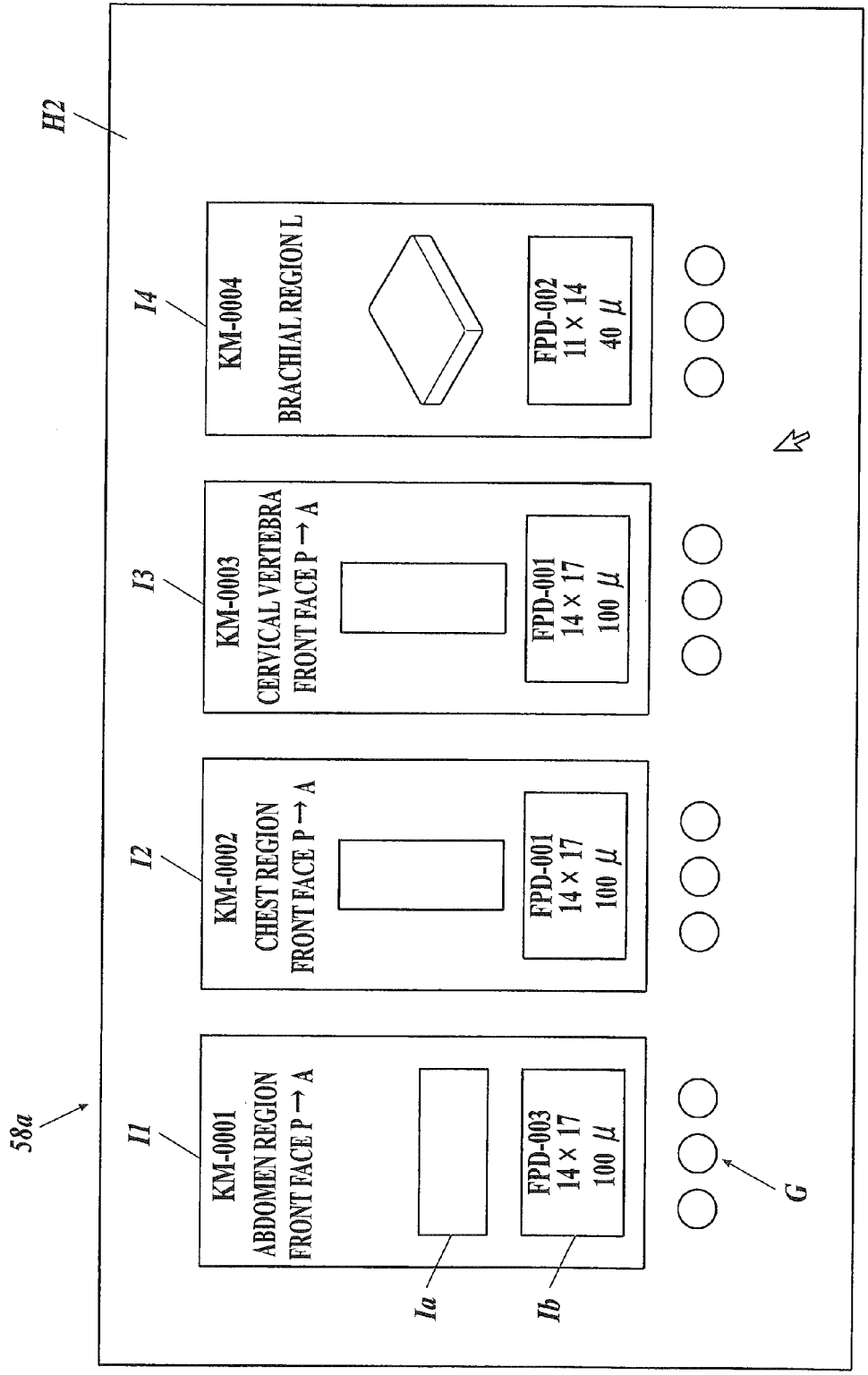

FIG.29

| CAPTURING PORTION | | CAPTURING CONDITION |
|---|---|---|
| HEAD REGION | | FRONT FACE A → P |
| | | SIDE FACE R → L |
| | | FRONT FACE P → A |
| | | SIDE FACE L → R |
| CERVICAL VERTEBRA | | FRONT FACE A → P |
| | | SIDE FACE R → L |
| | | FRONT FACE P → A |
| | | SIDE FACE L → R |
| ARM REGION | R | |
| | L | |
| CHEST REGION | | FRONT FACE A → P |
| | | SIDE FACE R → L |
| | | FRONT FACE P → A |
| | | SIDE FACE L → R |
| ABDOMEN REGION | | FRONT FACE A → P |
| | | SIDE FACE R → L |
| | | FRONT FACE P → A |
| | | SIDE FACE L → R |
| LEG REGION | R | |
| | L | |

FIG.31

| 100085 | | |
|---|---|---|
| CAPTURING PORTION | | CAPTURING CONDITION |
| CERVICAL VERTEBRA | | FRONT FACE A → P |
| | | SIDE FACE R → L |
| | | FRONT FACE P → A |
| | | SIDE FACE L → R |
| ARM REGION | R | |
| | L | |
| CHEST REGION | | FRONT FACE A → P |
| | | SIDE FACE R → L |
| | | FRONT FACE P → A |
| | | SIDE FACE L → R |
| ABDOMEN REGION | | FRONT FACE A → P |
| | | SIDE FACE R → L |
| | | FRONT FACE P → A |
| | | SIDE FACE L → R |
| LEG REGION | R | |
| | L | |
| HEAD REGION | | FRONT FACE A → P |
| | | SIDE FACE R → L |
| | | FRONT FACE P → A |
| | | SIDE FACE L → R |

CAPTURING ROOM 1 | RADIATION TECHNOLOGIST:○○ ○○
PATIENT ID:100085 | BIRTH DATE:○○○○/○○/○○
SEX:MALE | AGE:25 YEARS AND 0 MONTHS OLD

M | PAST IMAGE | TRANSMISSION PREVIEW | | EMISSION CONDITION | IMAGE QUALITY ADJUSTMENT | READING CONDITION

○○○○/○○/○○

Bp p3  p2  p1  p4

100  200
300  1.5

SHOULD IMAGES BE TRANSMITTED IN THIS ORDER?

OK    NG

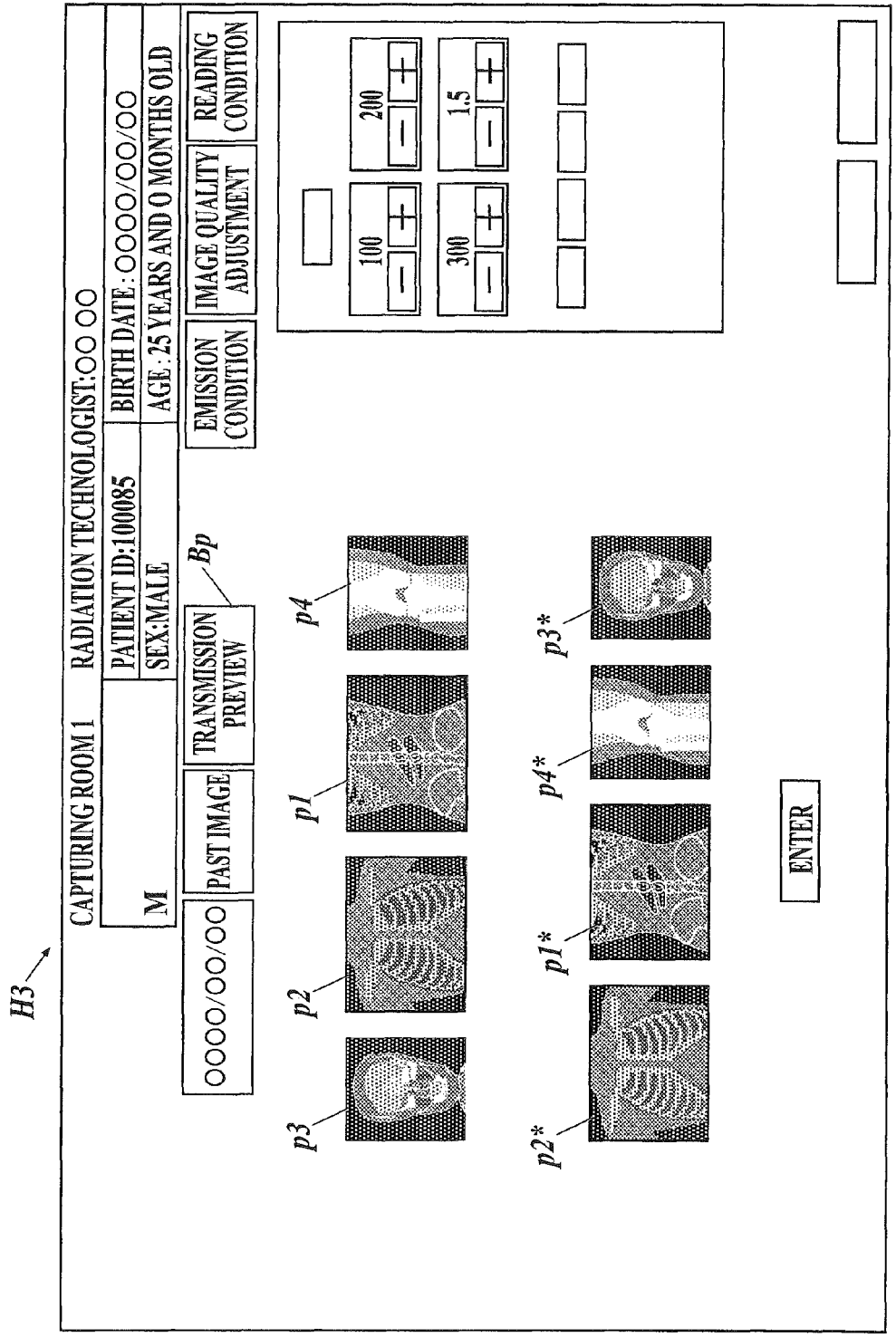

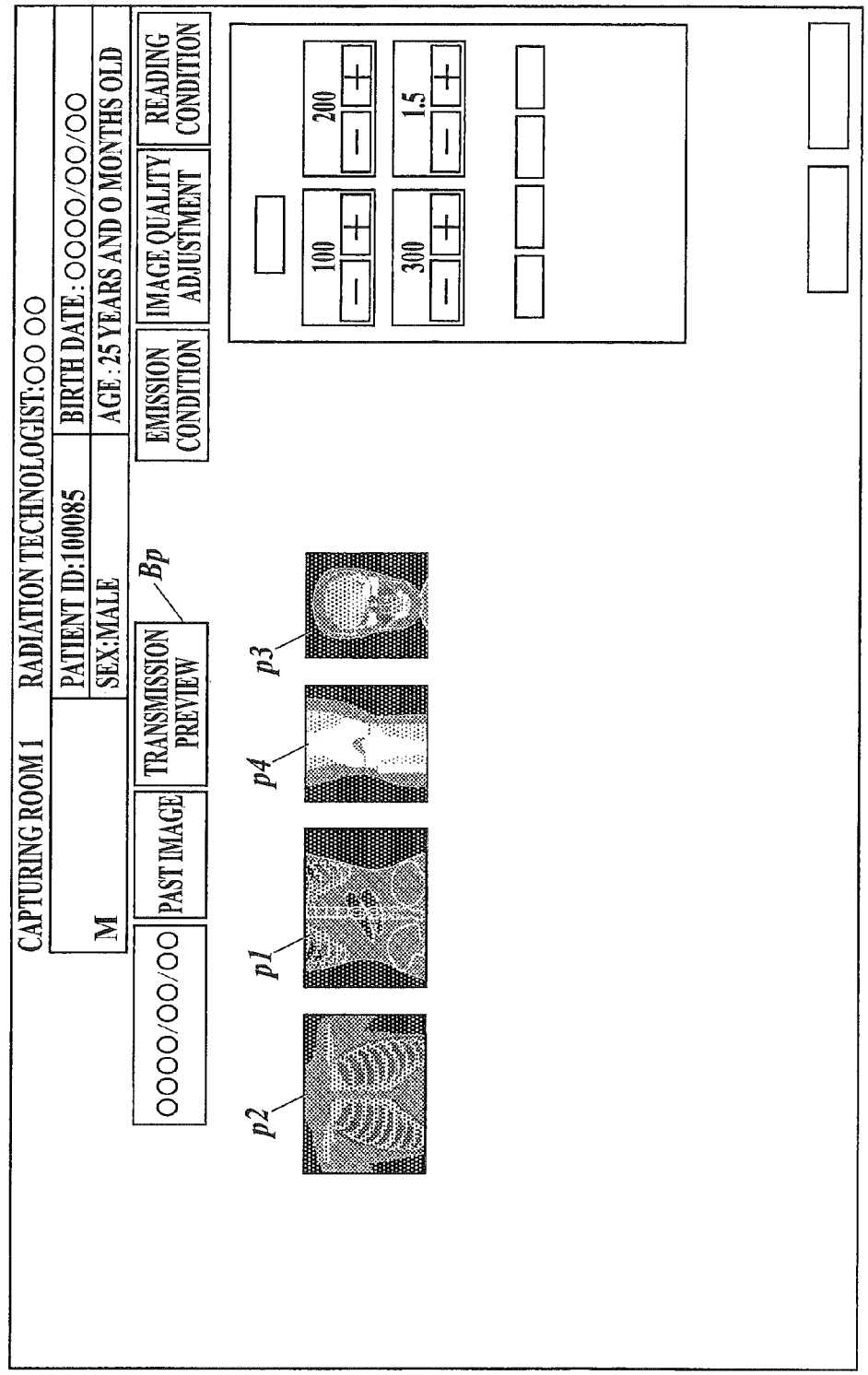

RADIATION IMAGE CAPTURING SYSTEM

CROSS REFERENCE TO RELATED APPLICATIONS

This is a U.S. national stage of application No. PCT/JP2011/054269, filed on 25 Feb. 2011. Priority under 35 U.S.C. §119(a) and 35 U.S.C. §365(b) is claimed from Japanese Application Nos. 2010-109818, filed 12 May 2010, and 2010-151525, filed 2 Jul. 2010, the disclosure of which are also incorporated herein by reference.

TECHNICAL FIELD

The present invention relates to a radiation image capturing system. Specifically, the present invention relates to a radiation image capturing system including a console to display on a display unit icons corresponding to capturing order information to be selectable with the console.

BACKGROUND ART

For the purpose of diagnosis of disease, etc., radiation image captured using radiation such as X-ray images are widely used. Conventionally, such medical radiation images are captured using screen film. However, in order to digitalize radiation images, a CR (Computed Radiography) device which uses a photostimulable phosphor sheet has been developed. Recently, a radiation image capturing device which detects the emitted radiation with a radiation detecting element and obtains the digital image data has been developed.

Such type of radiation image capturing device is known as an FPD (Flat Panel Detector). Such device can display image data more speedily than the CR device and therefore can contribute to early diagnosis. Conventionally, such device was developed as a dedicated device formed as one with a supporting stage, etc. (for example, see patent documents 1, 2). Lately, a portable radiation image capturing device in which the radiation detecting element, etc. can be stored in a housing to be transportable is developed and in practical use (for example, see patent documents 3, 4).

Various radiation image capturing devices are developed such as a direct radiation image capturing device in which charge generated in a detecting element according to the amount of emitted radiation such as X-ray is converted to an electric signal. Another is an indirect radiation image capturing device in which after the emitted radiation is converted to an electromagnetic wave of another wavelength such as a visible light with a scintillator, etc., charge is generated in a photoelectric converting element such as photodiode, etc. according to energy of the converted and emitted electromagnetic wave and converted to an electric signal. In the present invention, the detecting element in the direct radiation image capturing device and the photoelectric converting element in the indirect radiation image capturing device are collectively referred to as a radiation detecting element.

When a body, etc. of a patient is captured in a hospital or clinic using a dedicated device or a portable radiation image capturing device, a radiation image capturing system may be configured where a radiation image capturing device is provided or brought in the capturing room in the hospital or clinic and a console provided outside the capturing room is used to control the radiation image capturing device or the radiation generating device to capture the radiation image.

Such radiation image capturing system is usually configured to perform radiation image capturing based on the later described capturing order information (for example, see FIG. 13). The image capturing order information sets information, instructions, etc. regarding the radiation image capturing performed in the capturing room determined based on inquiry to the patient. For example, specified and registered are items such as patient information such as patient ID, etc., capturing conditions such as portion of body of patient to be captured and capturing direction, device information specifying device to be used.

The console may be configured to control the radiation image capturing device and the radiation generating device based on each piece of image capturing order information selected by the doctor or radiation technologist.

In the radiation image capturing system described in patent document 5, for example, it is proposed to display in a list each piece of image capturing order information regarding the patient who comes as a switch on the display unit of the console so that the radiology technologist can select any image capturing order information from the switches of each piece of image capturing order information displayed in a list in an order such as from a setting where capturing can be performed easily.

As described in patent document 5, for example, when image capturing of "cervical vertebra front face", "cervical vertebra side face", "cervical vertebra right rear oblique", "cervical vertebra open mouth" is performed on the patient, image capturing can be performed efficiently if "cervical vertebra open mouth" which is captured in a state where the patient is lying (in other words, lying position), after "cervical vertebra front face", "cervical vertebra side face", "cervical vertebra right rear oblique" which are captured in a state where the patient is standing (in other words, standing position) (or image capturing in a reverse order).

Even if the order of the image capturing order information displayed as a list on the display unit of the console is "cervical vertebra front face", "cervical vertebra open mouth", "cervical vertebra side face", "cervical vertebra right rear oblique", according to the radiation image capturing system described in Patent Document 5, for example, the order of "cervical vertebra front face"→"cervical vertebra side face"→"cervical vertebra right rear oblique" can be selected and then "cervical vertebra open mouth" can be selected. Therefore, image capturing can be performed efficiently.

PRIOR ART DOCUMENT

Patent Document

Patent Document 1: Japanese Patent No. 3890163
Patent Document 2: Japanese Unexamined Patent Application Publication No. H9-73144
Patent Document 3: Japanese Unexamined Patent Application Publication No. 2006-058124
Patent Document 4: Japanese Unexamined Patent Application Publication No. H6-342099
Patent Document 5: Japanese Unexamined Patent Application Publication No. 2000-166908

DISCLOSURE OF THE INVENTION

Problems to be Solved by the Invention

However, for example, there is a case where image capturing is performed on other patients before performing the string of radiation image capturing and the radiation generating device and the radiation image capturing device are already set to be able to perform image capturing in a lying position. In this case, when the radiation technologist who performs the string of image capturing knows the above, the radiation technologist selects image capturing starting from "cervical vertebra open mouth" considering efficiency.

On the other hand, if the radiation technologist selects "cervical vertebra front face", etc., which performs image capturing in a standing position, not knowing that the devices are set as described above, it is necessary to start the radiation generating device and the radiation image capturing device again, to adjust the position and the emission direction of the radiation source of the radiation generating device, etc., or it is necessary to load the portable radiation image capturing device into a bucky device for image capturing in a standing position when the device is loaded into a bucky device for image capturing in a lying position.

However, this reduces the efficiency of image capturing when the entire radiation image capturing system is considered. Moreover, it is difficult to say that it is a system which is easy to use for an operator such as radiation technologist.

The present invention has been made in view of the above points, and the purpose is to provide a radiation image capturing system which is easy to use for an operator such as a radiation technologist and enables efficient radiation image capturing.

Means for Solving the Problem

According to one aspect of the present invention, there is provided a radiation image capturing system including:

a radiation source which emits radiation on an object;

a plurality of radiation image capturing devices which include a plurality of radiation detecting elements which are two dimensional, and which read charge generated in each radiation detecting element by the radiation emission as image data; and a console which manages which radiation image capturing device among the plurality of radiation image capturing devices is in a state where image capturing is possible, and which registers a plurality of pieces of image capturing order information including information of which radiation image capturing device is used in the image capturing among the plurality of radiation image capturing devices, or which can obtain the registered plurality of pieces of image capturing order information, wherein the console includes a display unit which can display an icon corresponding to each piece of image capturing order information;

the console displays each icon corresponding to each piece of image capturing order information in a predetermined order on the display unit; and when there is a radiation image capturing device in a state where image capturing is possible among the radiation image capturing devices included in the registered or obtained plurality of pieces of image capturing order information, regardless of the predetermined order, the console displays the icon corresponding to the image capturing order information including information of the radiation image capturing device in a manner different from the other icons.

According to another aspect of the present invention, there is provided a radiation image capturing system including:

a radiation source which emits radiation on an object;

a portable radiation image capturing device which includes a plurality of radiation detecting elements which are two dimensional, and which reads charge generated in each radiation detecting element by the radiation emission as image data;

a bucky device into which the portable radiation image capturing device can be loaded; and a console which manages at least whether or not the portable radiation image capturing device is loaded into the bucky device and which registers a plurality of pieces of image capturing order information including information of whether or not to perform image capturing in a state where the portable radiation image capturing device is loaded into the bucky device or which is possible to obtain the registered plurality of pieces of image capturing order information, wherein the console includes a display unit which can display an icon corresponding to each piece of image capturing order information;

the console displays each icon corresponding to each piece of image capturing order information in a predetermined order o on the display unit;

when the portable radiation image capturing device is loaded into the bucky device, regardless of the predetermined order, the console displays the icon corresponding to the image capturing order information including information showing that the portable radiation image capturing device is loaded into the bucky device in a manner different from the other icons; and when the portable radiation image capturing device is not loaded into the bucky device, regardless of the predetermined order, the console displays the icon corresponding to the image capturing order information including information showing that the portable radiation image capturing device is not loaded into the bucky device in a manner different from the other icons.

Advantageous Effect of the Invention

According to the radiation image capturing system with a format as described in the present invention, regardless of the order of the display of the icon corresponding to each piece of image capturing order information displayed on the display unit, when there is a radiation image capturing device (dedicated device) which is in a state to be able to perform capturing among a plurality of radiation image capturing devices (dedicated device) or when the portable radiation image capturing device is loaded into the bucky device, the console displays in a manner different from other icons the icon corresponding to the image capturing order information which specifies image capturing using a radiation image capturing device (dedicated device) which is able to perform image capturing or the icon corresponding to the image capturing order information which specifies performing image capturing in a state where the portable radiation image capturing device is loaded into the bucky device.

Therefore, if image capturing is performed based on the image capturing order information corresponding to the icon displayed in a manner different from other icons, the operator such as the radiation technologist can perform image capturing without newly setting the radiation image capturing device (dedicated device) in a state to be able to perform capturing or changing the state of loading the portable radiation image capturing device into the bucky device. Therefore, the radiation image capturing system can be easily used and the radiation image capturing can be performed efficiently.

BRIEF DESCRIPTION OF THE DRAWINGS

FIG. 13 is a diagram showing an example of image capturing order information;

FIG. 14 is a diagram showing an example of a selection screen displaying image capturing order information;

FIG. 15 is a diagram showing an example of a screen which displays each icon corresponding to each piece of image capturing order information;

FIG. 29 is a diagram showing an example of a table of order of transmission of the string of medical images from the console to the interpretation image management device determined in a default state;

FIG. 31 is a diagram showing an example of the history table in which the order of transmission is modified due to change in the order with the image display device, etc.;

FIG. 32 is a diagram showing an example of a transmission preview screen displayed on the screen of the display unit and an example of each medical image displayed arranged in order;

FIG. 34 is a diagram showing the order of display of each medical image displayed below the transmission preview screen shown in FIG. 33 can be changed; and FIG. 35 is a diagram showing when the "enter" button of the transmission preview screen shown in FIG. 34 is clicked, each medical image is displayed in a changed order of display.

EMBODIMENT FOR CARRYING OUT THE INVENTION

An embodiment of the radiation image capturing system of the present invention is described with reference to the drawings. However, the present invention is not limited to the illustrated examples.

[First Embodiment]

Figure 1:
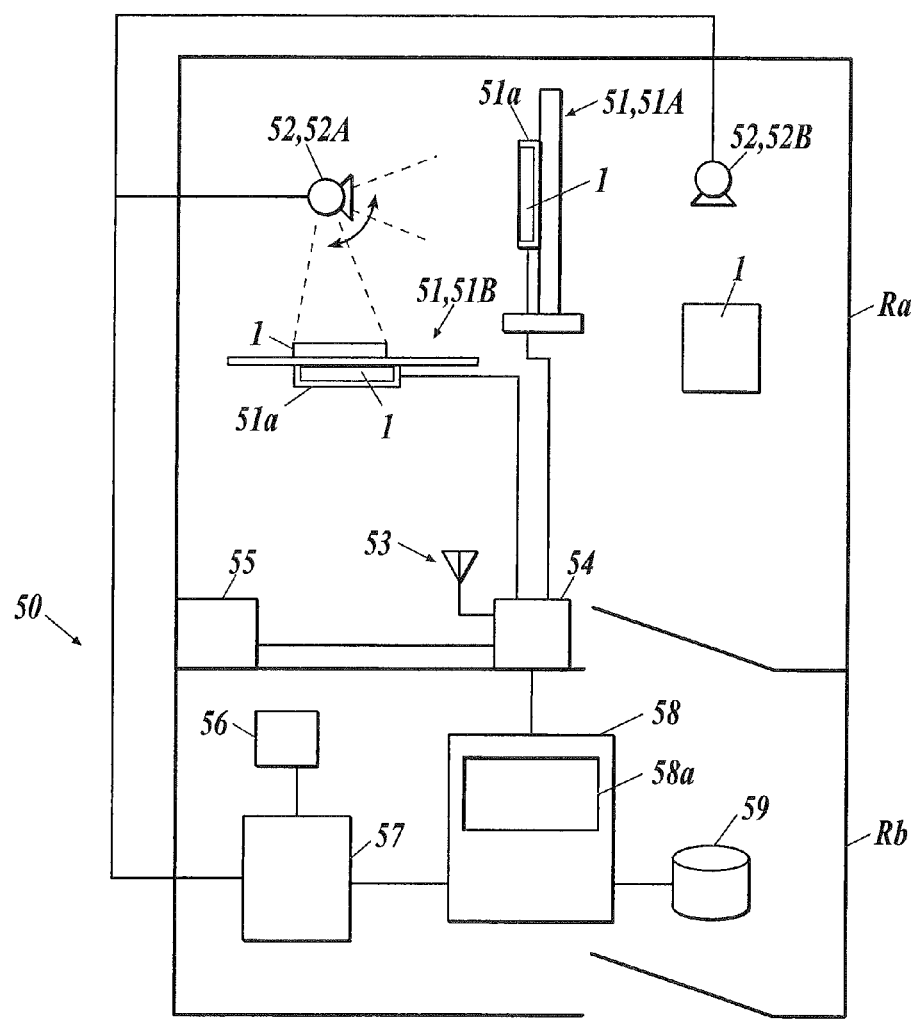
FIG. 1 is a diagram showing an entire configuration of the radiation image capturing system according to a first embodiment.

FIG. 1 is a diagram showing an entire configuration of the radiation image capturing system according to the first embodiment of the present invention.

An image capturing room Ra is a room in which radiation image capturing is performed by emitting radiation to an object which is a portion of a body of a patient (in other words, a capturing portion of the patient). A radiation source 52, etc. of a radiation generating device 57 of a radiation emitting device to emit radiation to an object is provided in the image capturing room Ra. The image capturing room Ra is shielded with lead so that radiation does not leak outside of the image capturing room.

According to the present embodiment, a portable radiation image capturing device 1 as described below is used as the radiation image capturing device. In the image capturing room Ra, a bucky device 51 into which a portable radiation image capturing device 1 can be loaded is provided. The bucky device 51, the radiation source 52, etc. are described later.

Here, first the portable radiation image capturing device 1 used in the radiation image capturing with the radiation image capturing system 50 is described.

Below, the portable radiation image capturing device is referred as simply the radiation image capturing device. Below, as the radiation image capturing device 1, the present embodiment describes an indirect radiation image capturing device including a scintillator, etc. and which converts emitted radiation to an electromagnetic wave with another wavelength such as visible light to obtain an electric signal. However, the present invention can be applied to a direct radiation image capturing device in which radiation is directly detected with a radiation detecting element without a scintillator, etc.

Figure 2:
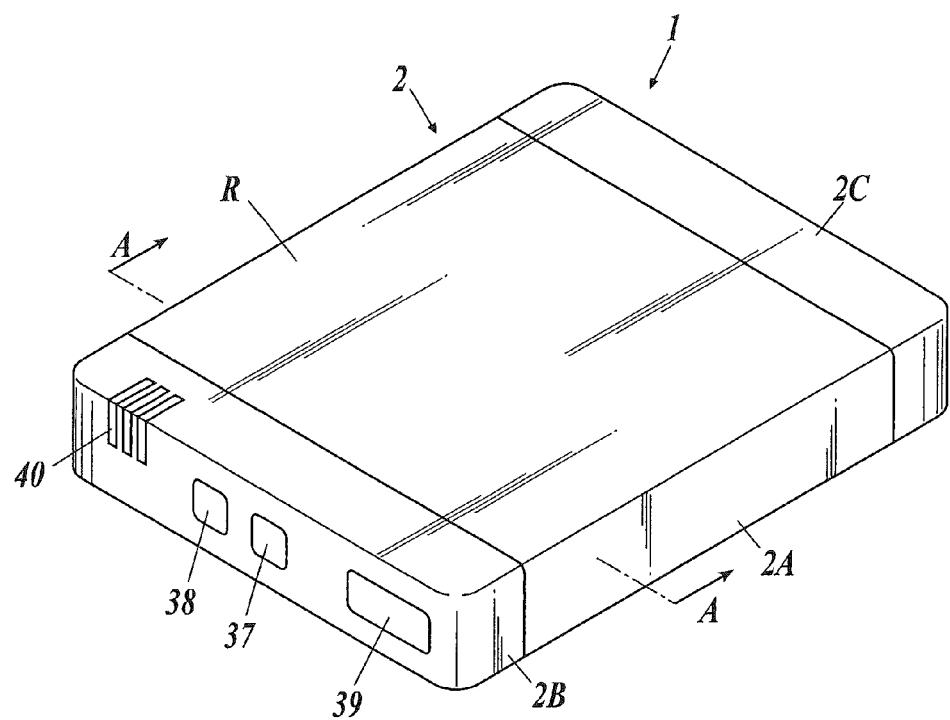
FIG. 2 is a perspective view of an external appearance of a portable radiation image capturing device according to the first embodiment.
Figure 3:
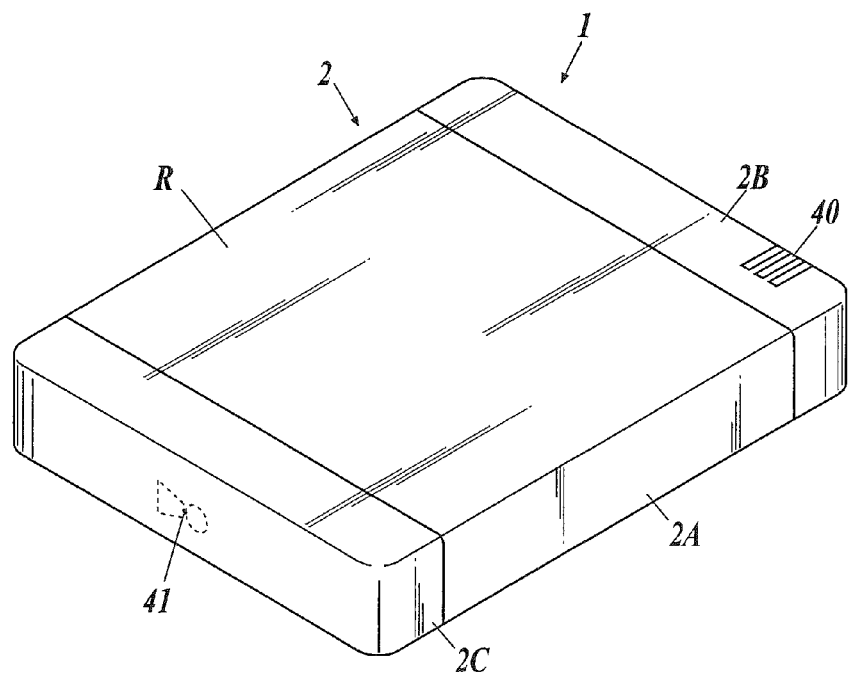
FIG. 3 is a perspective view of an external appearance viewing the portable radiation image capturing device shown in FIG. 2 from the opposite side.
Figure 4:
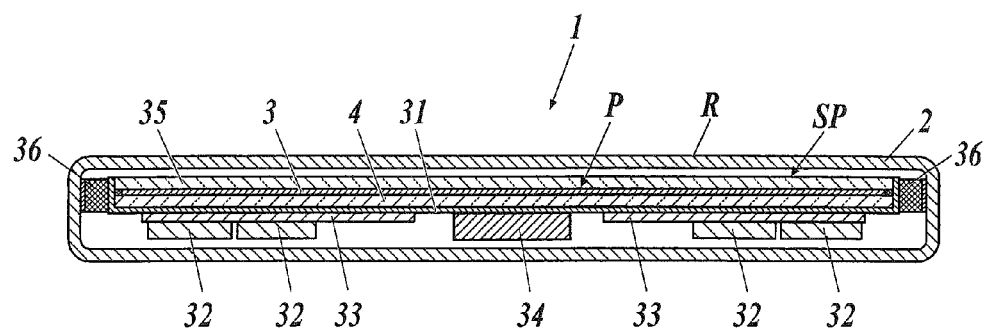
FIG. 4 is a cross sectional diagram along line A-A shown in FIG. 2.

FIG. 2 is a perspective view of an external appearance of the radiation image capturing device according to the present embodiment and FIG. 3 is a perspective view of an external appearance of the radiation image capturing device viewed from the opposite side. FIG. 4 is a cross sectional diagram along line A-A shown in FIG. 2. As shown in FIG. 2 to FIG. 4, in the radiation image capturing device 1, a sensor panel SP including a scintillator 3, substrate 4, etc. is stored in a housing 2 in a box shape.

As shown in FIG. 2 and FIG. 3, in the box 2 of the present embodiment, a housing main unit 2A in a hollow square tube shape including a radiation entering face R is formed with a material such as carbon plate, plastic, etc. which transmits radiation, and the box 2 is formed by closing openings on both sides of the housing main unit 2A with cover members 2B and 2C. Instead of forming the box 2 in such monocoque shape, for example, the box 2 can be formed in a lunch box shape formed with a frame plate and a back plate.

As shown in FIG. 2, a cover member 2B on one side of the box 2 is provided with a power source switch 37, a selection switch 38, a connector 39, an indicator 40 which includes an LED, etc. which displays battery state and operating state, etc. of the radiation image capturing device 1 and the like.

As shown in FIG. 3, an antenna device 41 which is a communication unit is embedded in the cover member 2C on the opposite side of the box 2 to wirelessly transfer image data, etc. to the console 58. It is also possible to transfer image data, etc. to the console 58 in a wired format. In this case, for example, transmission and reception is performed by connecting a cable etc. to the connector 39. When an antenna device 41 is provided, the position and the number of antenna devices 41 provided on the box 2 is suitably determined.

As shown in FIG. 4, inside the box 2, a base 31 is provided through a lead thin plate, etc. which is not shown on a lower side of a substrate 4 of a sensor panel SP. A PCB substrate 33 provided with electronic components 32, etc., a buffering member 34 and the like are attached to the base 31.

In the present embodiment, a glass substrate 35 is provided on the substrate 4 and the scintillator 3 on the side of the radiation entering face R to protect the above. In the present embodiment, a buffer 36 is provided between the side face of the box 2 and the sensor panel SP to prevent collision.

The scintillator 3 is pasted to a later described detecting unit P of the substrate 4. For example, the present embodiment employs a scintillator 3 with phosphor as the main component, and when radiation enters, the radiation is converted and output to an electromagnetic wave with a wavelength of 300 to 800 nm, in other words, an electromagnetic wave mainly of visible light.

Figure 5:
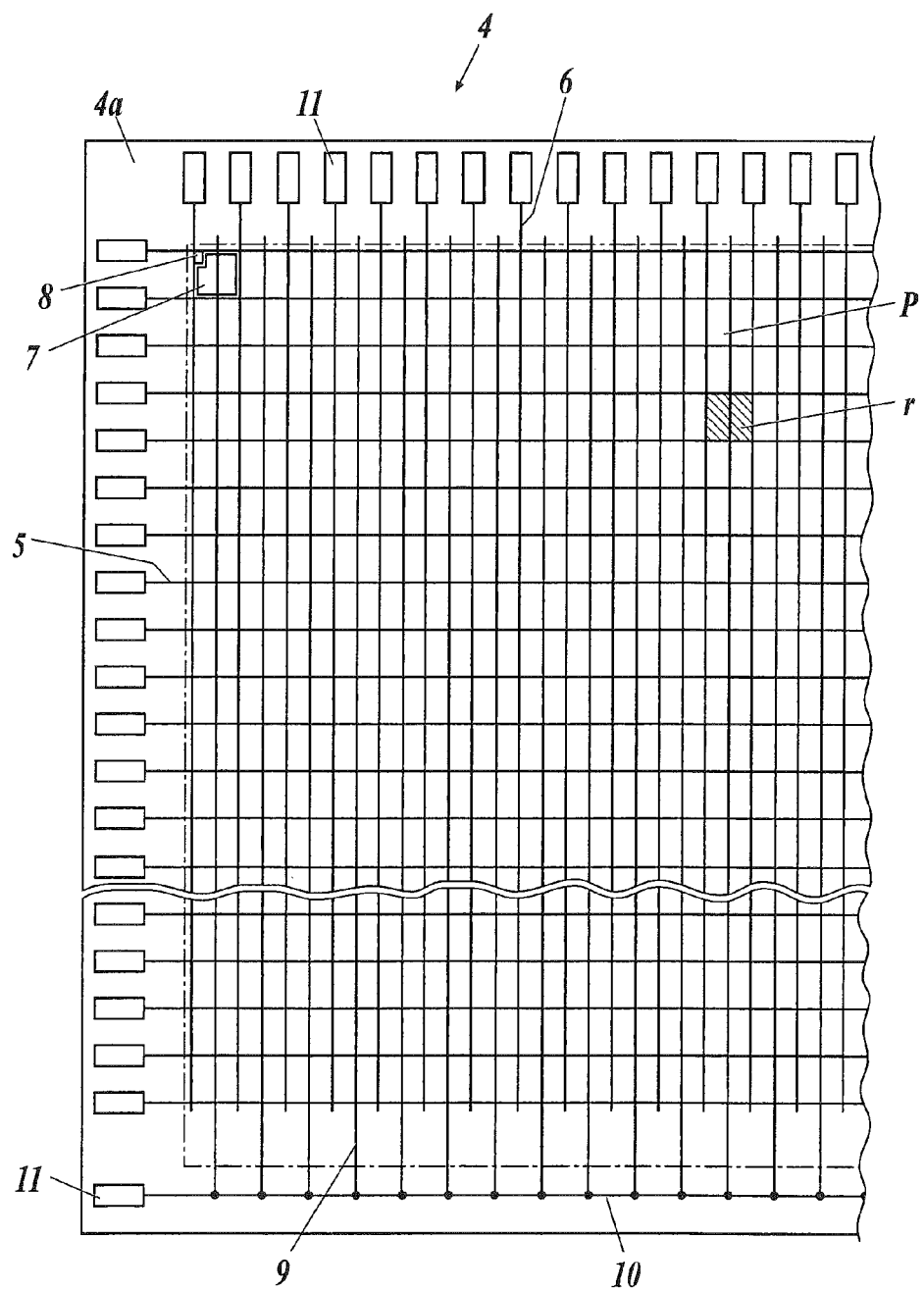
FIG. 5 is a planar view showing a configuration of a substrate of the portable radiation image capturing device.

In the present embodiment, the substrate 4 is a glass substrate, and as shown in FIG. 5, a plurality of scanning lines 5 and a plurality of signal lines 6 are provided to intersect each other on a face 4a of the substrate 4 on a side opposite of the scintillator 3. A radiation detecting element 7 is provided in each small region r defined by the plurality of scanning lines 5 and the plurality of signal lines 6 on the face 4a of the substrate 4.

As described above, a region defined into small regions r by scanning lines 5 and signal lines 6 is provided with a plurality of radiation detecting elements 7 provided in two dimensions and the entire region of the region r, in other words, the region shown with alternate long and short dash line in FIG. 5 is to be the detecting section P.

Figure 6:
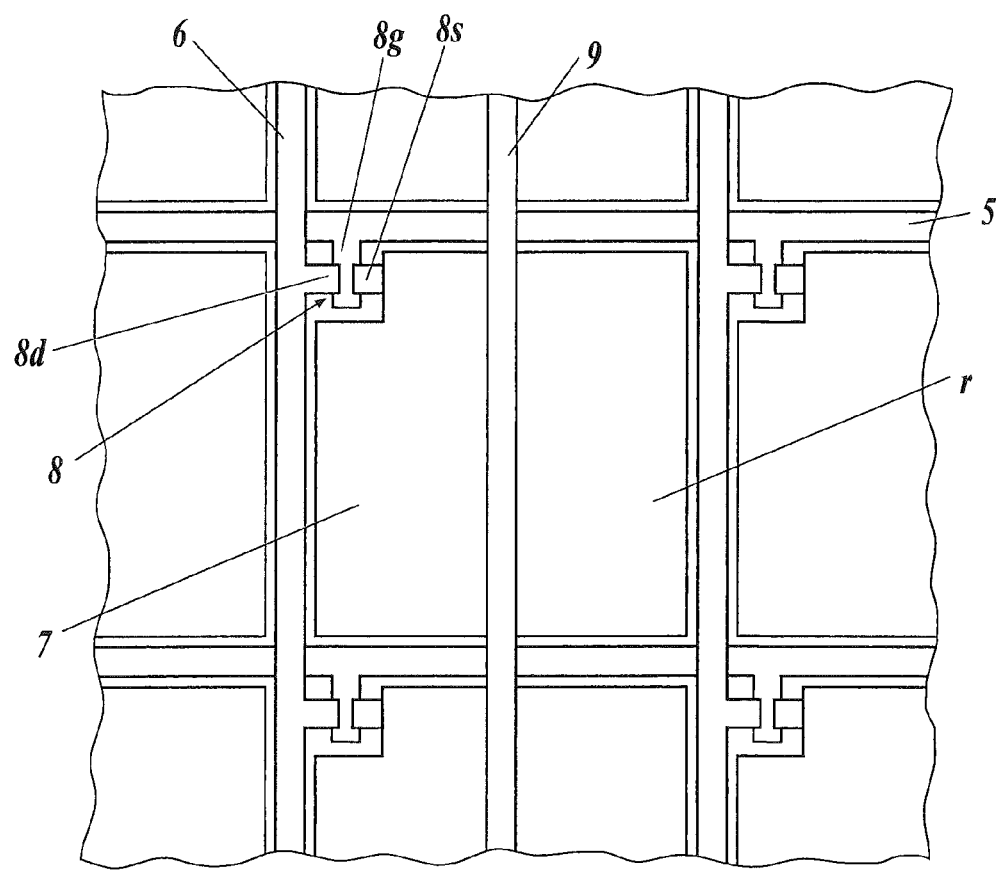
FIG. 6 is an enlarged diagram showing a configuration of radiation detecting elements, TFT, etc. formed in a small region on the substrate shown in FIG. 5.

In the present embodiment, a photodiode is used as the radiation detecting element 7, however, it is possible to use other material such as a phototransistor. As shown in FIG. 6 which is an enlarged diagram of FIG. 5, each radiation detecting element 7 is connected to a source electrode 8s of a TFT 8 which is a switch unit. A drain electrode 8d of the TFT 8 is connected to a signal line 6.

When the on voltage is applied to the gate electrode 8g through the scanning line 5 from a later described scanning driving unit 15, the TFT 8 becomes the on state, and charge accumulated in the radiation detecting element 7 is discharged to the signal line 6 through the source electrode 8s and the drain electrode 8d. When the off voltage is applied to the gate electrode 8g through the connected scanning line 5, the TFT 8 becomes the off state, and discharge of charge from the radiation detecting element 7 to the signal line 6 stops to hold charge in the radiation detecting element 7.

According to the present embodiment, as shown in FIG. 6, a plurality of radiation detecting elements 7 provided in columns are connected to each bias line 9 and as shown in FIG. 5, each bias line 9 is band by one connecting line 10 in a position outside the detecting unit P of the substrate 4.

Figure 7:
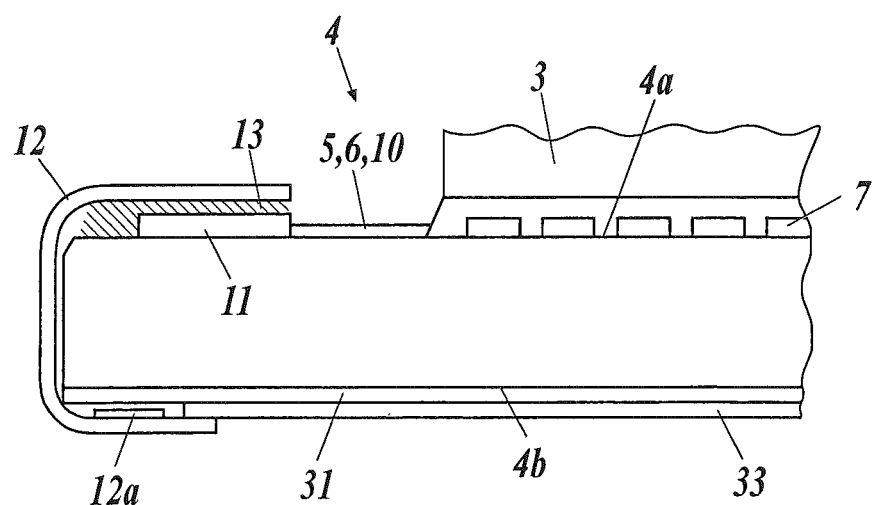
FIG. 7 is a side diagram describing a substrate on which a COF, PCB substrate, etc. are attached.

Each scanning line 5, each signal line 6, and the connecting line 10 of the bias line 9 are connected to an input/output terminal (pad) 11 provided near the edge of the substrate 4. As shown in FIG. 7, a COF (Chip On Film) 12 with a chip such as IC 12a, etc. embedded on a film is connected to each input/output terminal 11 through an anisotropic conductive material 13 such as an anisotropic conductive film or anisotropic conductive paste.

Then, the COF 12 is pulled to a rear surface 4b side of the substrate 4 and connected to the above described PCB substrate 33 on the rear surface 4b side. With this, the substrate 4 portion of the sensor panel SP of the radiation image capturing device 1 is formed. In FIG. 7, the illustration of the electronic components 32, etc. is omitted.

Figure 8:
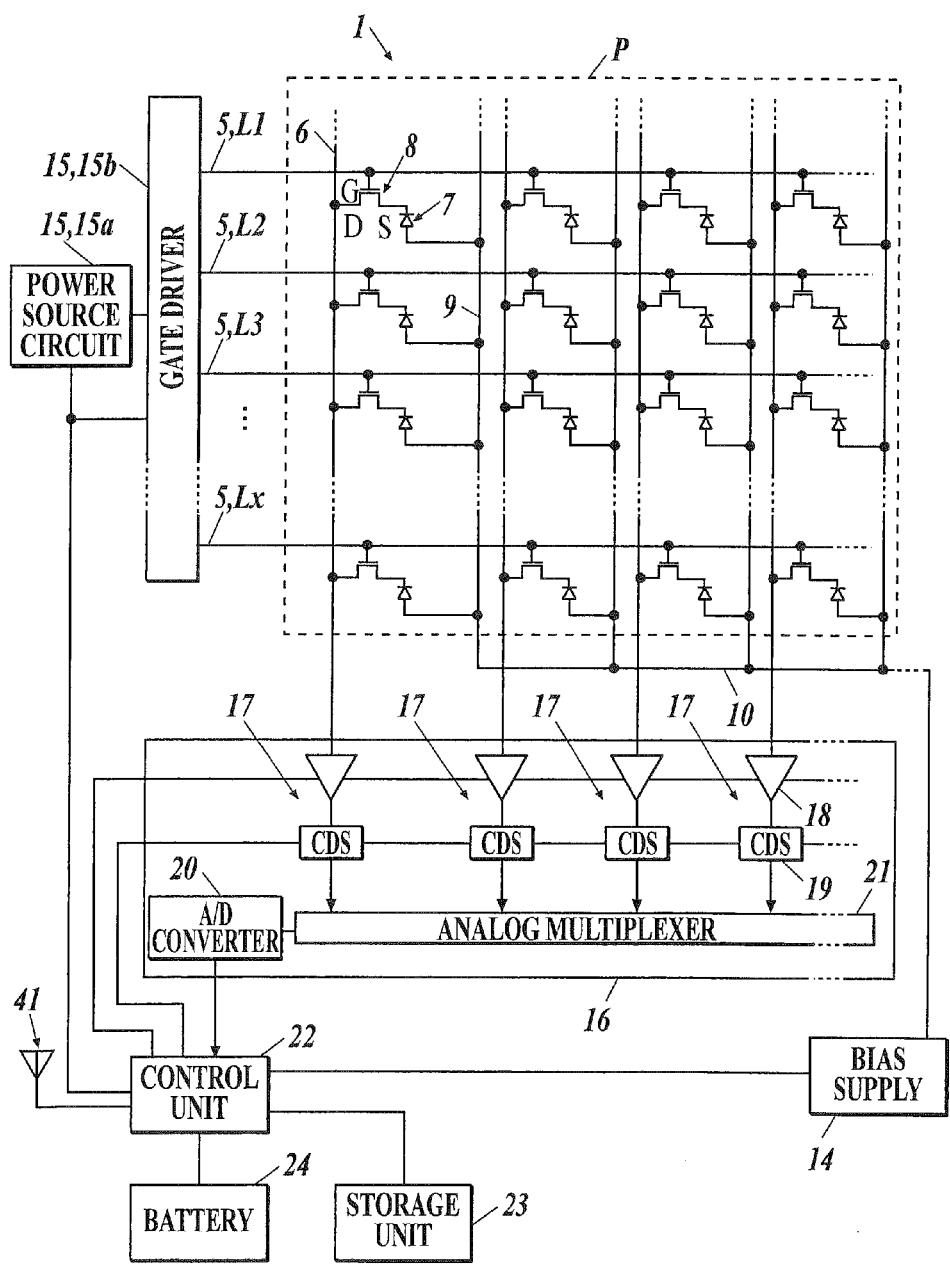
FIG. 8 is a block diagram showing an equivalent circuit of the portable radiation image capturing device.

Here, the circuit configuration of the radiation image capturing device 1 is described with reference to FIG. 8.

As described above, each bias line 9 is connected to one electrode of each radiation detecting element 7, and the bias lines 9 are band by the connecting line 10 to be connected to the bias supply 14. The bias supply 14 applies a bias voltage (in the present embodiment, reverse bias voltage) to each electrode of each radiation detecting element 7 through the connecting line 10 and each bias line 9.

The other electrode of each radiation detecting element 7 is connected to a source electrode 8s (described as S in FIG. 8) of the TFT 8 and the gate electrode 8g (described as G in FIG. 8) of each TFT 8 is connected to each line L1 to Lx of the scanning line 5 extending from the gate driver 15b of the scanning driving unit 15. The drain electrode 8d (described as D in FIG. 8) of each TFT 8 is connected to each signal line 6.

The scanning driving unit 15 includes a power source circuit 15a which supplies an on voltage and an off voltage to a gate driver 15b, and the gate driver 15b which switches the voltage applied to each line L1 to Lx of the scanning line 5 between the on voltage and the off voltage. As described above, the gate driver 15b switches the voltage applied to the gate electrode 8g of the TFT 8 through each line L1 to Lx of the scanning line 5 between the on voltage and the off voltage to control the on state and the off state of the TFT 8.

Each signal line 6 is connected to each reading circuit 17 formed in the reading IC 16. The reading circuit 17 includes an amplifying circuit 18, a correlated double sampling circuit 19, an analog multiplexer 21 and an A/D converter 20.

For example, in the radiation image capturing, when radiation is emitted to the radiation image capturing device 1 through the object, the radiation is converted to an electromagnetic wave in another wavelength in the scintillator 3, and the converted electromagnetic wave is emitted to the radiation detecting element 7 directly below. Then, charge is generated in the radiation detecting element 7 according to the amount of emitted radiation (in other words, amount of electromagnetic wave).

In the reading processing of the image data from each radiation detecting element 7, when on voltage is applied to a predetermined line Ln of the scanning line 5 from the gate driver 15b of the scanning driving unit 15, on voltage is applied to the gate electrode 8g of each TFT 8 connected through the line Ln of the scanning line 5 and each TFT 8 becomes an on state, and charge is discharged to the signal line 6 from the radiation detecting element 7 connected to each TFT 8 in an on state through each TFT 8.

Then, a voltage value is output from the amplifying circuit 18 according to the charge amount discharged from the radiation detecting element 7 and correlated double sampling by the correlated double sampling circuit 19 is performed to output the image data D with an analog value to the multiplexer 21. The image data D sequentially output from the multiplexer 21 is sequentially converted to the image data D with a digital value in the A/D converter 20 and output to the storage unit 23 to be sequentially stored.

The control unit 22 includes a computer including a CPU (Central Processing Unit), a ROM (Read Only Memory), a RAM (Random Access Memory), an input/output interface, etc. connected to a bus, a FPGA (Field Programmable Gate Array), and the like which are not shown. The control unit 22 can include a dedicated control circuit.

The control unit 22 controls operation, etc. of each functional unit such as the scanning driving unit 15, reading circuit 17, etc. of the radiation image capturing device 1. A storage unit 23 including a DRAM (Dynamic RAM), etc., and a battery 24 which supplies electric power to each functional unit of the radiation image capturing device 1 are connected to the control unit 22. The above described antenna device 41 is connected to the control unit 22.

When the radiation image capturing is performed, the control unit 22 performs the reading processing which reads the charge from each radiation detecting element 7, in other words, the image data D, as described above. In the present embodiment, the control unit 22 thins out each piece of image data at a predetermined percentage to create thinned out data Dt for preview based on each piece of image data D stored in the storage unit 23 read out from each radiation detecting element 7.

In the present embodiment, when the radiation image capturing ends and the image data D is read from each radiation detecting element 7 to be stored in the storage unit 23, the control unit 22 immediately creates the thinned out data Dt. Then, when the thinned out data Dt is created, a cassette ID which is identification information of the radiation image capturing device 1 is immediately applied to the thinned out data Dt and the data is transmitted to a later described console 58. The transmission of the thinned out data Dt is performed for each radiation image capturing.

In the present embodiment, as described below, when the radiation image capturing device 1 is used by itself without loading into the bucky device 51 (in other words, when nothing is connected to the connector 39 (see FIG. 2)), the control unit 22 transmits to the console 58 the thinned out data Dt, the image data D, a later described offset correction value O, etc. in a wireless format through the antenna device 41. Alternatively, when the radiation image capturing device 1 is used loaded into the bucky device 51 (in other words, when the connector 51b (see FIG. 9 and FIG. 10) of the bucky device 51 is connected to the connector 39), the control unit 22 transmits to the console 58 thinned out data Dt etc. in a wired format through the bucky device 51.

Thinned out data Dt can be created by, for example, when each piece of image data D is arranged corresponding to each radiation detecting element 7 arranged two dimensionally, image data D of one pixel can be extracted for every 3×3 pixels or 4×4 pixels or as in image data D from each radiation detecting element 7 connected to each line L1, L4, L7, etc. of the scanning line 5, image data D can be extracted from each radiation detecting element 7 connected to each line Ln for each predetermined interval of the scanning line 5.

In the present embodiment, after the thinned out data Dt is transmitted to the console 58, the control unit 22 applies a cassette ID to the image data D corresponding to the source of creating the thinned out data Dt and the data is automatically transmitted to the console 58.

Instead of creating and transmitting the thinned out data Dt, it is possible to transmit the image data D from the beginning. It is possible to transmit the image data D at the point when there is a transmission instruction from the console 58, etc.

It is possible to allow only the image data D other than the thinned out data Dt already transmitted to be transmitted among the image data D when the image data D is transmitted. In this case, the console 58 restores the whole image data D by combining the thinned out data Dt already received and the newly transmitted other image data D.

In the present embodiment, the control unit 22 automatically performs the dark reading processing to obtain the offset correction value O in order to correct the offset amount overlapped on the image data D obtained by the radiation image capturing when each radiation image capturing finishes or when a string of radiation image capturing finishes. It is possible to perform the dark reading processing before a single or a string of radiation image capturing starts.

In the dark reading processing, after each TFT 8 of the radiation image capturing device 1 is in an off state and the radiation image capturing device 1 is left for a predetermined amount of time without emitting radiation to the radiation image capturing device 1, similar to the above reading processing, accumulated dark charge, etc. is read as the dark reading value d from each radiation detecting element 7 and stored in the storage unit 23.

Then, the control unit 22 sets the read dark reading value d for each radiation detecting element 7 to the offset correction value O or performs the dark reading processing a plurality of times to average the plurality of dark reading values d obtained for each radiation detecting element 7 to calculate the offset correction value O. Then, the cassette ID which is the identification information of the radiation image capturing device 1 is applied to the offset correction value O to be automatically transmitted to the console 58.

In the present embodiment, as described later, when the radiation image capturing device 1 is brought in the image capturing room Ra, the radiation image capturing device 1 is inserted in a later described cradle 55 which is the detecting unit. Here, when the radiation image capturing device 1 is inserted in the cradle 55, and the connector 39 (see FIG. 2) is connected to a connector 55a of the cradle 55 (see later described FIG. 11), the control unit 22 notifies the cassette ID which is the identification information of the radiation image capturing device 1 to a later described base station 54 (see FIG. 1) through the cradle 55.

When the selection switch 38 (see FIG. 2) which is the selection unit is pressed by an operator such as a radiation technologist, etc., the cassette ID which is its identification information and a selection signal showing that it is selected is transmitted to the console 58 through the antenna device 41.

As described later, in the present embodiment, the portable radiation image capturing device 1 is a size compatible with a CR cassette and can be loaded into the later described bucky device 51 existing in a facility.

When the radiation image capturing device 1 is loaded into the bucky device 51, the radiation image capturing device 1 receives supply of electric power from the bucky device 51. When the radiation image capturing device 1 is in a state by itself not loaded into the bucky device 51, the battery 24 (see FIG. 8) supplies electric power to each functional unit such as the control unit 22, the bias supply 14, the scanning driving unit 15, the reading circuit 17 (reading IC 16), etc. When the radiation image capturing device 1 is loaded into the bucky device, transfer of image data, communication regarding control, etc. are performed wired through the bucky device 51.

As described below, when the radiation image capturing device 1 is loaded into the bucky device 51, the radiation image capturing device 1 receives supply of electric power from the bucky device 51. When the radiation image capturing device 1 is by itself and not loaded into the bucky device 51, the battery 24 (see FIG. 8) supplies electric power to each functional unit such as the control unit 22, the bias supply 14, the scanning driving unit 15, the reading circuit 17 (reading IC 16).

Then, if the electric power is supplied to each functional unit when the radiation image capturing, the reading processing of the image data D, etc. is not performed, the battery 24 is consumed. Therefore, the mode of the radiation image capturing device 1 can be switched between an image capturing possible mode which is a state where electric power is supplied to each functional unit so that radiation image capturing can be performed, in other words a state where image capturing can be performed, and a sleep mode where electric power is not supplied to each functional unit when radiation image capturing is not performed.

In the sleep mode, electric power is supplied to only the minimum functional units which need to be started in order to receive signals from the console 58, etc., such as the antenna device 41, the control unit 22, etc. and electric power is not supplied to the bias supply 14, the scanning driving unit 15, the reading circuit 17, the reading IC 16, etc.

It is suitably set whether the radiation image capturing device 1 is started with the image capturing possible mode or the sleep mode when the power source switch 37 (see FIG. 2) is pressed. At least when the selection switch 38 is pressed, if the radiation image capturing device 1 is in the sleep mode, the mode of the radiation image capturing device 1 is switched to the image capturing possible mode.

When the radiation image capturing is not performed for a predetermined amount of time after switching to the image capturing possible mode, the radiation image capturing device 1 automatically switches the mode to sleep mode when a predetermined amount of time passes.

Then, when the mode switches, the radiation image capturing device 1 transmits the signal showing that the mode is the image capturing possible mode or the signal showing that the mode is the sleep mode together with its cassette ID to the console 38.

Next, each device, etc. in the radiation image capturing system 50 is described.

As shown in FIG. 1, in the present embodiment, the bucky device 51 can be used by loading the portable radiation image capturing device 1 into the cassette holding unit (cassette holder) 51*a*.

As shown in FIG. 1, in the present embodiment, a bucky device 51A for image capturing in a standing position and a bucky device 51B for image capturing in a lying position are provided in the image capturing room Ra as the bucky device 51. Alternatively, for example, the present invention can be applied when only the bucky device 51A for image capturing in a standing position or only the bucky device 51B for image capturing in a lying position are provided.

In the present embodiment, the bucky device 51 can be used by loading a conventional CR cassette into the cassette holding unit 51*a* and it is possible to use an existing bucky device provided for a CR cassette in the image capturing room Ra.

Therefore, in the present embodiment, the above described portable radiation image capturing device 1 is formed to be the same dimension as the CR cassette.

In other words, the CR cassette is formed in compliance with the JIS standard size (corresponding international standard is IEC 60406) of the conventional screen film cassette, and the dimension is 14 inches×17 inches (half cut size). The thickness of the radiation entering direction is formed to be within the range of 15 mm+1 mm to 15 mm−2 mm.

Therefore, in the present embodiment, in order to enable use by loading into the bucky device 51 into which the CR cassette with the JIS standard size can be loaded, the portable radiation image capturing device 1 is formed in a dimension in compliance with the JIS standard of a screen film cassette in compliance with the CR cassette.

When the existing bucky device for the screen/film cassette or the CR cassette is not used, it is not necessary to form the radiation image capturing device 1 in the above dimension, and the radiation image capturing device 1 can be formed in any size or shape. However, here, as the bucky device 51, it is necessary to newly provide in the image capturing room Ra a bucky device in which the radiation image capturing device 1 in any set shape can be loaded.

Figure 9:
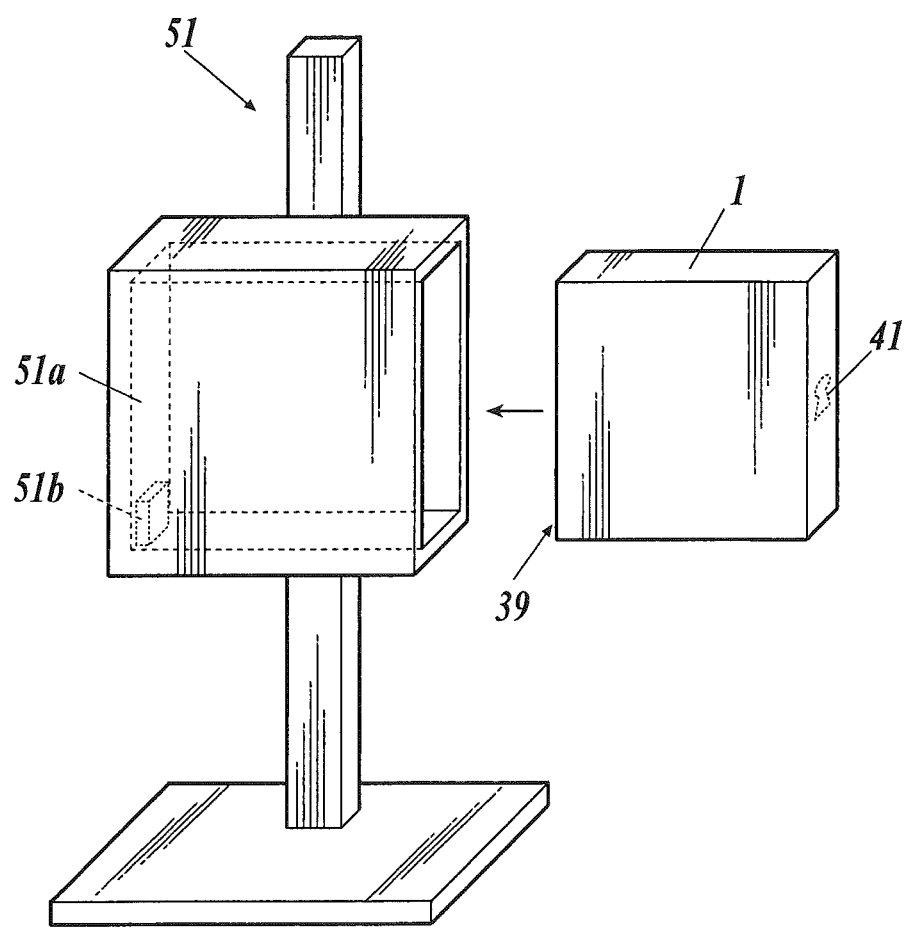
FIG. 9 is a diagram describing a bucky device in which a connector is provided inside the cassette holding unit.

As shown in FIG. 9, in the present embodiment, a connector 51*b* which is connected to the connector 39 (see FIG. 2) of the loaded radiation image capturing device 1 is provided in the cassette holding unit 51*a* of the bucky device 51.

Figure 10:
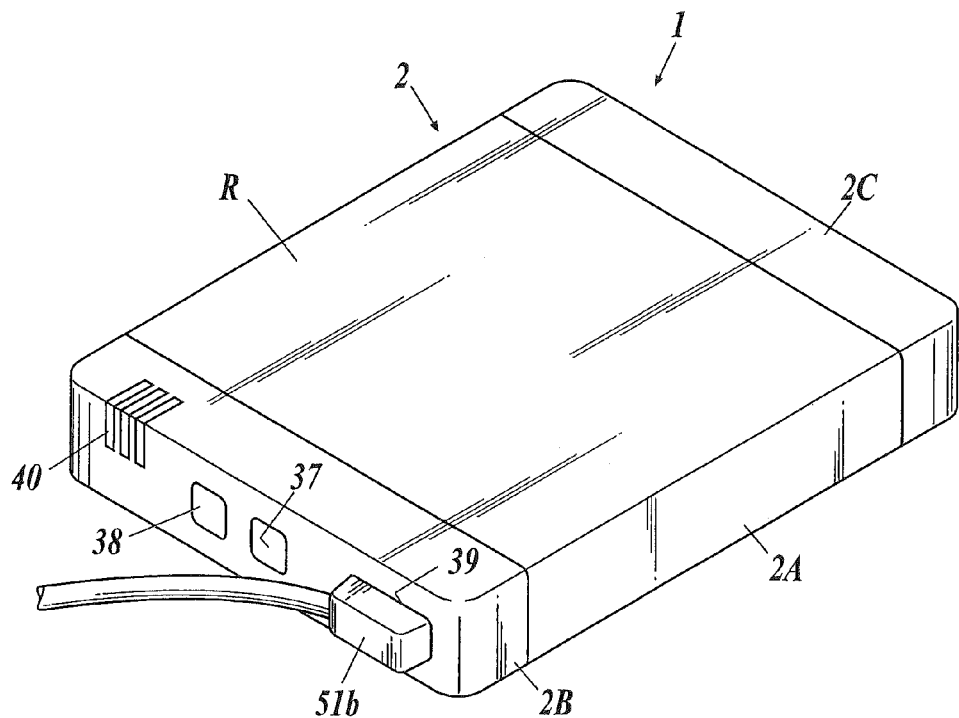
FIG. 10 is a perspective view of an external appearance showing a state where the connector of the portable radiation image capturing device is connected to the connector of the bucky device.

FIG. 9 shows an example of using the bucky device 51A for image capturing in a standing position, however the same can be said for the bucky device 51B for image capturing in a lying position. Alternatively, instead of providing a connector 51*b* inside the cassette holding unit 51*a* of the bucky device 51, as shown in FIG. 10, before loading the radiation image capturing device 1 to the bucky device 51, the connector 51*b* provided to a tip of a cable extending from the bucky device 51 can be connected to the connecter 39 of the radiation image capturing device 1 and the radiation image capturing device 1 can be loaded on the cassette holding unit 51*a* of the bucky device 51.

In the present embodiment, when the connector 51*b* is connected to the connector 39 of the radiation image capturing device 1, the bucky device 51 reads the cassette ID which is the identification information from the radiation image capturing device 1 and corresponds the cassette ID of the radiation image capturing device 1 with the bucky ID which is its identification information and transmits the above to the console 58.

As described above, in the present embodiment, when the radiation image capturing device 1 is used loaded into the cassette holding unit 51a, the bucky device 51 transmits to the console 58 by transmitting in a wired format to the later described base station 54 the thinned out data Dt, the image data D, and the off set correction value O output from the radiation image capturing device 1 through the connector 39.

In the present embodiment, when the connector 51b of the bucky device 51 is connected to the connector 39 of the radiation image capturing device 1, electric power is supplied from the bucky device 51 to the radiation image capturing device 1. Therefore, when the connector 39 and the connector 51b are connected to each other, the control unit 22 of the radiation image capturing device 1 stops supply of electric power from the battery 24 (see FIG. 8) to each functional unit and switches so that electric power is supplied to each functional unit through the connector 39 from the bucky device 51. The battery 24 can be charged while supplying electric power to each functional unit.

As described above, in the present embodiment, the bucky device 51 can be used loading a conventional CR cassette into the cassette holding unit 51a and although illustration is omitted, it is preferable that a barcode reader, etc. which is a reading unit which optically reads a barcode (not shown) of the CR cassette when the CR cassette is loaded is provided in the cassette holding unit 51a of the bucky device 51.

When the barcode reader reads the barcode of the CR cassette, the bucky device 51 reads the barcode information which is the identification information of the CR cassette from the read information and corresponds the barcode information of the CR cassette with the bucky ID which is its identification information to be transmitted to the console 58. When the barcode information is transmitted, it can be understood that the image capturing is performed in a CR format and it is possible to control switching so that the emitted radiation amount of the X-ray generating device corresponds to the CR format (increase the emitted radiation amount than image capturing in the FPD format). After the image capturing, the CR cassette is loaded into one of the plurality of CR reading devices provided in another place and by transmitting to the server, etc. the cassette ID and the image data read by the CR reading device as a pair, the console can obtain the read image data with the cassette ID as the key, and the image capturing order information can be corresponded with the image data.

As shown in FIG. 1, in the image capturing room Ra, at least one radiation source 52 is provided to emit radiation to the object. In the present embodiment, among the radiation sources 52, for example, one radiation source 52A is positioned hanged from the ceiling of the image capturing room Ra and when the image capturing is performed, the radiation source 52A is started based on the instruction from the console 58 and is moved to a predetermined position by a moving unit not shown. Then, the emission direction of the radiation is changed so that the radiation can be emitted to the radiation image capturing device 1 loaded into the bucky device 51A for image capturing in a standing position and the bucky device 51B for image capturing in a lying position.

The present embodiment is provided with a portable radiation generating device 52B which is not corresponded to the bucky device 51A for image capturing in a standing position and the bucky device 51B for image capturing in a lying position. The portable radiation generating device 52B can be moved to any position in the image capturing room Ra and can emit radiation in any direction.

The portable radiation generating device 52B can be used to emit radiation from a suitable distance or direction where the radiation image capturing device 1 is in a state by itself (in other words, in a state not loaded into the bucky device 51) and placed against a portion of the body of the patient who is the object or inserted between the body of the patient and the table (bed) of the bucky device 51B for image capturing in a lying position or a dedicated bed not shown.

In the present embodiment, the portable radiation image capturing device 1 can be used in the radiation image capturing in a state by itself not loaded on the bucky device 51.

The radiation source 52 includes an X-ray tube bulb. When a predetermined tube voltage or a tube current is supplied from the later described radiation generating device 57, the X-ray tube bulb emits radiation of an amount according to the tube voltage, etc. for an emitting time specified from the radiation generating device 57.

As described above, since the image capturing room Ra is shielded by lead, etc., it is not possible to transmit or receive information such as image data D as is through the antenna device 41 from the radiation image capturing device 1 in the image capturing room Ra. As shown in FIG. 1, when wireless communication is performed between the radiation image capturing device 1 and the console 58, the present embodiment is provided with the base station (wireless access point) 54 including the wireless antenna 53 to relay the communication.

As described above, in the present embodiment, the bucky device 51 and the base station 54 are connected with a cable, etc., and when the radiation image capturing device 1 is used loaded into the bucky device 51, the thinned out data Dt, etc. output from the radiation image capturing device 1 is transmitted to the console 58 in a wired format through the bucky device 51, the base station 54, and the like.

Figure 11:
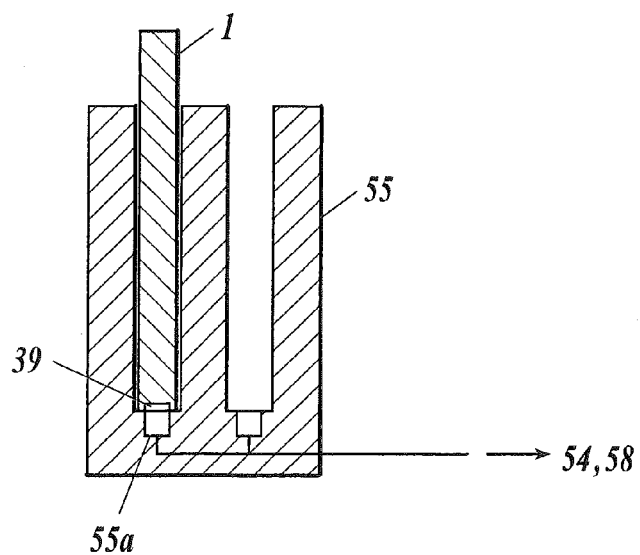
FIG. 11 is a cross sectional diagram showing a state in which the portable radiation image capturing device is inserted in the cradle and the connectors are connected to each other.

The cradle 55 is connected to the base station 54. As shown in FIG. 11, when the radiation image capturing device 1 brought into the image capturing room Ra is inserted in the cradle 55 and the connector 39 of the radiation image capturing device 1 is connected to the connector 55a of the cradle 55, the cassette ID is notified from the radiation image capturing device 1 to the base station 54 through the cradle 55 as described above. When the cassette ID of the radiation image capturing device 1 is transmitted from the cradle 55, the base station 54 notifies the cassette ID to the console 58.

The cradle 55 is usually used to store and charge the radiation image capturing device 1, etc. In the present embodiment, the cradle 55 can include functions such as charging. FIG. 11 shows the cradle 55 provided with two inserting openings to insert the radiation image capturing device 1. The inserting opening provided can be one or can be three or more.

The cradle 55 can be provided in any of the image capturing room Ra and the front room Rb. When the cradle 55 is provided in the image capturing room Ra, the cradle 55 is provided in the position where the radiation emitted from the radiation generating device 52 cannot reach, in other words, for example, a position in a corner of the capturing room Ra.

Figure 12:
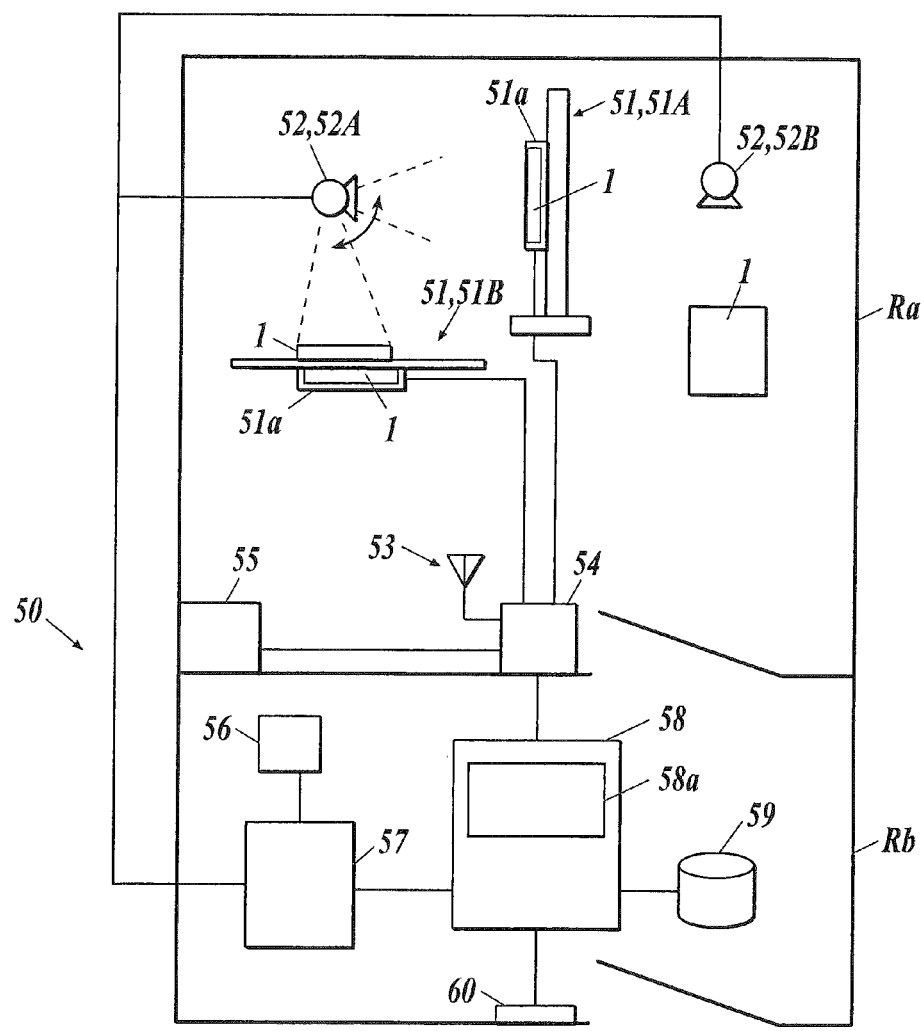
FIG. 12 is a diagram showing a configuration including a tag reader as a detecting unit.

As the detecting unit which detects the radiation image capturing device 1 brought into the image capturing room Ra or the front room Rb and which notifies the cassette ID to the console 58, instead of using the cradle 55 as in the present embodiment or together with the cradle 55, for example, a tag reader 60 can be provided near a door of the front room Rb as shown in FIG. 12.

In this case, a tag not shown such as an RFID (Radio Frequency Identification) tag is included in the radiation image capturing device 1 in advance and the unique information such as the cassette ID, etc. of the radiation image capturing device 1 is stored in the tag.

Then, when the radiation image capturing device 1 is brought into the image capturing room Ra or the front room Rb passing near the tag reader 60, the tag reader 60 can read the information such as the cassette ID, etc. from the tag of the radiation image capturing device 1 and notify the cassette ID to the console 58.

As described above, when the tag reader 60 is used as the detecting unit, it is possible to detect when the radiation image capturing device 1 is brought into the image capturing room Ra and when the radiation image capturing device 1 is brought out of the image capturing room Ra, which is preferable. In this case, it is possible to double check at least when the radiation image capturing device 1 is brought into the image capturing room Ra with the tag reader 60 and the cradle 55. When only the tag reader 60 is used as the detecting unit, for example, the cradle 55 can be used for simply charging of the radiation image capturing device 1.

As shown in FIG. 1, the front room (also called an operation room, etc.) Rb is provided with an operation table 57 of the radiation generating device including an exposure switch 56, etc. to instruct to the radiation source 52 to start emission of radiation.

In the present embodiment, the console 58 is provided in the front room Rb and includes a computer, etc. where a CPU, a ROM, a RAM, an input/output interface and the like not shown are connected through a bus. A predetermined program is stored in the ROM and the console 58 reads the necessary program, expands the program in the work region of the RAM and performs various processing according to the program.

The console 58 is provided with a display unit 58a including a CRT (Cathode Ray Tube), LCD (Liquid Crystal Display), etc. and an input unit, etc. which is not shown such as a keyboard or mouse is connected to the console 58. A storage unit 59 including a hard disk, etc. is connected to the console 58. Although illustration is omitted, other computers, external devices such as an imager which records a radiation image based on the image data output from the console 58 on an image recording medium such as film and outputs the image are also connected to the console 58 through a LAN (Local Area Network).

As described above, when the radiation image capturing device 1 brought into the image capturing room Ra is inserted and the cassette ID, etc. of the radiation image capturing device 1 is transmitted through the cradle 55 and the base station 54, the console 58 stores the cassette ID in the storage unit 59 and acknowledges and manages that the radiation image capturing device 1 with the above cassette ID is brought into the image capturing room Ra or the front room Rb.

As described above, when a signal showing that the mode is the image capturing possible mode is transmitted with the cassette ID from the radiation image capturing device 1, if the information showing the mode stored corresponded with the cassette ID stored in the storage unit 59 is the information showing the image capturing possible mode, the console 58 leaves the information as is, and if the information showing the stored mode is the information showing the sleep mode, the console 58 newly corresponds the information showing the image capturing possible mode to the cassette ID and overwrites and store the information.

When a signal showing that the mode is the sleep mode is transmitted with the cassette ID from the radiation image capturing device 1, if the information showing the mode stored corresponded with the cassette ID stored in the storage unit 59 is the information showing the sleep mode, the console 58 leaves the information as is, and if the information showing the stored mode is the information showing the image capturing possible mode, the console 58 newly corresponds the information showing the sleep mode to the cassette ID and overwrites and stores the information.

In this way, the console 58 acknowledges and manages whether the present mode of the radiation image capturing device 1 is either the image capturing possible mode or the sleep mode.

As described above, when the cassette ID of the radiation image capturing device 1 and the bucky ID are transmitted from the bucky device 51 where the radiation image capturing device 1 is connected to the connector 51b, the console 58 stores the bucky ID corresponded to the cassette ID stored in the storage unit 59.

When the CR cassette is loaded into the bucky device 51 and the barcode information of the CR cassette and the bucky ID are transmitted from the bucky device 51, the barcode information and the bucky ID are stored in the storage unit 59 corresponded to each other.

When the connection between the radiation image capturing device 1 and the connector 51b is released, the corresponding relation between the cassette ID of the radiation image capturing device 1 and the bucky ID stored in the storage unit 59 is released, and only the cassette ID is stored.

As described above, when the radiation image capturing device 1 is used loaded into the bucky device 51, the console 58 acknowledges and manages which radiation image capturing device 1 is loaded or not loaded into which bucky device 51. When the CR cassette is loaded into the bucky device 51, the console 58 acknowledges and manages which CR cassette is loaded into which bucky device 51.

It is possible to register in advance image capturing order information setting information necessary to perform predetermined radiation image capturing for each patient in a HIS (Hospital Information System) or RIS (Radiology Information System).

For example, as shown in the example of FIG. 13, the image capturing order information includes, "patient ID" P2, "patient name" P3, "sex" P4, "age" P5, "department" P6 as patient information and "capturing portion" P7, "capturing direction" P8 as capturing conditions. The present embodiment is provided with item "bucky ID" P9 as information of whether or not to perform image capturing in a state where the radiation image capturing device 1 is loaded into the bucky device 51 and when the image capturing device 1 is loaded into the bucky device 51, the bucky ID is described.

In the example shown in FIG. 13, the bucky ID "001" and "002" each show the bucky device 51A for image capturing in a standing position and the bucky device 51B for image capturing in a lying position. The bucky ID "003" shows that the radiation image capturing device 1 is used in a state by itself without loading into the bucky device 51. The bucky ID is "003" when the radiation image capturing device 1 is used in a state by itself without loading into the bucky device 51 because if the bucky ID is blank when the radiation image capturing device 1 is used in a state by itself, it is difficult to distinguish from when description is forgotten. Therefore, other display methods which show that the radiation image capturing device 1 is used in a state by itself can be employed and the display method is suitably determined. Instead of the bucky ID, three types of icons each showing the standing position bucky, the lying position bucky, and use by itself can be prepared, and an icon can be displayed corresponded to each image capturing order. In such configuration, the technologist, etc. can easily confirm by sight which capturing device to be used before image capturing, and mistakes hardly occur.

"Capturing order ID" P1 is automatically assigned to each image capturing order information in the order that the image capturing order is registered.

The content of the patient information and the capturing condition written in the image capturing order information is not limited to the above, and for example, it is possible to include information such as birthday of the patient, number of times of examination, amount of radiation, whether the patient is fat or thin, and the like. The example below describes a plurality of pieces of image capturing order information registered for each patient.

With the operation by the operator such as the radiation technologist, etc., when each piece of image capturing order information is registered in the console 58 itself, the console 58 accesses to the storage unit 59 where each piece of image capturing order information is stored. When each piece of image capturing order information is registered in the RIS or HIS, the console 58 obtains each piece of necessary image capturing order information from the RIS or the HIS.

In this case, the necessary image capturing order information can be obtained from the storage unit 59 or other computer with a suitable method such as the operator inputting in the console 58 the name of the patient, the patient ID, etc. of the image capturing to be performed, reading the barcode described in the image capturing request brought from the patient with a reading device to be input to the console 58, or when the capturing date is specified in the image capturing order information, inputting the capturing date in the console 58.

Then, as shown in FIG. 14, when the capturing order information is obtained, the console 58 displays a list of each piece of image capturing order information as the selection screen H1 on the display unit 58a of the console 58.

In the present embodiment, an image capturing order information display field h11 is provided in the selection screen H1 to display the list of each piece of image capturing order information. On the left side of the image capturing order information display field h11, a selection button h12 to select the image capturing order information to be captured is provided corresponding to each piece of image capturing order information. On the bottom side of the image capturing order information display field h11, an enter button h13 and a return button h14 are provided.

Then, for example, the operator clicks the selection button h12 and selects four pieces of image capturing order information regarding the patient "A". When the enter button h13 is clicked, the console 58 displays a screen H2 as shown in FIG. 15 on the display unit 58a.

In other words, the console 58 displays on the display unit 58a the icons I1 to I4 corresponding to each piece of selected image capturing order information in an order from a small number of the capturing order ID (see P1 of FIG. 14, etc.), in other words in the order of registration.

Basically, the display is based on the order of registration. However, when there is a predetermined rule in the facility such as to capture a string of portions from the head to the heel, the order can be rearranged to an order from top (head) to bottom (heel) or from bottom (heel) to top (head). When there is an image capturing order of both left and right portions such as the hand, leg, etc., in order to prevent mixing between the left and the right, the order can be rearranged to an order based on a condition of image capturing from the left or capturing from the right.

In FIG. 15, each icon I1 to I4 is displayed on the screen H2 aligned from the left side in a left and right direction, however, the alignment is not limited to the above, and for example each icon I1 to I4 can be displayed aligned from the upper side in an upper and lower direction. The method of display of each icon I1 to I4 is suitably set.

The icons I1 to I4 are aligned in the registered order. However, when image capturing order information with a different patient ID (see P3 of FIG. 14, etc.) or different department (see P6) is included in each selected image capturing order information, the icons I corresponding to the image capturing order information with the same patient or department can be displayed adjacent to each other regardless of the order of registration.

As described later, as the simplest case, the present embodiment describes when only one radiation image capturing device 1 is brought into the image capturing room Ra. However, first, the icon I displayed on the display unit 58a of the console 58 is described. For the purpose of description, as a typical case, the example describes when a plurality of radiation image capturing devices 1 are already brought into the image capturing room Ra and at least one radiation image capturing device 1 among those brought in is already loaded into a bucky device.

As shown in FIG. 15, in the present embodiment, the icons I1 to I4 each display capturing number such as "KM-0001", capturing portion (P7) and capturing direction (P8) such as "abdomen region front face P→A", whether a bucky device 51 such as "lying position" is used, type of bucky device 51 to be used, and the like.

In the example shown in FIG. 15, a horizontally long rectangle is displayed in the display portion Ia in the icon I1 for the icon I corresponding to the image capturing order information (see FIG. 14, etc.) of the capturing order ID "001" which uses the bucky device 51 for image capturing in a lying position. A vertically long rectangle is displayed in the display portion Ia of the icon I for the icons I2 and I3 corresponding to each piece of image capturing order information of the capturing order ID "002" and "003" which use the bucky device 51 for image capturing in a standing position. A figure in a shape of a perspective view of the radiation image capturing device 1 is displayed in the display portion Ia of the icon I for the icon I4 corresponding to the image capturing order information of the capturing order ID "004" which does not use the bucky device 51.

When the use of the bucky device 51 for image capturing in a standing position or image capturing in a lying position or use of the radiation image capturing device 1 in a state by itself is displayed in the display portion Ia of the icon I, instead of a rectangle or a figure in a perspective view as described above, it is possible to employ suitable measures such as display which is easy for the radiation technologist to understand.

In the present embodiment, when the icons I1 to I4 are displayed, the console 58 refers to the bucky ID corresponded to the cassette ID stored in the storage unit 59 and in the display portion Ib of the icon I of the image capturing order information using the bucky device 51, the console 58 displays the cassette ID of the radiation image capturing device 1 loaded into the bucky device 51 at present and the size, resolution, etc. of the radiation image capturing device 1 as shown in FIG. 15.

In order to change the setting to use the bucky device 51 different from the bucky device 51 set in each icon I1 to I4 or it is desired to perform image capturing in a state of the radiation image capturing device 1 by itself without the bucky device 51 (or vice versa), for example, it is possible to move the cursor on the screen H2 to the display portion Ia showing "standing position" or "lying position" in the icon I and to click the right mouse button to display a pop-up window, so that it is possible to select and change the item to the bucky device 51 described in the window or to not use the bucky device 51.

Figure 16:
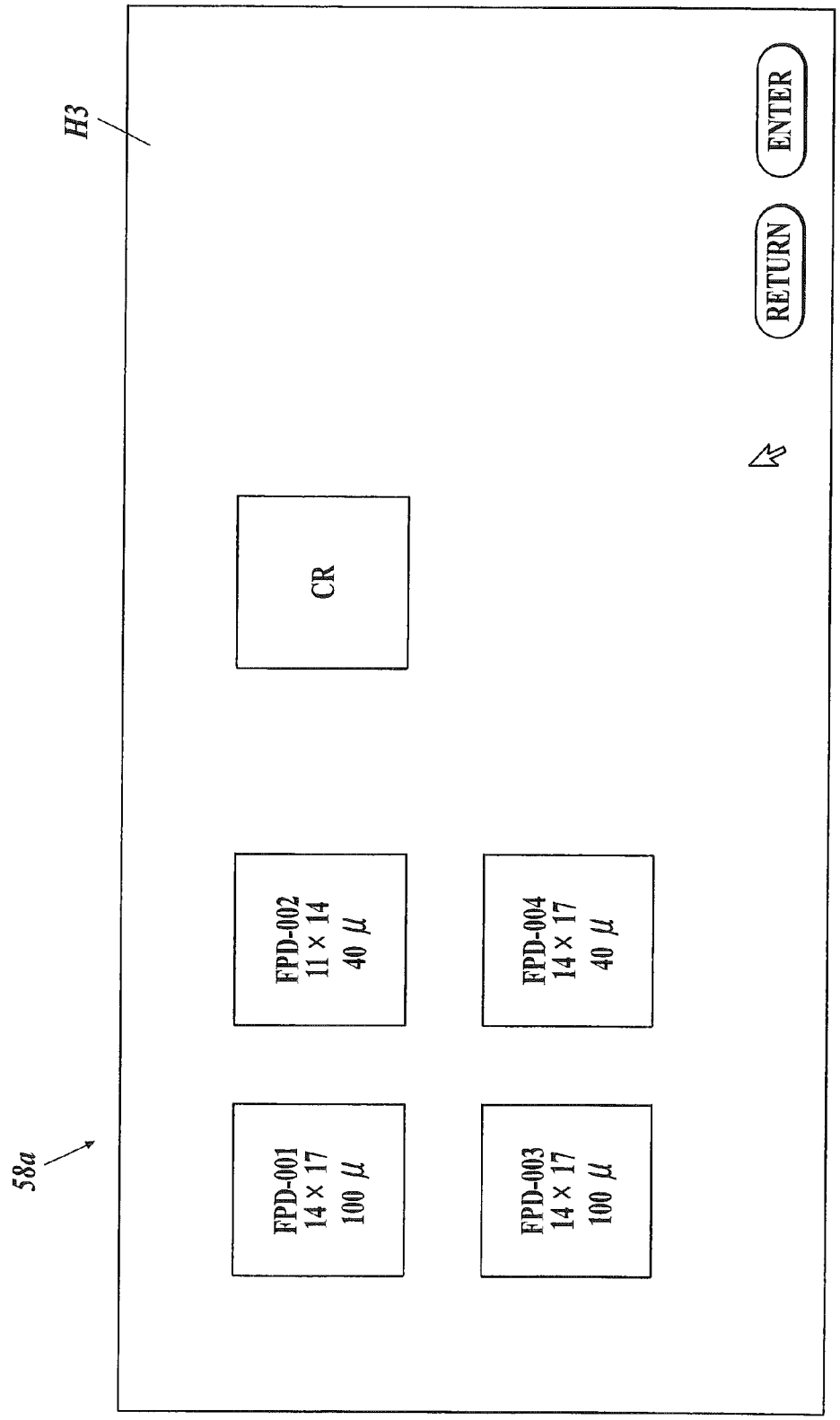
FIG. 16 is a diagram showing an example of a selection screen to select the portable radiation image capturing device and the CR cassette.

In order to change the radiation image capturing device 1 set in each icon I1 to I4, for example, it is possible to move the cursor on the screen H2 to the display portion Ib in the icon I and to click the right mouse button to display a selection screen H3 as shown in FIG. 16, so that it is possible to suitably select and change to the radiation image capturing device 1 after change from each icon group showing various radiation image capturing devices 1.

In order to change any of the radiation image capturing devices 1 set in each icon I1 to I4 to the CR cassette, for example, similar operation can be performed to display the selection screen H3 as shown in FIG. 16 and to click the icon displaying "CR" to change the setting.

Such format can be employed without providing a CR cassette identification information reading unit (barcode reader) in each bucky device 51 and is desirable. The operator such as the radiation technologist, etc. can change the desired image capturing order information from the radiation image capturing device format (FPD format) to the CR format in the front room Rb where the console 58 is provided. When the identification information of the CR cassette is input using the CR cassette identification information reading unit (barcode reader) provided in the console 58 in a state where the desired image capturing order information is selected, the setting can be changed automatically from the FPD format to the CR format.

When the reading device of the CR cassette is connected to the console 58 in a relation of 1:1, since the read image data is transmitted to the console 58 for each cassette loading, it is possible to only perform the switching operation to the CR on the selection screen H3 and to not perform the input of CR cassette identification information.

When the operation to change from the FPD to the CR is performed on the console 58 of the front room Rb, but the radiation image capturing device 1 is used in the actual image capturing accidentally, since the radiation emission synchronization signal is not transmitted from the console 58 to the radiation image capturing device 1, the radiation image capturing device 1 basically does not perform reading operation. However, when the radiation image capturing device 1 itself includes a radiation emission detecting unit, the reading operation is performed.

In this case, the emission amount is the setting for CR, therefore the amount becomes an excess amount as a whole. However, different from analog film, the image may be recovered by image processing. Therefore, in the above case, it is preferable that the image data transmitted from the radiation image capturing device 1 can be temporarily stored without corresponding to the image capturing order information on the console 58. Then, the gradation processing condition is corrected and when it is determined that the image can be provided for diagnosis, the image data on which image processing is performed again can be corresponded with the image capturing order information. If the image cannot be used for diagnosis even when image processing is performed, the mode is set to recapturing mode.

When setting of the bucky device 51 used is changed, the setting is changed so as to use or to not use the bucky device 51, the setting of the radiation image capturing device 1 is changed, or the setting is changed from the radiation image capturing device 1 to the CR cassette, the display of the changed icons I1 to I4 is changed to the changed content.

When the above change is performed, and for example, the operator attempts to perform image capturing without using the changed bucky device 51, the radiation image capturing device 1 or the CR cassette, it is possible to emit a warning by audio, etc. so that suitable measures are taken to use the suitable device or to perform image capturing under suitable conditions.

A gauge G showing the degree of progress of the processing displayed below each icon I1 to I4 shown in FIG. 15 is described later.

Next, the method of display in each icon I1 to I4 in the display unit 58a of the console 58 of the above configuration is described in detail. The operation of the radiation image capturing system 50 of the present embodiment is also described.

The present embodiment describes the simplest example which is to bring in only one portable radiation image capturing device 1 into the image capturing room Ra. Therefore, in the description of the present embodiment below, there is only one portable radiation image capturing device 1 in the image capturing room Ra.

Figure 17:
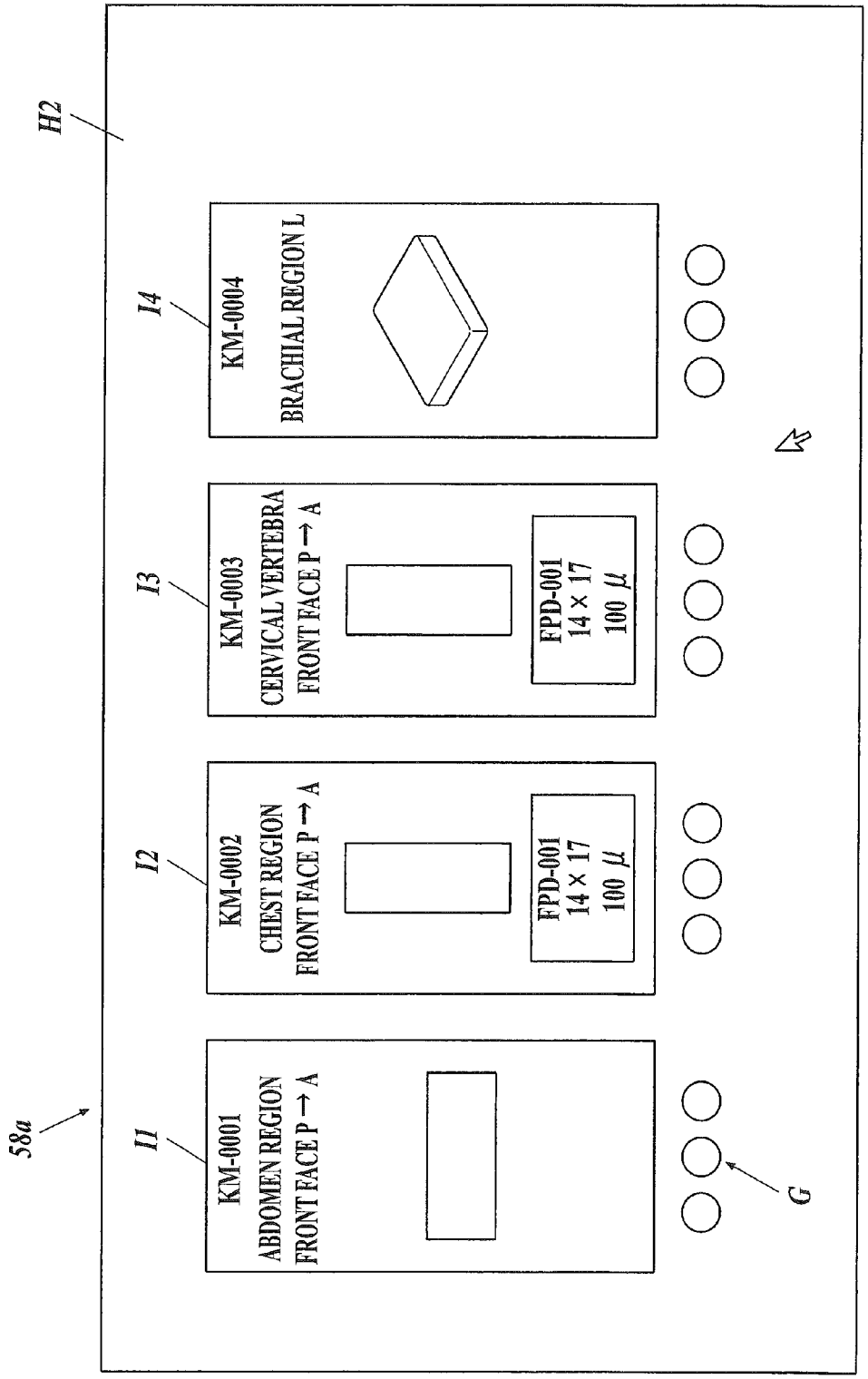
FIG. 17 is a diagram showing an example of a selection screen displayed on the display unit of the console when there is only one portable radiation image capturing device in the capturing room according to the first embodiment.

In the example described below, the radiation image capturing device 1 is already loaded into the bucky device 51A for image capturing in a standing position. Therefore, in this case, each icon I1 to I4 as shown in FIG. 17 is displayed on the screen H2 of the console 58.

Therefore, in this case, even if the right mouse button is clicked in the display portion Ib of the "FPD" in the icon I, only the radiation image capturing device 1 of the "FPD-001" is displayed on the selection screen H3 shown in FIG. 16.

In the present invention, the console 58 automatically selects one icon I among each icon I1 to I4 corresponding to each image capturing order information displayed on the display unit 58a and displays the selected icon I in a manner different from the other icons I.

Below, displaying an icon in a manner different from other icons is simply described as focusing to the icon I. When the focused icon I is illustrated, diagonal lines are added to the icon I.

As a method of focusing the icon I, for example, the icon I is basically displayed colored in a color similar to the base color of the screen H2 such as blue or black, whereas when the icon I is displayed focused, only the icon I may be displayed colored in red, yellow or the like. The focused icon I can also be displayed in a shape different from other icons I, the focused icon I can blink, the position of displaying the focused icon I on the screen H2 can be changed, the focused icon I can be displayed zoomed, and the like.

In the present invention, when the console 58 selects the icon I automatically, the icon I is selected focused according to the standard described below.

[Standard 1]

The icon I selected and focused is the icon I corresponding to the image capturing order information specifying the image capturing condition where image capturing can be performed without changing the present state or the image capturing can be performed by keeping the change to a minimum. The states considered are, the mode of each radiation image capturing device 1, the state of loading into the bucky device 51, the state of start and position of each radiation source 52, the position and direction of the radiation source 52A (see FIG. 1) or the like.

Therefore, when the operator performs image capturing based on the image capturing order information corresponded to the icon I which the console 58 focuses on, image capturing can be performed without loading the radiation image capturing device 1 into the bucky device 51, or without loading the radiation image capturing device 1 already loaded into a bucky device 51 to another bucky device 51 or by performing only minimum operation. Therefore, it is possible to achieve the effect of promptly performing image capturing.

Details of the standard 1 are suitably set according to the configuration of the radiation image capturing system 50 and the performance of each device. When the radiation image capturing device 1 and the radiation image capturing system 50 is configured as described above, for example, the relevant icon is automatically selected according to the following detailed standard [1-1], [1-2].

[1-1] When the radiation image capturing device 1 is loaded into the bucky device 51, the icon I selected and displayed focused is the icon I corresponding to the image capturing order information specifying image capturing in a state where the radiation image capturing device 1 is loaded into the bucky device 51.

[1-2] When the radiation image capturing device 1 is not loaded into the bucky device 51, the icon I selected and displayed focused is the icon I corresponding to the image capturing order information specifying image capturing in a state where the radiation image capturing device 1 is used by itself without loading into the bucky device 51.

The above standard [1-1] applies in a case such as when the radiation image capturing device 1 is loaded into the bucky device 51A for image capturing in a standing position, the radiation source 52A is facing the direction of the bucky device 51A for image capturing in a standing position. Moreover, even when the radiation source 52A is not facing the direction of the bucky device 51A for image capturing in a standing position, usually, instead of removing the radiation image capturing device 1 from the bucky device 51A for image capturing in a standing position and loading the radiation image capturing device 1 on the bucky device 51B for image capturing in a lying position, changing the emission direction of the radiation source 52A is a smaller degree of change and the burden of the operator can be reduced. Further, the start of image capturing is input on the console and the preparation of the radiation source is completed while actually moving to the image capturing room. Therefore, the image capturing can be finished soon.

With the above standard [1-2], when the image capturing is performed using the radiation image capturing device 1 in a state by itself without loading into the bucky device 51, the amount of operation by the operator between image capturing performed four times on one patient can be reduced (the operation of attaching and removing the radiation image capturing device 1 to and from the bucky device 51).

In a case of the above standard [1-2], even when the operator judges to first perform image capturing in which the radiation image capturing device 1 is loaded into the bucky device 51, the operator can select and focus an icon I different from the icon I selected from the console 58 according to the standard 3 described below.

[Standard 2]

When the radiation image capturing device 1 is not brought into the image capturing room Ra, or it is not possible to judge which icon I to focus according to the above standard (hereinafter such state is referred to as default), the console 58 selects and focuses the icon I first in order (the icon I1 displayed to the left in FIG. 15 and FIG. 17) from the icons I in which image capturing is not yet performed among the icons I1 to I4 displayed and arranged in a predetermined order such as in order of registration on the display unit 58a.

[Standard 3]

The reason the console 58 automatically selects and focuses the icon I is because the above effects can be achieved and it is to recommend selection of the icon I. This does not force the operator to perform image capturing based on the image capturing order information corresponding to the icon I which is selected and focused.

Therefore, when the operator desires to perform image capturing based on the image capturing order information other than the image capturing order information corresponding to the icon I which is focused, the operator can click a different icon I corresponding to the image capturing order information of the image capturing which is to be performed and select the icon I.

When the operator clicks and selects an icon I different from the focused icon I, the icon I selected by the operator is focused and the focus of the icon I automatically selected by the console 58 is released. Therefore, the icon I automatically selected by the console 58 is displayed returned to the original manner of display not focused similar to the other icons I.

When each icon I1 to I4 is displayed on the screen H2 as shown in FIG. 17, since the radiation image capturing device 1 is loaded into the bucky device 51A for capturing in a standing position at present, the console 58 selects the icon I2 or the icon I3 according to the above standard 1. Then, considering only the icon I2 and the icon I3 since the standard 2 is applied in a default state, the icon I2 is selected.

Figure 18:
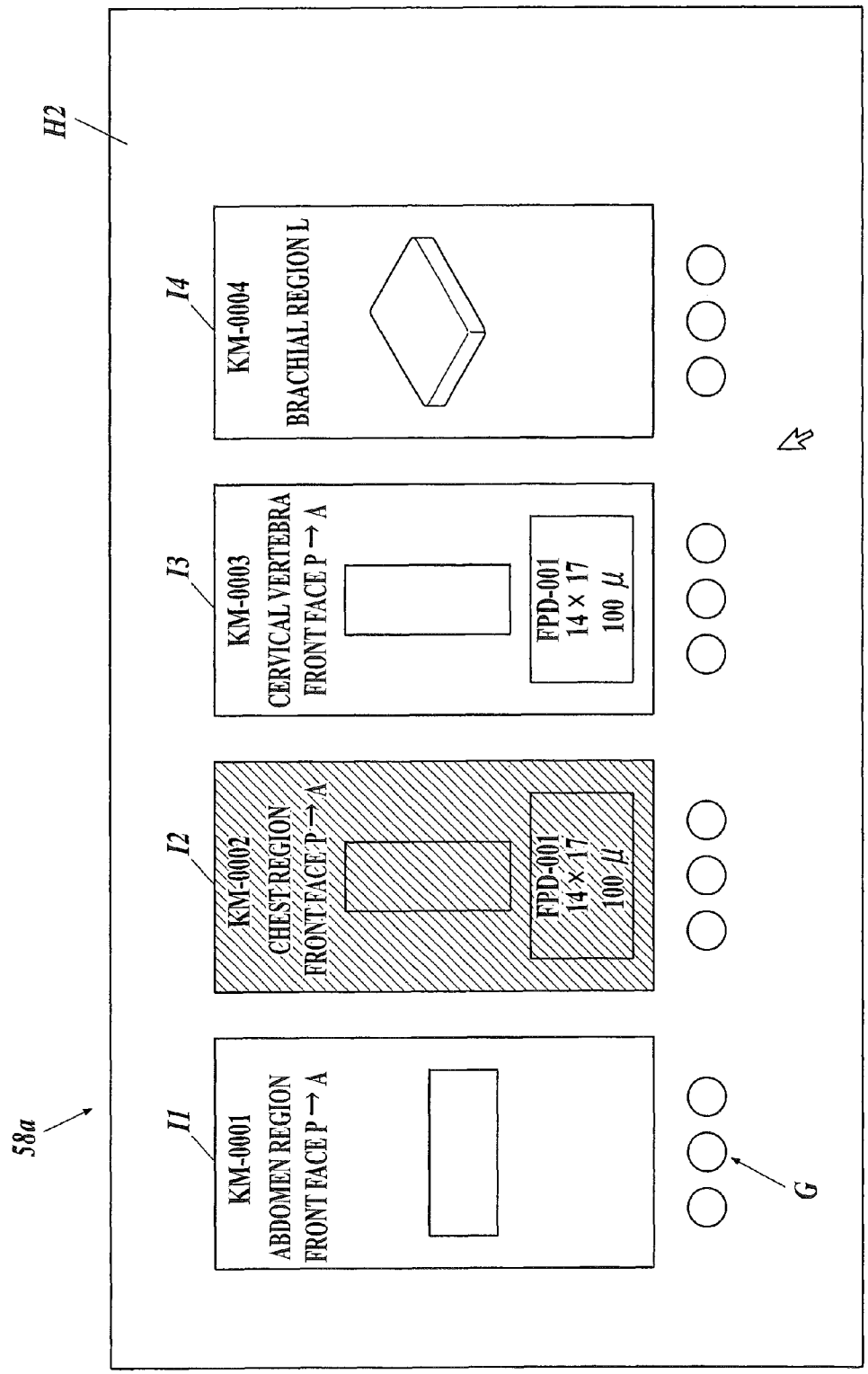
FIG. 18 is a diagram describing the icon I2 is focused in the selection screen shown in FIG. 17.

Therefore, as shown in FIG. 18, the icon I2 is selected, focused and displayed on the screen H2 of the display unit 58a of the console 58. Usually, when the icon I is focused and displayed, the first icon I in the order of display is focused. However, in the present invention, as shown in FIG. 18, regardless of the order of display, the icon I2 corresponding to the image capturing order information specifying the image capturing which can be performed fastest is focused.

When the selected icon I (icon I2 in FIG. 18) is focused and displayed, the console 58 immediately starts each device used in the image capturing to a predetermined state based on the image capturing order information corresponding to the icon I. In other words, in the example shown in FIG. 18, if the radiation source 52A is not started, the radiation source 52A is started, and if the radiation source 52A is not in a state to be able to emit radiation to the bucky device 51A for image capturing in a standing position, the radiation source 52A is moved to a predetermined position and the emission direction is changed.

When the radiation image capturing device 1 is in the sleep mode, a waking signal (wake-up signal, etc.) is transmitted to the radiation image capturing device 1 to perform processing as switching to the image capturing possible mode.

When each device is started as described above, the operator can promptly perform image capturing after moving to the image capturing room Ra without loading into the bucky device 51 the radiation image capturing device 1 which is not yet loaded into the bucky device 51, without loading the radiation image capturing device 1 loaded into the bucky device 51 to another bucky device 51, or by only performing minimum operation.

Therefore, the radiation image capturing system 50 is easy to use for an operator such as a radiation technologist, etc. and it is possible to perform efficient radiation image capturing.

The operator such as the radiation technologist, etc. may not perform the above operation on the screen H2 of the display unit 58a of the console 58 and for example, may bring in a new radiation image capturing device 1 into the image capturing room Ra, load the radiation image capturing device 1 into the cradle 55, notify to the console 58 that the new radiation image capturing device 1 is brought in, and press the selection switch 38 of the radiation image capturing device 1, or load the new radiation image capturing device 1 into the bucky device 51 or bring in a CR cassette and load the CR cassette into the bucky device 51.

In such case, since each cassette ID, barcode information, etc. is transmitted to the console 58, the console 58 can acknowledge the above operation is performed. Then, when such operation is performed, it is possible to judge that it is the intension of the operator to perform image capturing using the newly brought in radiation image capturing device 1 or the CR cassette.

According to the present embodiment, in this case, when the cassette ID, barcode information, etc. is transmitted, the console 58 stores and registers the above in the storage unit 59, and switches the icon I focused on the screen H2 of the display unit 58*a* and the display of the icon I according to the information of the newly transmitted cassette ID, barcode information, etc.

In other words, in the example shown in FIG. 18, when the operator presses the selection switch 38 of the radiation image capturing device 1 newly brought into the image capturing room Ra, the console 58 switches the focused icon I without operation by the operator on the display unit 58*a* from the icon I2 automatically selected and focused by the console 58 to the icon I4 corresponding to the image capturing order information specifying performing image capturing in a state where the radiation image capturing device 1 is used by itself without loading into the bucky device 51.

When the operator loads the new radiation image capturing device 1 into the bucky device 51B for image capturing in a lying position, the console 58 switches the focused icon I from the icon I2 to the icon I1 corresponding to the image capturing order information specifying performing image capturing in a state where the radiation image capturing device 1 is loaded into the bucky device 51B for image capturing in a lying position.

When the operator loads the CR cassette into the bucky device 51B for image capturing in a lying position, the console 58 switches the focused icon I from the icon I2 to the icon I1 corresponding to the image capturing order information specifying performing image capturing using the bucky device 51B for image capturing in a lying position and switches the display of the display portion Ib of "FPD" in the icon I1 to display of barcode information, size, etc. of the CR cassette.

When the operator removes the radiation image capturing device 1 from the bucky device 51A for image capturing in a standing position and loads the CR cassette instead, the icon I which the console 58 focuses does not change from the icon I2. However, the display of the display portion Ib of the "FPD" in the icon I2 is switched to the display of the barcode information, size, etc. of the CR cassette.

When the focused icon I is switched as described above, the corresponding image capturing order information is also switched, and when the display of the icon I is switched from the radiation image capturing device 1 to the CR cassette, the capturing condition needs to be changed. Therefore, when the image capturing order information or the capturing condition is switched, the console 58 switches the focused icon I and the display of the icon I and simultaneously stops the start of each device already started and starts and controls each device used in the image capturing to a predetermined state based on the capturing condition after change.

As described above, in the radiation image capturing system 50 of the present embodiment, according to the intension of the operator such as the radiation technologist, etc., the focused icon I and the display of the icon I is automatically switched and each device is automatically started to a predetermined state. With this, the radiation image capturing system 50 is easy to use for the operator.

While the radiation source 52, the radiation image capturing device 1 etc., are started based on the changed capturing condition when the image capturing order information corresponding to the focused icon I (including the icon I focused after change) is switched or the radiation image capturing device 1 is switched to the CR cassette, for example, the operator such as the radiation technologist, etc., can guide the patient into the capturing room Ra and allow the patient to take a predetermined posture in a predetermined position.

Then, the operator moves to the front room Rb and by operating the exposure switch 56 when the image capturing can be performed, radiation is emitted from the radiation source 52 to perform the radiation image capturing.

When the radiation image capturing is performed, as described above, the control unit 22 of the radiation image capturing device 1 reads the image data D from each radiation detecting element 7 and stores the image data D in the storage unit 23. In the present embodiment, based on each piece of image data D read from each radiation detecting element 7, the control unit 22 thins out each piece of image data D at a predetermined percentage and automatically creates the thinned out data Dt for preview. The control unit 22 transmits the thinned out data Dt with the cassette ID attached through the antenna device 41 and the bucky device 51 to the console 58.

In the present embodiment, after the thinned out data Dt is transmitted to the console 58, the control unit 22 attaches the cassette ID to the image data D which is the basis of creating the thinned out data Dt and automatically transmits the above to the console 58. As described above, it is possible to transmit the image data D without creating the thinned out data Dt and it is possible to transmit the image data D when there is an instruction to transmit the image data D from the console 58, etc.

The control unit 22 calculates the offset correction value O based on the dark reading value d read in the dark reading processing performed at a predetermined timing, attaches the cassette ID to the calculated offset correction value O and automatically transmits the above to the console 58.

When the radiation image capturing is performed using the CR cassette, after image capturing, the operator, etc., moves the CR cassette to the reading device outside the image capturing room Ra and performs the reading processing of the image data D. Then, the image data D is transmitted with the barcode information of the CR cassette from the reading device to the console 58.

When the thinned out data Dt, etc. is transmitted from the radiation image capturing device 1 or when the image data D captured by the CR cassette is transmitted from the reading device, the console 58 creates the preview image based on the transmitted thinned out data Dt or the image data D.

Figure 19:
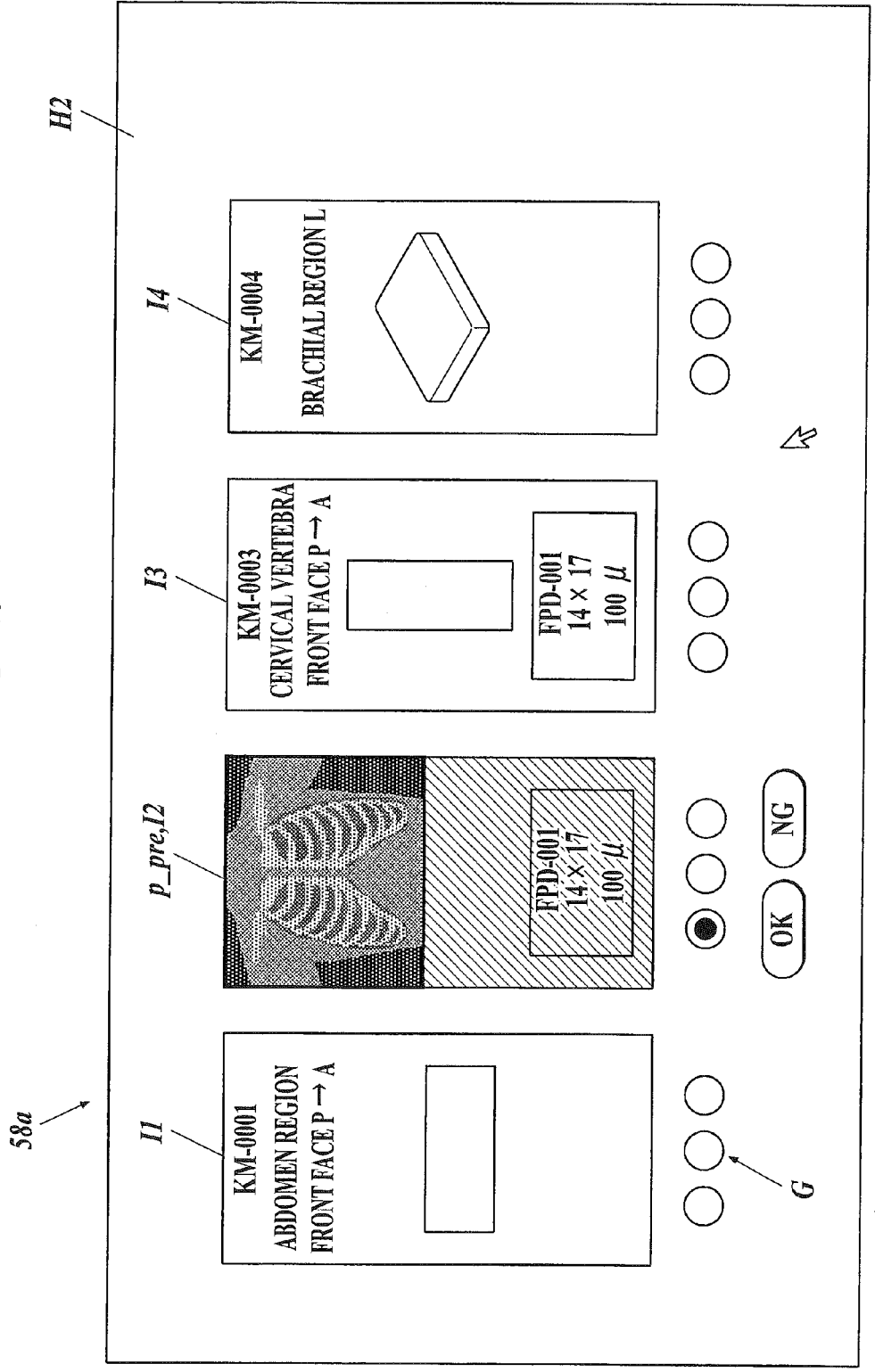
FIG. 19 is a diagram describing a preview image is displayed instead of the icon I2 shown in FIG. 18.

Then, as shown in FIG. 19, the console 58 displays the created preview image p_pre instead of the icon I2 in a position where the icon I2 displayed focused was displayed on the screen H2 of the display unit 58*a*. With the preview image p_pre, it is possible to confirm whether the position of the patient at the time of image capturing is good or bad and it is possible to start preparation of recapturing according to necessity.

The console 58 displays the preview image p_pre and also displays with color the first area (in the present embodiment, far left gauge) of the gauge G showing the degree of progress of the string of image processing for the image provided in diagnosis such as gradation processing on the image data D (in other words, raw data) displayed below the preview image p_pre (previously icon I2).

Then, based on the image data D and the offset correction value O transmitted from the radiation image capturing device 1, the console 58 performs various image processing such as offset correction, gain correction, logarithmic conversion processing, etc. on the image data D and generates the final radiation image p for diagnosis on which image processing is performed.

In this case, although illustration is omitted, in the present embodiment, as the degree of progress of the image processing on the image data D advances, the image on which image processing is in progress is suitably displayed in the position where the preview image p_pre was displayed on the screen H2 and the second area (in the present embodiment, center gauge) of the gauge G showing the degree of progress of processing is displayed with color to show that the image processing is being performed.

When the third area (in the present embodiment, far right gauge) of the gauge G is colored, the preview image p_pre is overwritten and displayed by the radiation image p. The radiation technologist, etc. acknowledges that the image is overwritten by the radiation image p by the third area being colored, and confirms whether the contrast is suitable, in other words, whether the emitted radiation is suitable based on the image p and performs preparation of recapturing according to necessity. Modification of the gauge G showing the degree of progress of the processing is possible such as showing the change in the length of the bar and it is also possible to not display the gauge G.

In the present embodiment, as shown in FIG. 19, the buttons "OK" and "NG" are displayed below the preview image p_pre or the radiation image p. The operator clicks the "OK" button when the image capturing is normal and recapturing is not necessary and clicks the "NG" button when the image capturing is not normal and recapturing needs to be performed. The confirmation from the operator is obtained as described above.

When the operator views the preview image p_pre and the radiation image p and judges that recapturing is not necessary and clicks the "OK" button, the console 58 displays a different icon I focused. This processing is described later.

When the operator views the preview image p_pre and the radiation image p and judges that recapturing is necessary and clicks the "NG" button, the console 58 returns the display of the preview image p_pre and the radiation image p to the display of the original icon I2 and cancels the display of the "OK" button and the "NG" button on the screen H2 or does not allow the "OK" button and the "NG" button to be clicked. The display of the gauge G is also returned to the original form.

Then, the transmitted thinned out data Dt and the image data D is deleted and the radiation image capturing device 1 is instructed to delete the image data D, etc. obtained in the radiation image capturing and stored in the storage unit 23. The image data D, etc. obtained in the radiation image capturing is not necessary.

When the operator clicks the "OK" button, the console 58 does not return the display of the preview image p_pre or the radiation image p to the display of the original icon I2 and maintains the display of the preview image p_pre and the radiation image p, and cancels the display of the "OK" button and the "NG" button from the screen H2 or does not allow the "OK" button and the "NG" button to be clicked.

Then, the console 58 does not allow the icon I2 to be selected again even when the operator moves and clicks the cursor on the preview image p_pre or the radiation image p, similar to when the icon I is selected.

This is because there is no need to select again image capturing that is already performed normally (in other words, image capturing judged that recapturing is not necessary) and it is possible to prevent trouble such as image data D, etc. already obtained being deleted by selecting the image capturing performed normally again. When for some reason there is a necessity to perform radiation image capturing again based on the image capturing order information, and in case the image data D, etc. already obtained needs to be deleted, it is possible to delete the image data D, etc. already obtained for the image capturing order information by performing special operation and in this case suitable method of operation is set.

Figure 20:
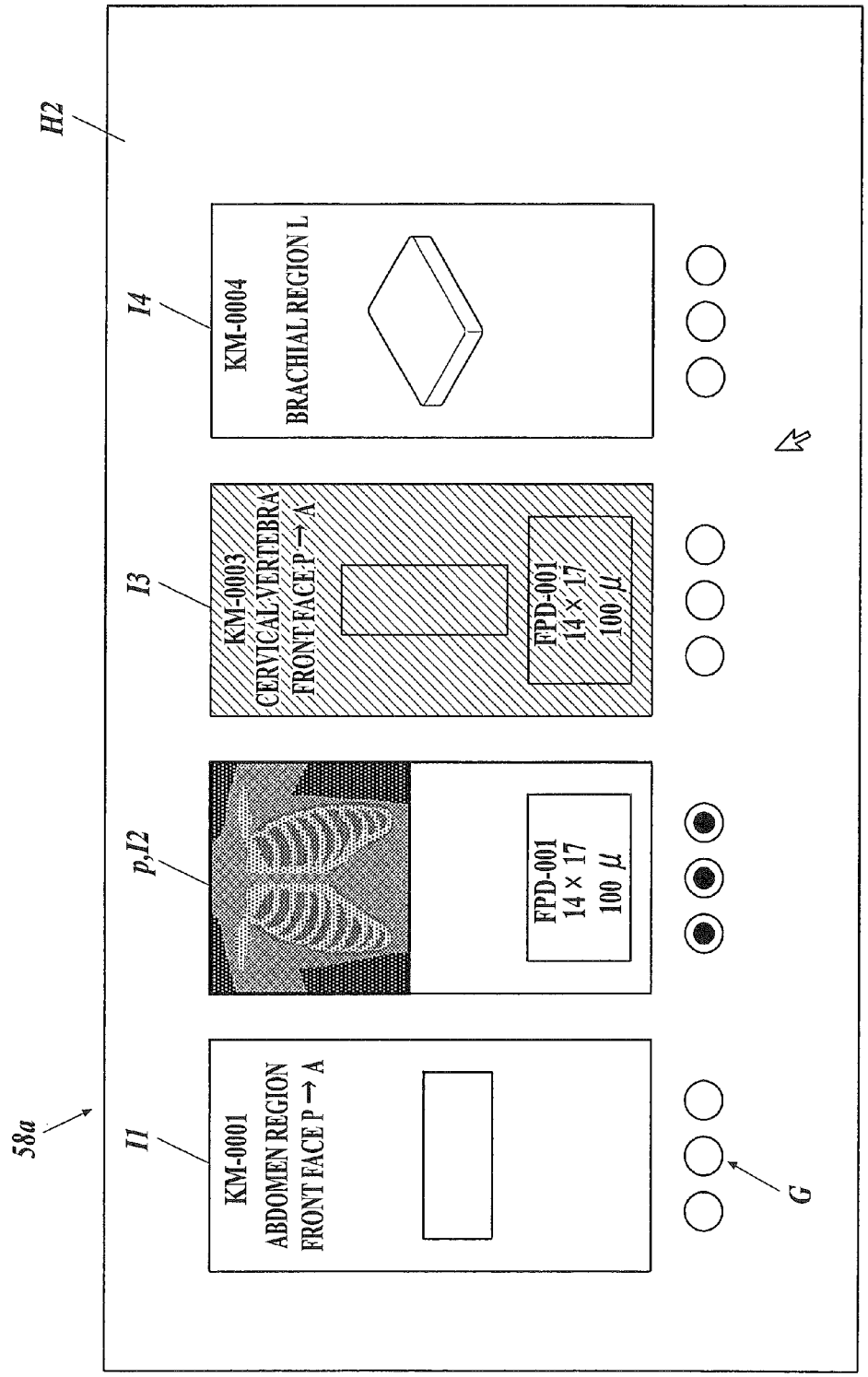
FIG. 20 is a diagram describing the generated radiation image is displayed in the position where the preview image is displayed in FIG. 19.

Then, when the final radiation image p is generated, as shown in FIG. 20, the generated radiation image p is displayed in the position where the image while the image processing is in progress is displayed on the screen H2 (in other words, the position where the preview image p_pre is displayed) and the third area (in the present embodiment, right gauge) of the gauge G showing the degree of progress of the processing is displayed with color and shows that each processing to the generating processing of the radiation image p is complete.

The console 58 stores the generated radiation image p corresponded with the image capturing order information corresponding with the original icon I2 in the storage unit 59. The image data D before image processing (in other words, raw data) can be stored in the storage unit 59 corresponded to the image capturing order information.

As described above, the radiation image capturing system 50 of the present embodiment focuses the icon I selected by the console 58 or accurately focuses the icon I selected by the operator such as the radiation technologist, etc. Alternatively, the focused icon I and the display of the icon I is accurately switched according to the intension of the operator.

Then, the radiation image capturing is performed based on the image capturing order information corresponding to the icon I displayed focused or based on the image capturing order information in which information such as the bucky device 51 or the radiation image capturing device 1, etc. to be used is changed from the above image capturing order information. The bucky device 51, etc. specified in the image capturing order information can be changed, however, at least the capturing order ID (see FIG. 13 and FIG. 14) cannot be changed.

Then, the image data D transmitted from the radiation image capturing device 1 or the reading device which reads the image data D from the CR cassette is corresponded with the image capturing order information corresponding to the icon I displayed focused. Therefore, the image data D obtained by the image capturing based on the image capturing order information corresponding to the icon I displayed focused can be automatically and accurately corresponded to the image capturing order information.

Therefore, it is possible to accurately prevent the image data D obtained in the image capturing based on the image capturing order information being corresponded to different image capturing order information. From the above point also, the radiation image capturing system 50 is easy to use for the operator and efficient radiation image capturing can be performed.

As shown in FIG. 19, the "OK" button and the "NG" button are displayed below the preview image p_pre and when the operator clicks the "OK" button as the recapturing being not necessary, the processing of the preview image p_pre is performed as described above.

The console 58 then selects and focuses the next icon I according to the above standards.

Figure 21:
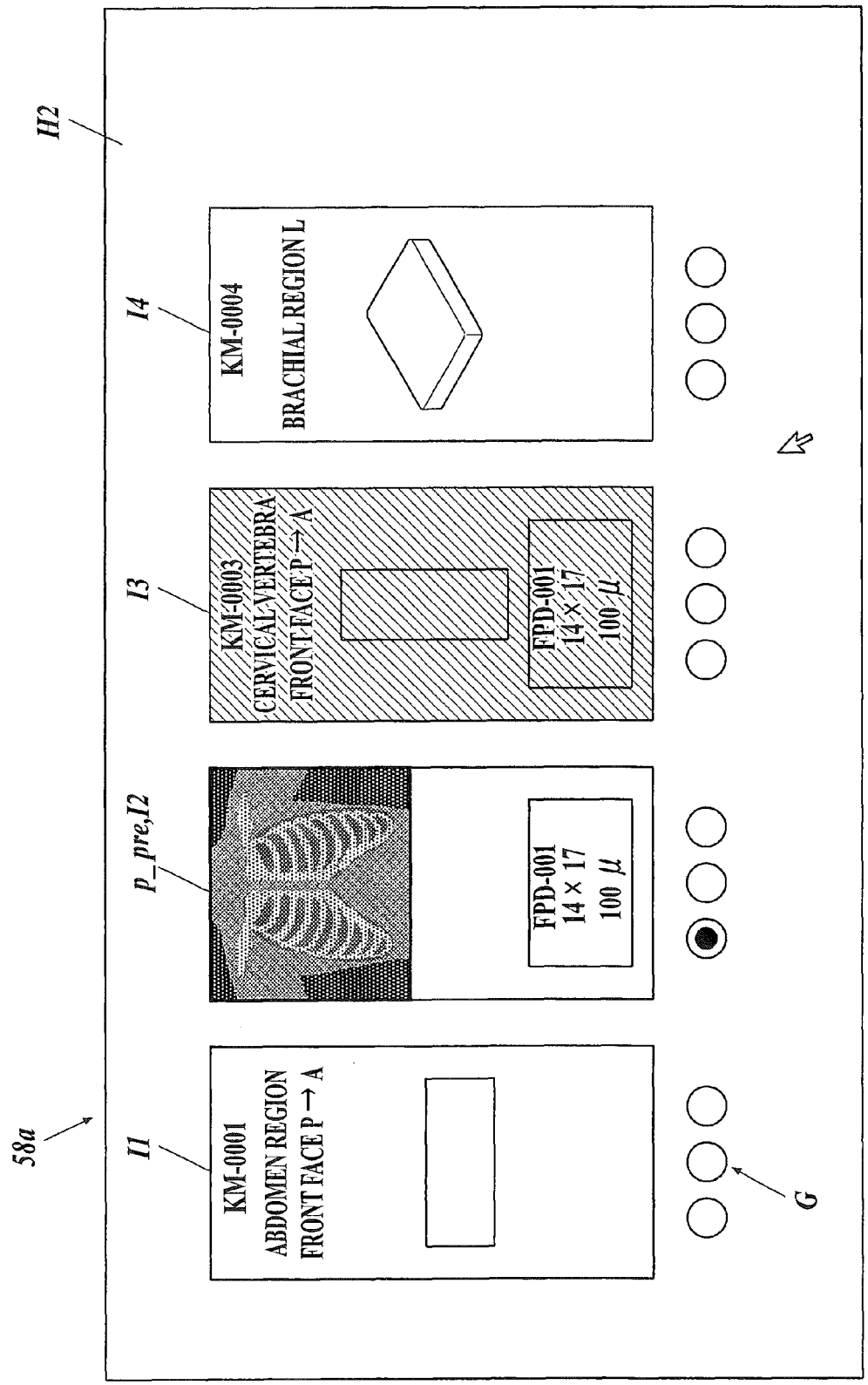
FIG. 21 is a diagram describing the icon I3 is selected and focused after the state shown in FIG. 19.

Specifically, in the example shown in FIG. 19, since the radiation image capturing device 1 is loaded into the bucky device 51A for image capturing in a standing position, as shown in FIG. 21, according to the above standard 1, the console 58 selects and focuses the icon I3 corresponding to the image capturing order information in which there is no need to change the loading state of the radiation image capturing device 1 on the bucky device 51 and the image capturing can be performed without changing the starting state, the position, the direction, etc. of each radiation source 52A from the present state.

As described above, in the radiation image capturing system 50 of the present embodiment, instead of the icon I1 of the default state, the automatically selected and focused icon I2 corresponds to the image capturing order information which specifies the capturing conditions where image capturing can be performed without changing the present state of the mode of each radiation image capturing device 1, the loading state of the radiation image capturing device 1 on the bucky device 51, the starting state of each radiation source 52, the position and direction of the radiation source 52A, and the like.

In this case, the image capturing based on the image capturing order information corresponding to the icon I2 has just been performed and the radiation image capturing device 1 is in the image capturing possible mode. Therefore, it is not necessary to transmit a waking signal from the console 58 to the radiation image capturing device 1. Moreover, the radiation source 52A is started and is in a state where it is possible to emit radiation to the bucky device 51 for image capturing in a standing position. However, when the amount of emitted radiation is changed, the tube voltage is changed to emit the amount.

Then, when the radiation image capturing is performed, the thinned out data Dt, etc. is transmitted from the radiation image capturing device 1 to the console 58. Similar to the above, based on the transmitted thinned out data Dt, etc. the console 58 creates and displays the preview image p_pre and generates and displays the radiation image p.

The console 58 displays the preview image p_pre in the original position of the icon I3 and when the "OK" button is clicked, then, the next icon I is selected and focused according to the above standards.

In this case, the icons I which can be selected are icon I1 and icon I4. According to the above standard 1, the console 58 selects and focuses the icon I1. The reason for such selection is described below.

In other words, when the image capturing is performed based on the image capturing order information corresponding to the icon I4, the start of the radiation source 52A needs to be stopped and the portable radiation source 52B needs to be started. However, when the image capturing is performed based on the image capturing order information corresponding to the icon I1, only the position and the emission direction of the radiation source 52A already started need to be changed.

In the above case, when the icon I3 is selected, the next image capturing can be performed with the minimum change from the present state such as the loading state of each radiation image capturing device 1 on the bucky device 51, the starting state of each radiation source 52, the position and direction of the radiation source 52A and the like.

Therefore, when the image capturing is performed based on the image capturing order information corresponding to the icon I1 focused by the console 58, since the operator only needs to move the radiation image capturing device 1 from the bucky device 51A for image capturing in a standing position to the bucky device 51B for image capturing in a lying position. Therefore, the image capturing can be performed by only performing the minimum operation and the image capturing can be performed promptly. Therefore, the radiation image capturing system 50 is easy to use for the operator and the radiation image capturing can be performed efficiently.

As described above, even if the console 58 selects and focuses the icon I1, the operator can click the icon I4 to change the icon I displayed focused to the icon I4 when the operator judges to first perform image capturing based on the image capturing order information corresponding to the icon I4, in other words, to first perform image capturing by placing the radiation image capturing device 1 against the body of the patient or by inserting the radiation image capturing device 1 between the body of the patient and the bed.

The above example describes the simplest case where only one radiation image capturing device 1 is brought into the image capturing room Ra, and the radiation image capturing device 1 is already loaded into the bucky device 51A for image capturing in a standing position. A case where a plurality of radiation image capturing devices 1 are brought into the image capturing Ra in advance is described in the second embodiment.

When the only radiation image capturing device 1 in the image capturing room Ra is already loaded into the bucky device 51B for image capturing in a lying position, although illustration is omitted, on the screen H2 of the display unit 58a of the console 58, the console 58 displays with focus the icon I1 corresponding to the image capturing order information specifying the image capturing using the bucky device 51B for image capturing in a lying position.

When the only radiation image capturing device 1 in the image capturing room Ra is left in a state inserted in the cradle 55, or the radiation image capturing device 1 is pulled out of the cradle 55 but is not loaded into the bucky device 51A for image capturing in a standing position and the bucky device 51B for image capturing in a lying position on the screen H2 of the display unit 58a of the console 58, the console 58 displays with focus the icon I4 corresponding to the image capturing order information which specifies image capturing using the radiation image capturing device 1 by itself without loading into the bucky device 51.

Then, the console 58 automatically performs processing such as starting the radiation source 52 according to the image capturing order information corresponding to the icon I automatically selected by the console 58. When each device is started, as described above, the operator can promptly perform image capturing because image capturing can be performed without loading into the bucky device 51 the radiation image capturing device 1 which is not loaded into the bucky device 51, or without loading the radiation image capturing device 1 loaded into the bucky device 51 on another bucky device 51 or by performing only minimum operation.

The preview image p_pre and the radiation image p based on the thinned out data Dt, the image data D etc. obtained by performing image capturing are automatically displayed in the position of the icon I displayed focused and are automatically stored corresponded with the image capturing order information corresponding to the icon I displayed focused.

Therefore, in the above case, the radiation image capturing system 50 is easy to use for an operator such as the radiation technologist, etc. and efficient radiation image capturing is possible.

In the above case, when the operator such as the radiation technologist, etc. desires to perform image capturing based on the image capturing order information different from the image capturing order information corresponding to the icon I selected and focused by the console 58, the operator can click the different icon I or the operator can load the radiation image capturing device 1 in the capturing room Ra into the desired bucky device 51 so that the operator can suitably switch the icon I displayed focused to the icon I corresponding to the image capturing order information specifying the image capturing which the operator desires to perform.

Then, the console 58 automatically performs the processing such as start of the radiation source 52 according to the image capturing order information corresponding to the icon I which the operator switched to. Then, the preview image p_pre and the radiation image p based on the thinned out data Dt and the image data D, etc. obtained by the image capturing are automatically displayed in the position of the icon I displayed focused and are automatically stored corresponded with the image capturing order information corresponding to the icon I displayed focused.

Therefore, it is possible to switch the focused icon I according to the intension of the operator such as the radiation technologist. The image data D, etc. is stored accurately corresponded with the image capturing order information corresponding to the switched icon I. From this point also, the radiation image capturing system 50 is easy to use for the operator.

According to the radiation image capturing system 50 of the present embodiment, according to at least the standard 1, when the radiation image capturing device 1 is loaded into the bucky device 51, regardless of the order of display of the icon I corresponding to each piece of image capturing order information displayed on the display unit 58a, the console 58 displays with focus the icon I corresponding to the image capturing order information specifying image capturing in a state where the radiation image capturing device 1 is loaded into the bucky device 51.

When the radiation image capturing device 1 is not loaded into the bucky device 51, the console 58 displays with focus the icon I4 corresponding to the image capturing order information specifying the image capturing performed in a state where the radiation image capturing device 1 is not loaded into the bucky device 51.

Therefore, if the operator such as the radiation technologist, etc. performs image capturing based on the image capturing order information corresponding to the icon I which the console 58 displays with focus, the image capturing can be performed at least without changing the loading state of the radiation image capturing device 1 on the bucky device 51. Therefore, the radiation image capturing system 50 of the present embodiment is easy to use for the operator. Moreover, the radiation image capturing can be performed efficiently.

The console automatically determines the order of the image capturing in the most efficient order. However, after the image capturing is complete, when the image data is externally output, the output can be made in the original order in the image capturing order information. Therefore, there is no confusion in the order of display of the image on the external PACS (Picture Archiving and Communication System) system.

[Second Embodiment]

As described above, the first embodiment describes the simplest case where only one radiation image capturing device 1 is brought into the image capturing room Ra. The second embodiment describes bringing in a plurality of radiation image capturing devices 1 in the image capturing room Ra in advance.

As described in the first embodiment, at the start of image capturing, only one radiation image capturing device 1 is brought into the image capturing room Ra. However, in many cases as the image capturing progresses, a new radiation image capturing device 1 is brought into the image capturing room Ra and a plurality of radiation image capturing devices 1 exist in the image capturing room Ra.

Therefore, in the above standard 1, in addition to the detailed standards [1-1] and [1-2], detailed standards need to be finely set considering a case where there are a plurality of radiation image capturing devices 1 in the image capturing room Ra. When there are a plurality of radiation image capturing devices 1 in the image capturing room Ra in advance, when a new radiation image capturing device 1 is brought into the image capturing room Ra, the above standard 3 is applied.

When there are a plurality of radiation image capturing devices 1 in the image capturing room Ra in advance, the above detailed standards [1-1] and [1-2] of the standard 1 are applied. Other than the above, when there are a plurality of radiation image capturing devices 1 in the image capturing room Ra in advance, the following detailed standard is set.

In the present embodiment, the detailed standard is applied with a higher priority than the detailed standards [1-1] and [1-2] of the standard 1, the detailed standard is [1-0].

[1-0] When there are a plurality of radiation image capturing devices 1 in the image capturing room Ra, and the starting state are the same, the console 58 selects and displays with focus the icon I corresponding to the image capturing order information where image capturing can be performed without changing the present starting state of the radiation source 52 (in other words started or not) and the present emission direction of the radiation source 52, or the icon I corresponding to the image capturing order information where the degree of change of the starting state or the emission direction is minimum.

Figure 22:
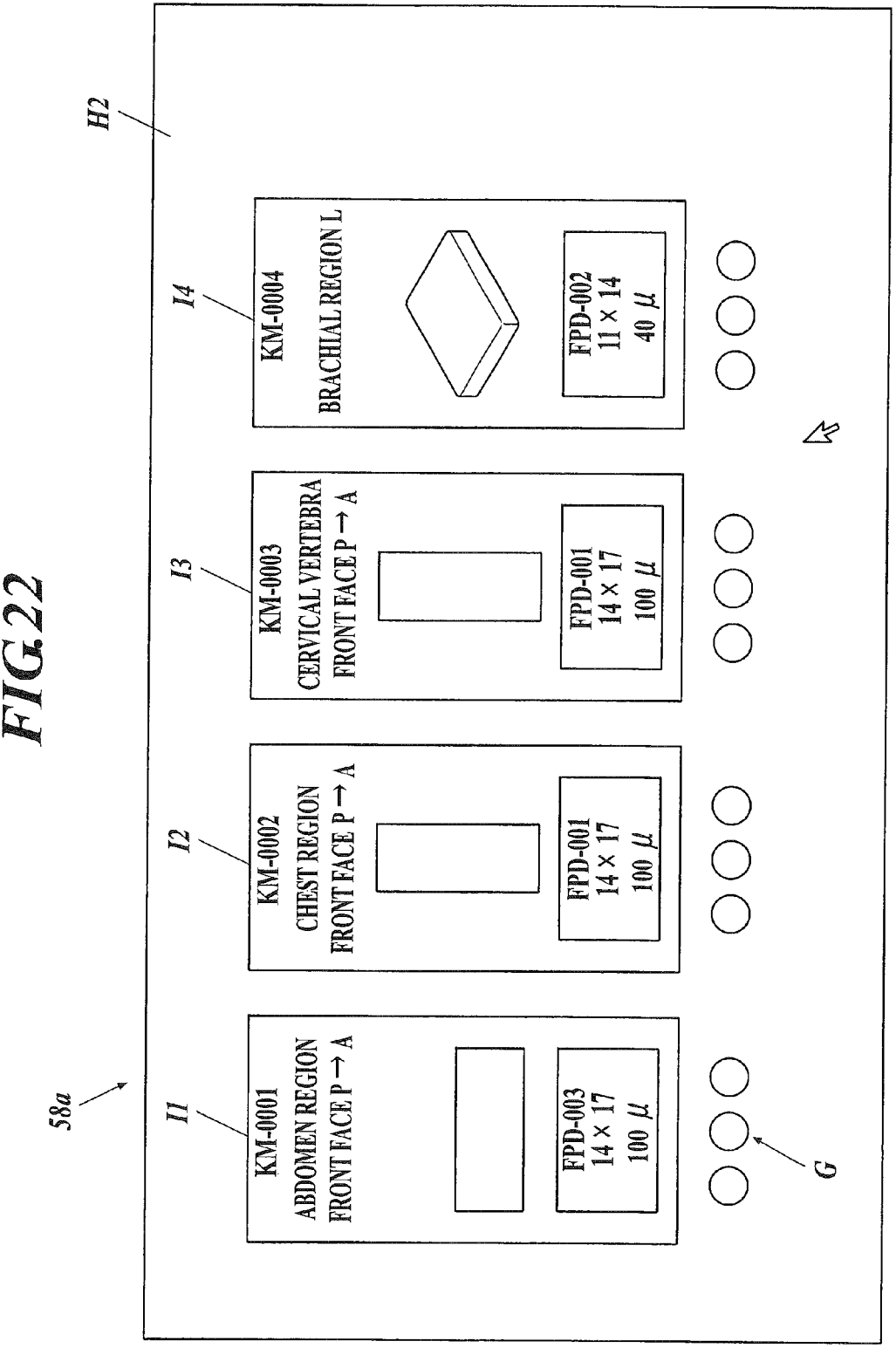
FIG. 22 is a diagram showing an example of a selection screen displayed in the display unit of the console when there are a plurality of portable radiation image capturing devices in the capturing room according to the second embodiment.

Therefore, when there are a plurality of radiation image capturing devices 1 in the image capturing room Ra and for example, as shown in FIG. 22, the radiation image capturing devices 1 are already loaded into each bucky device 51A for image capturing in a standing position and bucky device 51B for image capturing in a lying position, the console 58 first obtains information of the present starting state and the information of the emission direction of the radiation source from the radiation sources 52A and 52B.

Then, for example, when the radiation source 52A is already started, and the radiation source 52A is facing the direction of the bucky device 51B for image capturing in a lying position or the bucky device 51A for image capturing in a standing position, the icon displayed focused is the icon I1 or the icon I2 corresponding to the image capturing order information which can perform image capturing without changing the emission direction of the started radiation source 52A.

For example, when the radiation source 52A is not started but the radiation source 52A is facing the direction of the bucky device 51B for image capturing in a lying position or the bucky device 51A for image capturing in a standing position, the icon displayed focused is the icon I1 or the icon I2 corresponding to the image capturing order information which can perform image capturing by simply starting the radiation source 52A.

For example, when the radiation source 52A is not facing the direction of the bucky device 51B for image capturing in a lying position or the bucky device 51A for image capturing in a standing position, but the radiation source 52A is started and the portable radiation source 52B is not started, the icon displayed focused is the icon I1 or the icon I2 corresponding to the image capturing order information which can perform image capturing by only changing the emission direction of the radiation source 52A. In this case, when the standard 2 of the default case is applied, the icon I1 is displayed focused.

However, if another standard is set in the detailed standard of standard 1, the icon I2 may be displayed focused.

For example, when the radiation source 52A is not started and the portable radiation source 52B is started, the icon displayed focused is the icon I4 corresponding to the image capturing order information which can perform image capturing by only setting the emission direction of the radiation source 52B.

When there are a plurality of radiation image capturing devices 1 in the image capturing room Ra in advance and when the starting state is the same, for example the icon I displayed focused is the icon I corresponding to the image capturing order information which can perform image capturing without changing the present starting state of the radiation source 52 and the present emission direction of the radiation source 52, or the icon I corresponding to the image capturing order information in which degree of change of the starting state and the emission direction is minimum.

In the present case, it is possible to select which icon I is displayed focused based on only the present starting state of the radiation source 52 or only the present emission direction of the radiation source 52.

As described above, when the radiation source 52A is not facing the direction of the bucky device 51B for image capturing in a lying position and the bucky device 51A for image capturing in a standing position but the radiation source 52A is started and the portable radiation source 52B is not started, it is possible to perform image capturing based on the image capturing order information corresponding to either the icon I1 and the icon I2 by only changing the emission direction of the radiation source 52.

Figure 23:
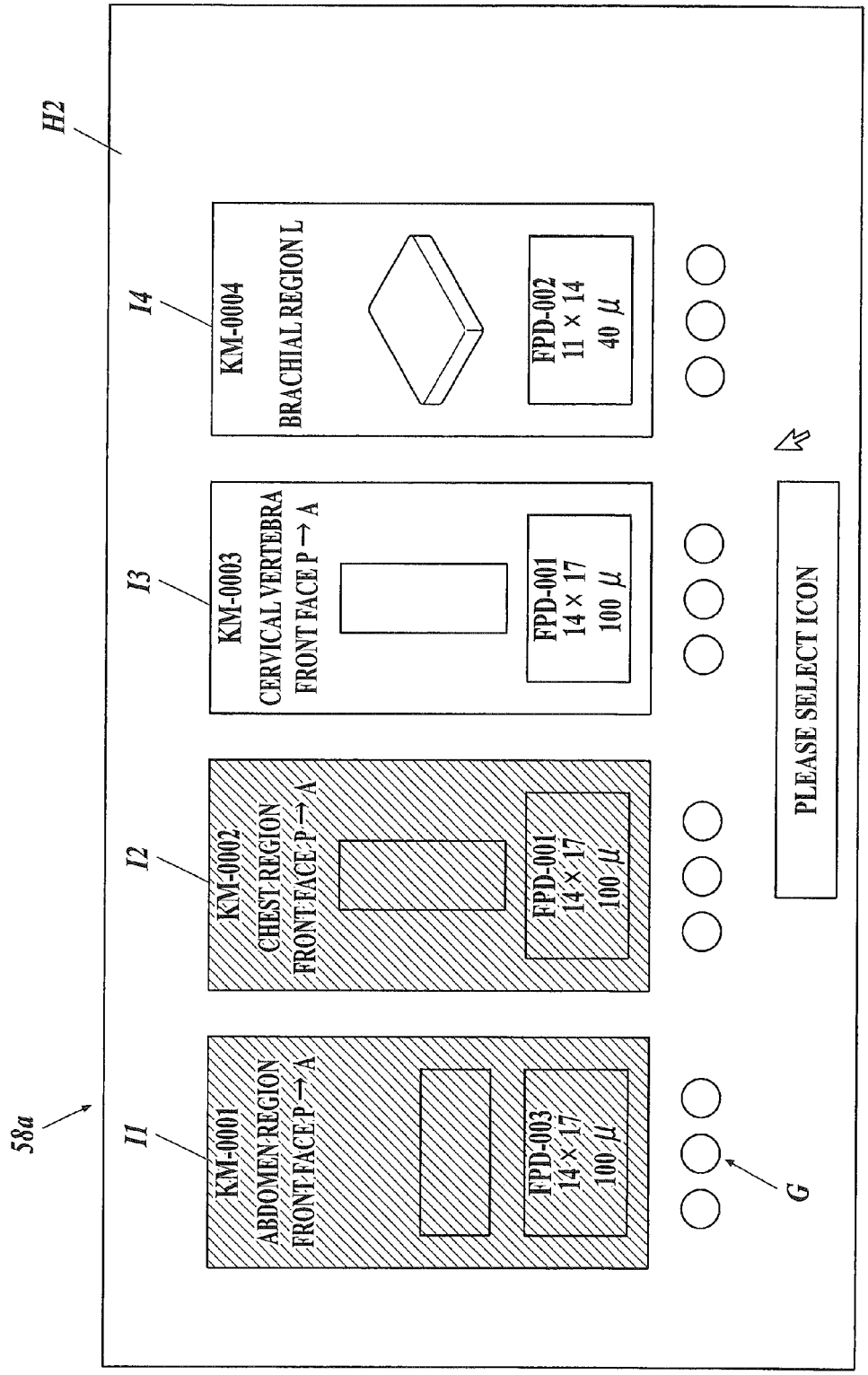
FIG. 23 is a diagram describing the corresponding plurality of icons are each displayed focused when there are a plurality of pieces of image capturing order information with which capturing can be performed.

As described above, when there are a plurality of pieces of image capturing order information which can perform image capturing, for example, as shown in FIG. 23, the plurality of icons I1 and I2 each corresponding to the plurality of pieces of image capturing order information can be each displayed focused, and the display of "please select icon" etc. can be displayed at the bottom of the screen H2 to notify that an icon I can be selected from the plurality of icons I1 and I2.

Then, when the operator selects and clicks any one of the icons I1 and I2, then, only the icon I clicked and selected is displayed focused.

With such configuration, image capturing can be performed according to the intension of the operator and the radiation image capturing system 50 is easy to use for the operator.

As described in the first embodiment, the radiation image capturing device 1 can be switched between the modes of the image capturing possible mode and the sleep mode. When the console 58 is able to manage the mode of each radiation image capturing device 1 and is able to manage which radiation image capturing device 1 among the plurality of radiation image capturing devices 1 can perform image capturing (in other words, the image capturing possible mode), it is possible to apply the above standards 1 to 3 and the detailed standards [1-0] to [1-2] of the standard 1 to the radiation image capturing device 1 which is a state to be able to perform image processing.

Specifically, when the radiation image capturing device 1 is loaded into the bucky device 51, the power source is supplied from the bucky device 51, therefore it is possible to use the radiation image capturing device 1 without considering the life of the included battery 24. Therefore, the inner reading circuit 17, etc. operates stably and reset can be performed periodically according to necessity. Therefore, image capturing can be performed immediately.

With such configuration, the radiation image capturing device 1 already in the image capturing possible mode can be used to perform image capturing without switching to the image capturing possible mode of the radiation image capturing device 1 and waiting for the reset processing, etc. of each radiation detecting element 7 to be completed in the radiation image capturing device 1.

Therefore, it is possible to perform image capturing promptly because it is possible to perform image capturing without switching the mode of each radiation image capturing device 1, without changing the loading state of the radiation image capturing device 1 on the bucky device 51, without changing the starting state, emission direction, etc. of each radiation source 52 or in a state where the degree of change is minimum. Therefore, the radiation image capturing system 50 is easy to use for the operator such as the radiation technologist, etc. and it is possible to perform efficient radiation image capturing.

When there are a plurality of radiation image capturing devices 1 which can perform image capturing and there are a plurality of pieces of image capturing order information which can perform image capturing, for example, as shown in FIG. 23, it is possible to display with focus the plurality of icons I corresponding to the plurality of pieces of image capturing order information and to notify that an icon I among the plurality of icons I can be selected.

Then, with such configuration, it is possible to perform image capturing according to the intension of the operator and the radiation image capturing system 50 is easy to use for the operator.

As described in the first embodiment, when at first only one radiation image capturing device 1 is brought into the image capturing room Ra and the operator such as the radiation technologist, etc. brings a new and different radiation image capturing device 1 into the image capturing room Ra, the icon I displayed focused can be automatically switched to the icon I corresponding to the image capturing order information specifying image capturing using the radiation image capturing device 1 newly brought in or after the state where there are a plurality of radiation image capturing devices 1, when the selection switch 38 of any of the radiation image capturing devices 1 is operated, the icon I displayed focused can be switched to the icon I which can use the radiation image capturing device 1.

However, when the image capturing based on the image capturing order information corresponding to the icon I switched and focused is finished, there are a plurality of radiation image capturing devices 1 in the image capturing room Ra. Therefore, in the later image capturing, the configuration described in the first embodiment can be applied, or the focused icon I can be switched to the icon I newly selected by the operator according to the standard 3, or when any one of the plurality of radiation image capturing devices 1 is operated with the selection switch 38 by the operator, the focused icon I can be switched to the radiation image capturing device 1 which can be used.

[Third Embodiment]

The above first and second embodiment describes performing image capturing using the portable radiation image capturing device 1 used loaded into the bucky device 51 or the radiation image capturing device 1 used by itself without loading into the bucky device 51.

The third embodiment describes providing a dedicated device for image capturing in a standing position and a dedicated device for image capturing in a lying position in the image capturing room Ra instead of the bucky device 51A for image capturing in a standing position and the bucky device 51B for image capturing in a lying position.

In this case also, the present invention is applied when only the dedicated device for image capturing in a standing position or only the dedicated device for image capturing in a lying position is provided in the image capturing room Ra. In this case, the portable radiation image capturing device 1 is used to perform image capturing in a state by itself.

In the third embodiment, the dedicated device for image capturing in a standing position is in a similar state as the portable radiation image capturing device 1 loaded into the bucky device 51A for image capturing in a standing position shown in the second embodiment, and the dedicated device for image capturing in a lying position is in a similar state as the portable radiation image capturing device 1 loaded into the bucky device 51B for image capturing in a lying position. Therefore, the configuration of control of the radiation image capturing system 50 is similar to the configuration described in the second embodiment.

When image capturing is performed a plurality of times on the same day using the dedicated device for image capturing in a standing position and the dedicated device for image capturing in a lying position, usually, after the power of each dedicated device is turned on before the first image capturing is performed, the power remains on without turning the power on or off, so that it is possible to switch the modes of each dedicated device between the image capturing possible mode and the sleep mode.

Therefore, in such case, it is possible to employ the configuration described in the second embodiment in which the console 58 manages the mode of each radiation image capturing device 1 (dedicated device) and to apply the above standards 1 to 3 and the detailed standards [1-0] to [1-2] of the standard 1 on the radiation image capturing device 1 (dedicated device) which can perform image capturing.

The third embodiment can also achieve the same outstanding effects as described in the second embodiment.

The first and second embodiments describe providing a bucky device 51 in the image capturing room Ra and the third embodiment describes providing a dedicated device in the image capturing room Ra. However, the present invention can be applied to a situation where the bucky device 51 and the dedicated device both exist in the image capturing room Ra.

The bucky device 51 and the dedicated device of the above embodiments include other types of radiation image capturing devices such as a radiation image capturing device which can perform image capturing in a long length where an image is captured in a wide range of the body of the patient while changing the position of the radiation image capturing device in the height direction of the patient or a mammography device which can capture images of the breast of the patient. In this case also the present invention can be applied.

The above embodiments describe the image capturing room Ra corresponded one to one with the console 58. Alternatively, as described in the later described FIG. 26 and FIG. 27, it is possible to apply the above configuration of the embodiments when a plurality of image capturing rooms Ra are connected with one or a plurality of consoles 58 (described as console C in FIG. 26 and FIG. 27) through a network, etc.

[Transmission of Generated Radiation Image (Medical Image) to External Devices]

Lately, a technology of PACS (Picture Archiving and Communication System) is developed, where the radiation image of the patient is captured using the radiation image capturing device as described above and transmitting and receiving the image data of the radiation image between devices and systems through a network.

In order to perform image examination to judge whether accurate image processing needs to be performed on the captured radiation image, the generated radiation image can be transmitted to a QA (Quality Assurance) station.

Below, the above are collectively referred to as a medial image system. Below, the generated radiation image is used for medical diagnosis and called medical image. In the above described PACS, QA station, etc., the transmitted medical image is interpreted to perform diagnosis and examination, and the above is collectively called the interpretation system.

In other words, the medical image system at least includes the radiation image capturing system as described above for capturing the medical image using the radiation image capturing device and the interpretation system for interpreting the medical image.

In such medical image system, the medical image is usually managed based on the image capturing order information (for example, see FIG. 13 and FIG. 14) as described above. The image capturing order information sets information, instructions, etc. regarding the radiation image capturing performed in the image capturing room determined based on inquiry to the patient, etc. and the items specified and registered may be, for example, patient information such as patient ID, etc., image capturing condition such as the portion of the body of the patient to be captured (in other words, capturing portion), device information specifying capturing direction, device to be used, etc.

With the console of the radiation image capturing system, the radiation image capturing device, the radiation generating device, etc. are controlled based on each piece of image capturing order information selected by the operator such as the radiation technologist, etc.

The conventional system as described in patent document 5 provides a configuration where each piece of image capturing order information regarding the patient who comes is displayed as a switch in a list on the display unit of the console, and the operator can select each image capturing order information freely from the switch of each piece of image capturing order information displayed in a list in an order so that it is easy to perform image capturing.

In the system described in patent document 5, the medical image captured based on each piece of image capturing order information is transmitted to the interpretation system side in the order requested by the doctor, etc. who performs interpretation.

However, in such conventional medical image system, the doctor often needs to request or specify the order of transmission of the medical images each time and there are doctors who dislike being requested specification of order of transmission of the medical images. However, when the medical images are not transmitted in the order that the doctor, etc. desires to interpret, the doctor, etc. needs to rearrange the order of the medical image each time, and the medical image system becomes difficult to use for the doctor, etc.

In view of the above points, described below is a radiation image capturing system which includes a console which is able to transmit the medical image in the order the doctor, etc. desires to interpret from the radiation image capturing system side to the interpretation system side without the doctor, etc. specifying the order of transmission of the medical image and a medical image system which includes the radiation image capturing system and the interpretation system.

Below, an embodiment of the medical image system is described with reference to the drawings. The invention described below is not limited to the illustrated examples.

Figure 24:
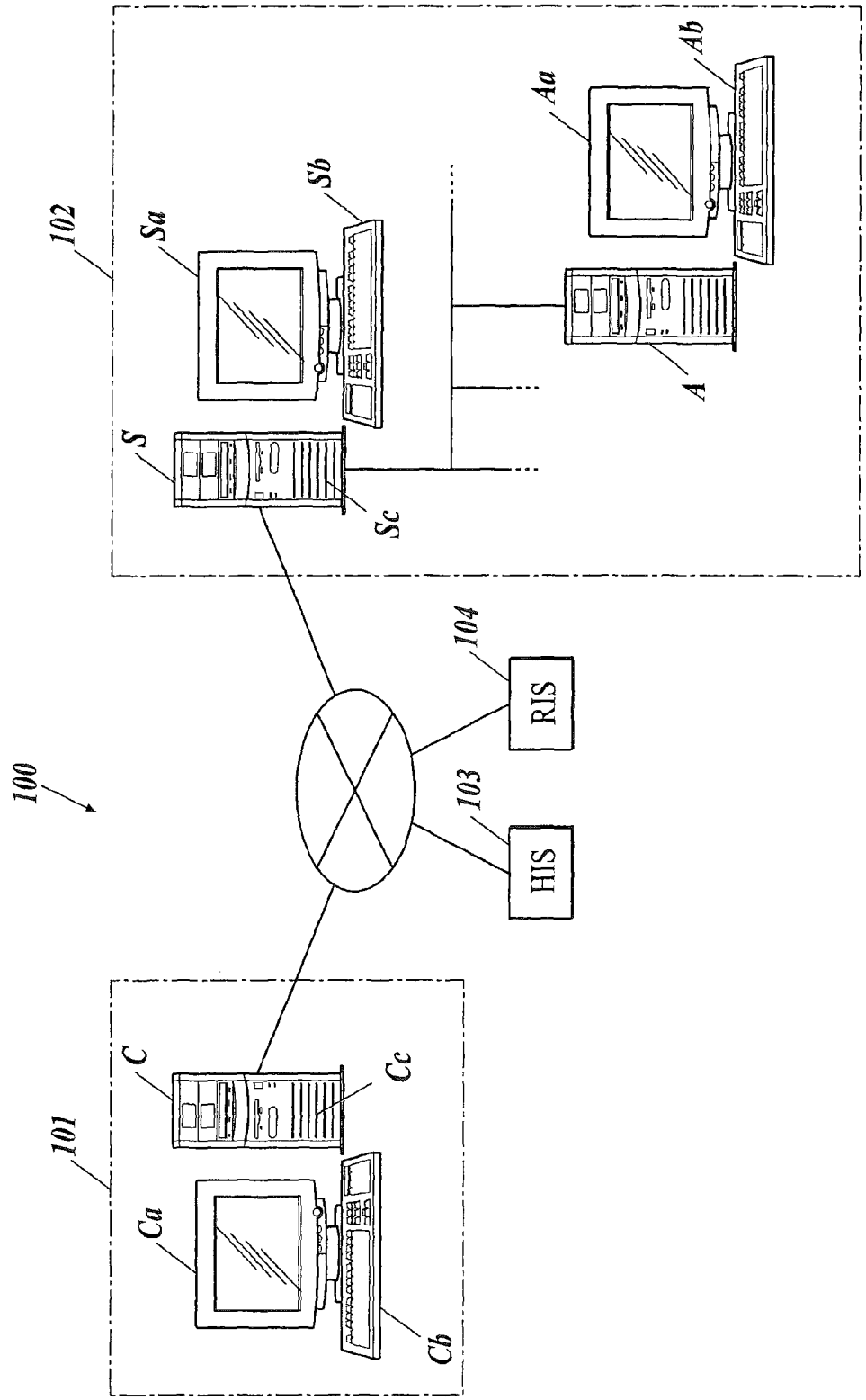
FIG. 24 is a diagram showing an entire configuration of a medical image system.

FIG. 24 is a diagram showing an entire configuration of a medical image system 100. The medical image system 100 at least includes a radiation image capturing system 101 which includes a console C and emits radiation to the patient to perform radiation image capturing and an interpretation system 102 which includes an interpretation image management device S and an image display device A for interpreting the medical image transmitted from the console C to perform diagnosis, examination, etc. The radiation image capturing system 101 and the interpretation system 102 are connected through a network such as a LAN (Local Area Network), etc.

Specifically, the interpretation system 102 is assumed to be the above described PACS, QA station, etc. The radiation image capturing system 101 and the console C are basically similar to the above described radiation image capturing system 50 (see FIG. 1) and the console 58. However, in the present invention, as described in FIG. 26 and FIG. 27, the image capturing room Ra and the console are not necessarily corresponded one to one. Therefore, the above is referred to as the radiation image capturing system 101 and the console C.

A HIS (Hospital Information System) 103 and a RIS (Radiology Information System) 104 are connected to the medical image system 100 through the network. In addition, although illustration is omitted, other computers and external devices such as an imager which records the medical image on an image recording medium such as film, etc. to output the image are connected.

Figure 25:
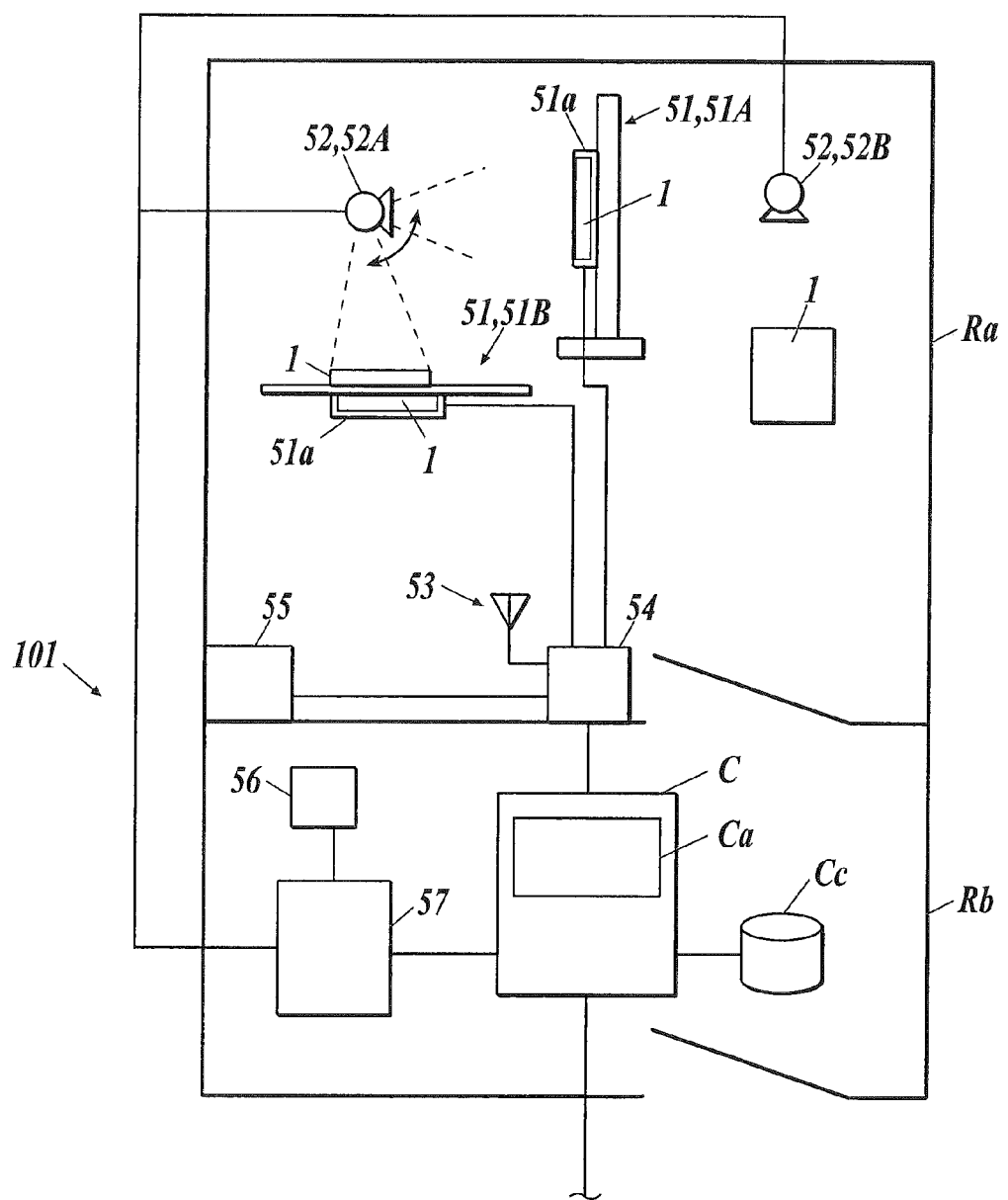
FIG. 25 is a diagram showing an example of a configuration of the radiation image capturing system of the medical image system shown in FIG. 24.

As shown in FIG. 25, in the present embodiment, the radiation image capturing system 101 is structured in an image capturing room Ra including a front room (also called operation room, etc.) Rb.

The radiation image capturing device 1, and the devices, etc. provided in the image capturing room Ra and the front room Rb are similar to the above embodiments, and therefore description is omitted.

The present embodiment describes the simplest example where the radiation image capturing system 101 is structured in the image capturing room Ra corresponded to one console C as described in FIG. 25. However, the present invention can be applied to a configuration where a plurality of image capturing rooms Ra (Ra1 to Ra4) are connected in a predetermined connection with the plurality of consoles C (C1 to C3) as shown in FIG. 26, or a plurality of image capturing rooms Ra (Ra1 to Ra4) are connected to each plurality of consoles C (C1 to C3) through a network N.

Figure 26:
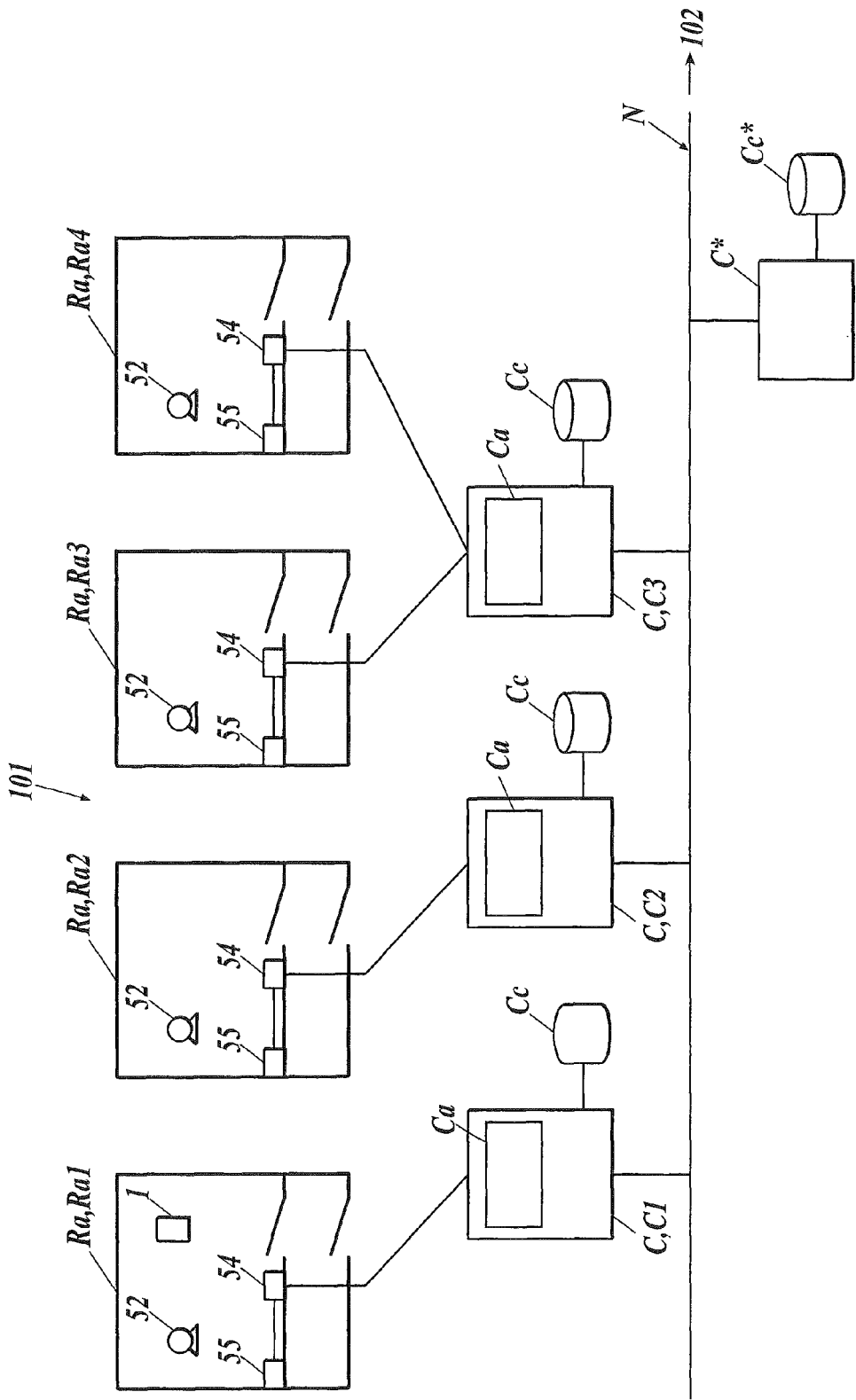
FIG. 26 is a diagram showing an example of a radiation image capturing system where the plurality of image capturing rooms and the plurality of consoles are connected in a predetermined method.
Figure 27:
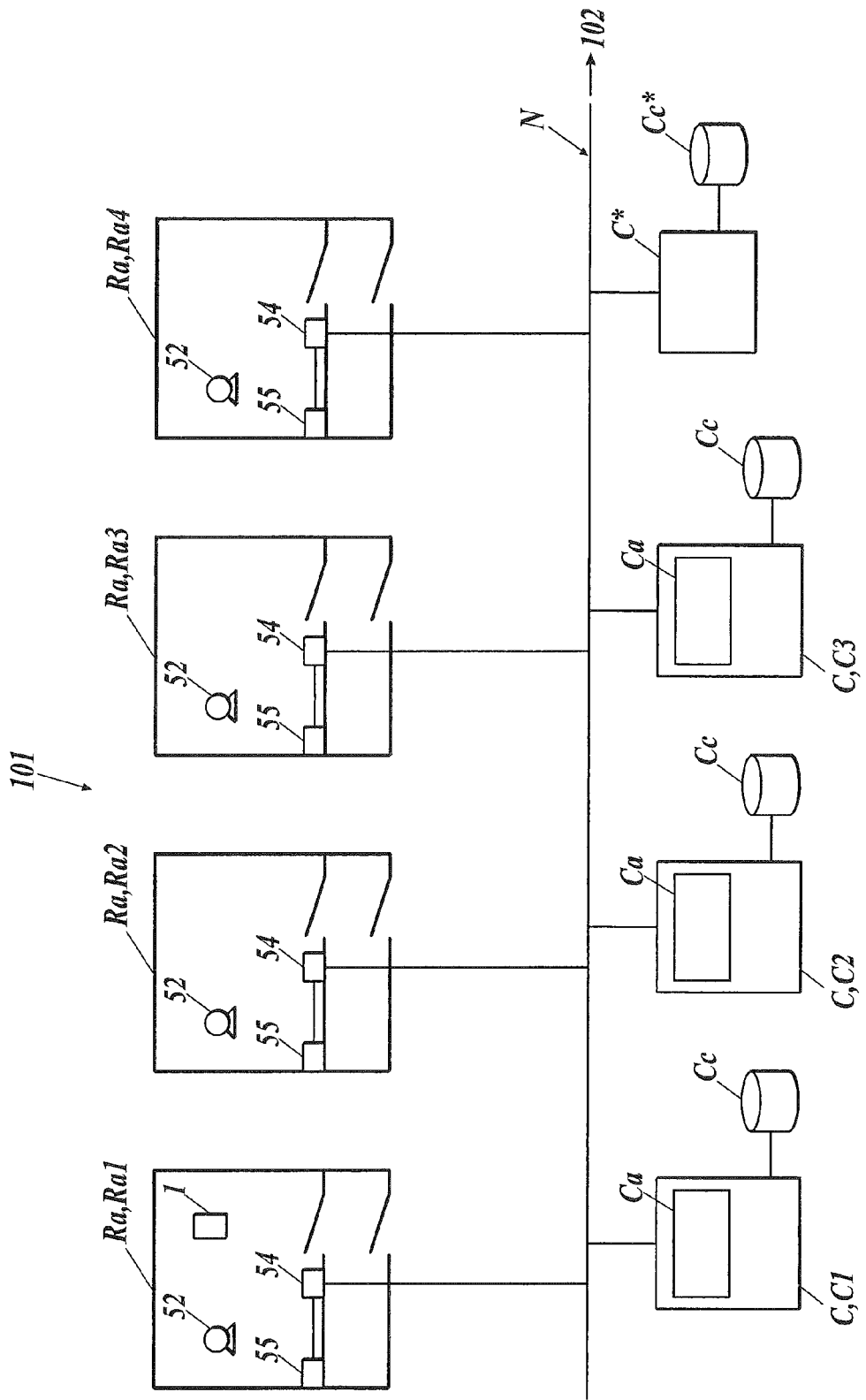
FIG. 27 is a diagram showing an example of a radiation image capturing system in which the plurality of image capturing rooms and the plurality of consoles are each connected through a network.

In this case, as shown in FIG. 26 and FIG. 27, a management device C* such as a server can be provided connected with each console C through a network N, etc. or instead of providing the management device C*, any one of the console C can be used as a substitute of the management device C*. In this case, the management device C* or the console C substituting the management device C* performs later described processing where the information transmitted from the interpretation image management device S of the interpretation system 102 is received and the order of transmission is modified, etc.

Further, obtaining image capturing order information with the console C, focus display of the icon I, display of the preview image p_pre, generating the radiation image p in other words the medical image p are similarly performed as in the above embodiments, and the description is omitted.

Next, the setting, modifying, etc. of the order of transmission of the medical images from the console C to the interpretation image management device S of the interpretation system 102 is described together with the operation of the radiation image capturing system 101 and the medical system 100 (see FIG. 24) of the present embodiment. Below, the medical images obtained and generated corresponding to each icon I1 to I4 are referred to as medical images p1 to p4.

Figure 28:
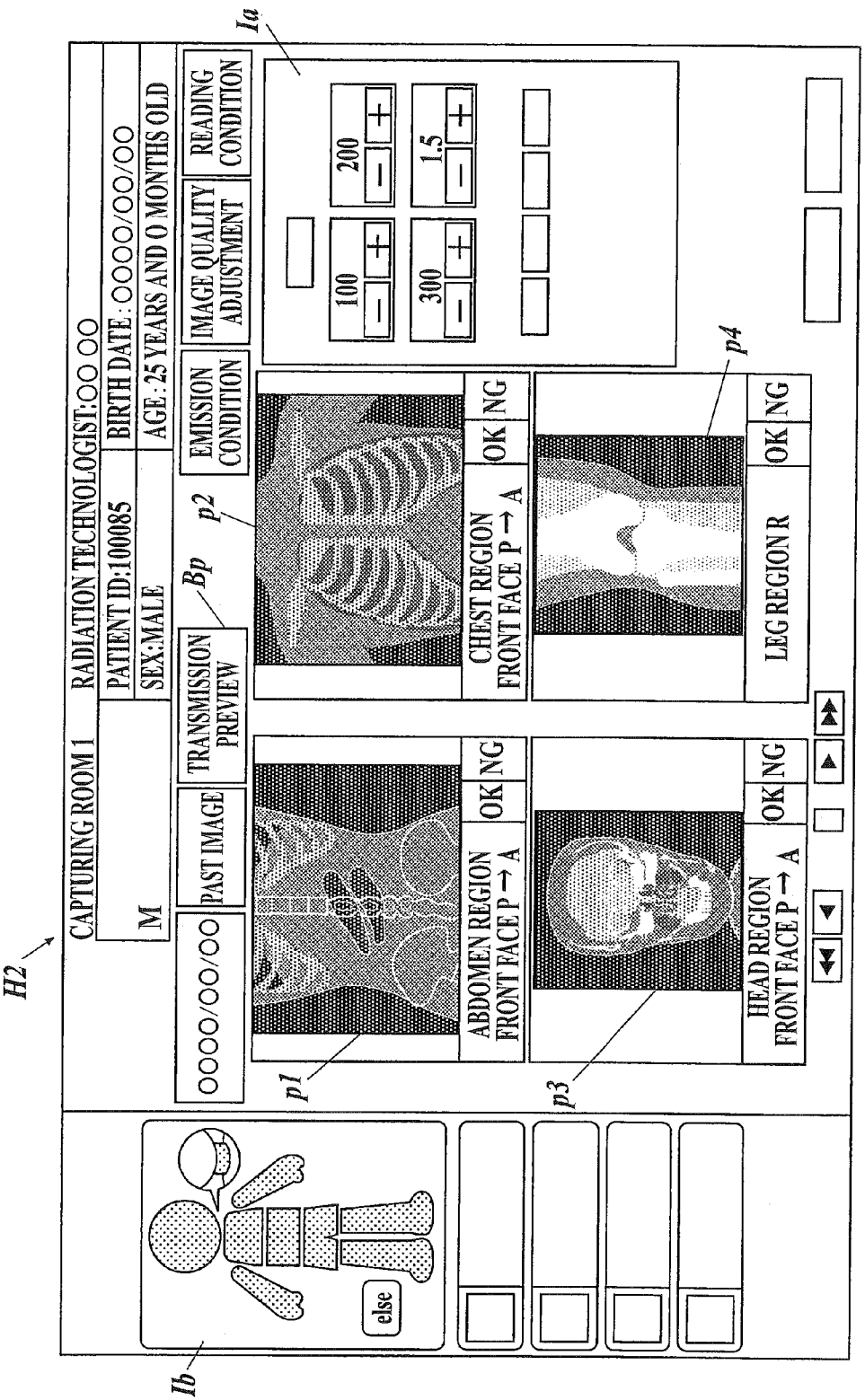
FIG. 28 is a diagram showing a state where each medical image corresponding to each icon is displayed in the position where each icon is displayed.

For example, when all of the radiation image capturing corresponding to each icon I1 to I4 on the screen H2 of the display unit Ca of the console C finishes, as described in FIG. 28, the corresponding medical images p1 to p4 are displayed in a position where each icon I1 to I4 is displayed.

The screen H2 shown in FIG. 28 is an example of a different configuration of the screen H2 shown in FIG. 15 to FIG. 23, and basically operates the same as the operation of the screen H2 shown in FIG. 15 to FIG. 23.

On the screen H2 shown in FIG. 28, the "+" button and the "−" button of each item on the display Ia for setting an emission condition displayed on the right side of the screen H2 can be clicked to be able to change and set the emission conditions such as tube voltage, tube current, emission time, etc. when emitting radiation from the radiation source 52 (see FIG. 1 and FIG. 25) of the radiation generating device 57.

On the left side of the screen H2, the capturing portion specified in the image capturing order information corresponding to the icon I displayed with focus is displayed in the human body model Ib shown so that the operator is able to understand at a glance. For example, when the icon I2 specifying the image capturing the chest region from the front face is displayed with focus, the portion of the chest region of the human body model Ib is displayed in a different manner from the other portions such as colored in red. The example of FIG. 28 describes an example where all of the radiation image capturing corresponding to each icon I1 to I4 is finished, and a specific capturing portion of the human body model Ib is not displayed with highlight.

In the example described in FIG. 28, as shown in FIG. 24, the medical images p1 to p4 are transmitted from the console C of the radiation image capturing system 101 through a network such as the LAN to the interpretation image management system S of the interpretation system 102 such as the PACS, QA system, etc.

In the interpretation system 102, when a generated string of medical images p are transmitted from the console C of the radiation image capturing system 101, each medical image p is stored in the storage unit Sc including an HDD, etc. and the interpretation image management device S manages the medical image p. Each medical image p is transmitted from the interpretation image management device S to each image display device A as necessary, and each image p is displayed on the screen of a display unit Aa of each image display device A to be interpreted.

An input unit Ab such as a keyboard, mouse, etc. is connected to the image display device A and it is possible to operate the input unit Ab of the image display device A to change the order that the string of medical images p displayed on the screen of the display unit Aa is interpreted, in other words, the order of display for interpretation of the medical image p displayed on the screen of the display unit Aa of the image display device A for the doctor, etc. who interprets the string of medical images p.

When the order of display of the string of medical images p is changed by the doctor, etc. the image display device A sequentially notifies the changed order of display to the interpretation image management device S.

To simplify explanation, an example below describes changing the order of interpretation and display of the string of medical images p only with the image display device A. However, as shown in FIG. 24 it is possible to connect the display unit Sa, the input unit Sb, etc. to the interpretation image management device S itself and to change the order of interpretation and display of the string of medical images p on the interpretation image management device S.

In the present embodiment, the order of transmission when the string of medical images p are transmitted from the console C of the radiation image capturing system 101 to the interpretation image management device S of the interpretation system 102 is determined by the capturing portion and the capturing condition determined in each piece of image capturing order information which is the base of image capturing of each medical image p1 to p4.

For example, a basic rule of the order of transmission may be determined in the hospital or clinic where the radiation image capturing system 101 is applied. In this case, for example, as shown in the table of FIG. 29, the string of medical images p is transmitted in the order determined by the capturing portion or capturing condition.

However, for example, as described above, the order of display of the string of medical images p for a certain patient may be changed by the doctor, etc. on the image display device A of the interpretation system 102. In such example, when the medical images p are transmitted later, if the string of medical images p are transmitted based on the above basic rules according to the table shown in FIG. 29, the doctor, etc. needs to change the order of display of the string of medical images p of the patient on the image display device A each time, which is a burden.

Therefore, other than the table according to the basic rule as shown in FIG. 29, the console C includes a table corresponding the capturing portion and the capturing condition with the order of transmission for each patient and when the string of medical images p of the patient is transmitted to the interpretation image management device S, this table is referred to determine the order of transmission of the string of medical images p. Moreover, when the order of display of the string of medical images p is changed on the image display device A and the interpretation image management device S, the table is modified according to the change.

Below, the above is specifically described. Below, in order to distinguish from the table according to the basic rule (see FIG. 29), the table modified and determined for each patient is to be a history table T.

In the default state, the history table T showing the order of transmission of the string of medical images p from the console C to the interpretation image management device S is the same as the table according to the basic rules as shown in for example, FIG. 29. As shown in FIG. 29, regarding at least the capturing portion, the history table T is set to transmit from the portion of the upper side of the body of the patient first and then to sequentially transmit toward the lower side. Then, regarding each capturing portion, the order of transmission is set in detail for each capturing condition.

The history table T showing the order of transmission is managed for each patient, in other words, in the present embodiment corresponded to each patient ID and stored in, for example, the storage unit Cc. Then, when the string of medical images p of the patient is transmitted to the interpretation image management device S, the console C refers to the history table T of the order of transmission corresponded to the patient ID of the patient, and transmits the string of medical images p in order according to the above.

For example, in the example of the string of medical images p1 to p4 shown in FIG. 28, in the default state, the console C determines the transmission order to transmit to the interpretation image management device S in the order of medical image p3 of head region front face, medical image p2 of chest region front face, medical image p1 of abdomen region front face, medical image p4 of leg region R, and transmits the string of medical images p1 to p4 to the interpretation image management device S of the interpretation system 102 in this order.

The string of medical images p1 to p4 transmitted according to the above order of transmission are transmitted from the interpretation image management device S to the predetermined image display device A and usually interpreted with the image display device A by the attending doctor of the patient M. On the screen of the display unit Aa of the image display device A, the string of medical images p1 to p4 are displayed in the order of transmission transmitted from the console C to the interpretation image management device S.

Then, when the attending doctor of the patient M considers there is no problem with the order of display of the string of medical images p1 to p4 displayed on the screen of the display unit Aa of the image display device A, in other words, the order of transmission, usually the order of display of the string of medical images p1 to p4 is not changed. Therefore, in this case, since the order of display, in other words, the order of transmission is not changed, later, when the medical image p of the patient M is transmitted, the console C transmits the medical image p to the interpretation image management device S according to the order of transmission shown in FIG. 29, in other words, the history table T.

Figure 30:
FIG. 30 is a diagram showing an example of a history table of the order of transmission which is modified by adding capturing portion and capturing condition to the bottom of the table shown in FIG. 29.

When the next time, image capturing of the capturing portion or the capturing condition which is not determined in the history table T is performed on the patient, in other words, for example, image capturing of an image of the whole body of the patient M obtained by image capturing long in length which is not determined in the history table T of FIG. 29 is performed, the console C considers these images as the medical image p performed with new capturing portion and capturing condition and adds the capturing portion and the capturing condition such as capturing portion "whole body" capturing condition "front face P→A" to the most bottom area of the history table T as shown in FIG. 30 to modify the history table T.

Then, according to the modified history table T, the medical image p is transmitted to the interpretation image management device S. Therefore, the next time after the next time, when similar image capturing is performed and the string of medical images p are transmitted, for example, the medical image p, such as the above whole body image, which is the type newly added to the history table T of the order of transmission is transmitted last in the string of medical images p.

When the doctor, etc. rearranges and changes the order of display and interpretation (in other words, the order of display) of the string of medical images p1 to p4 on the screen of the display unit Aa of the image display device A, as described above, the changed order of display of the string of medical images p1 to p4 is notified from the image display device A to the interpretation image management device S.

In this case, for example, when the medical images p1 to p4 are transmitted in the order of the medical image p3 of head region front face, the medical image p2 of chest region front face, the medical image p1 of abdomen region front face, and the medical image p4 of leg region R from the console C to the interpretation image management device S, each medical image p3, p2, p1 and p4 are displayed in this order on the screen of the display unit Aa of the image display device A.

As an example, when the doctor, etc. interprets the medical image p, the medical image p3 of head region front face is moved after another medical image p and the display order is rearranged and changed to an order of, for example, the medical image p2 of chest region front face, the medical image p1 of abdomen region front face, the medical image p4 of leg region R, and the medical image p3 of head region front face.

Then, when the order of display of each medical image p1 to p4 is changed on the image display device A as described above, the changed display order [p2, p1, p4, p3] of the string of medical images p1 to p4 is notified from the image display device A to the interpretation image management device S. In the present embodiment, the interpretation image management device S notifies the notified changed display order [p2, p1, p4, p3] to the console C of the radiation image capturing system 101.

When the changed display order [p2, p1, p4, p3] is notified from the interpretation image management device S, the console C modifies the order of the capturing portion and the capturing condition determining the order of transmission of the medical image p and generates a new history table T of the order of transmission based on the changed display order [p2, p1, p4, p3].

Specifically, in this case, as described above, since the order of display is changed by moving the medical image p3 of head region front face after the other medical images which are the medical image p2 of chest region front face, the medical image p1 of abdomen region front face and the medical image p4 of leg region R, the console C reads the history table T of the order of transmission regarding the patient M from the storage unit Cc and modifies the history table T form the state shown in FIG. 29 to the state shown in FIG. 31.

Then, the history table T after modification is stored overwriting the history table T of the order of transmission regarding the patient M stored in the storage unit Cc. Even if the capturing portion is the same, when the order of display of the medical image p with the different capturing condition is changed, the order of the capturing condition of the capturing portion in the history table T of the order of transmission is modified to match the change, and the history table T with the new order of transmission is generated.

With this, the order of transmission of the string of medical images p is modified corresponding to the order of display changed by the doctor, etc., and the above order is stored. Therefore, for example, when the attending doctor of the patient M interprets the string of medical images p regarding the patient M, the string of medical images p are transmitted and displayed to the image display device A in the order which the attending doctor desires to interpret.

Therefore, the attending doctor, etc. does not have to change the order of display of the medical image p each time on the screen of the display unit Aa of the image display device A. Moreover, even if the attending doctor, etc. does not specify the order of transmission of the medical images p each time on the console C, the string of medical images p are transmitted to the image display device A and displayed in the order in which the attending doctor desires to interpret. Therefore, the medical image system 100 (see FIG. 24) including the radiation image capturing system 101 and the interpretation system 102 becomes easy to use for the doctor, etc.

As described above, the modified history table T is stored overwriting the history table T of the order of transmission regarding the patient M stored in the storage unit Cc and when the medical images p are transmitted, the console C refers to the history table T of the order of transmission regarding the patient M stored in the storage unit Cc to transmit the string of medical images p. Therefore, the string of medical images p can be transmitted securely in the order of transmission according to the order of display modified by the doctor, etc.

Therefore, the attending doctor, etc. of the patient M can interpret the string of medical images p in the same order of display each time regarding at least the patient M, and can interpret the medical images p in the order of display matching his interpretation style.

When the attending doctor, etc. of the patient M desires to change the order of display of the string of medical images p regarding the patient M, by rearranging the order of display on the screen of the display unit Aa of the image display device A, the above is reflected on the order of transmission of the medical images p from then after, and it is easy to change the order of display of the medical images p. With this point, the medical image system 100 is easy to use for the doctor, etc.

When the order of display of each medical image p1 to p4 is changed on the image display device A, instead of the console C modifying the order of transmission from the console C to the interpretation image management device S, the modification can be performed in the interpretation image management device S which receives the notification of change of the order of display from the image display device A.

In this case, when the interpretation image management device S receives the notification to change the order of display of the string of medical images p from the image processing device A, based on the changed order of display, the interpretation image management device S changes the order of the capturing portion and the capturing condition in the history table T determining the order of transmission of the string of medical images p regarding the patient M as shown in the change from, for example, the transmission order shown in FIG. 29 to the transmission order shown in FIG. 31, to modify the history table T of the order of transmission and to change the order of transmission. Then, the changed history table T of the order of transmission is notified to the console C.

Then, the interpretation image management device S notifies to the console C the information of the history table T of the order of transmission regarding the patient M modified and changed in this way. The console C overwrites and stores the history table T of the order of transmission regarding the patient M modified with the interpretation image management device S on the history table T of the order of transmission regarding the patient M stored in the storage unit Cc.

According to the above configuration, it is possible to achieve the same advantageous effects as the above and the medical image system 100 is easy to use for the doctor, etc.

According to the above configuration, when the change of the order of display of the string of medical images p regarding a certain patient is performed on the interpretation image management device S or the image display device A of the interpretation system 102 included in the medical image system 100, the order of transmission of the medical images p regarding the patient from the console C of the radiation image capturing system 101 side of the medical image system 100 to the interpretation image management device S is modified to match the changed order of display, and the modified order of transmission is stored in the console C side.

Therefore, in the image capturing of the patient from the next time after, the operator such as the radiation technologist, etc. can transmit the string of medical images p regarding the patient from the console C in the order which the doctor, etc. desires to interpret, and it is possible to display the string of medical images p in the order which the doctor, etc. desires to interpret on the screen of the display unit Aa of the image display device A which the doctor, etc. interprets.

Then, the doctor, etc. does not have to change the order of display of the medical image p each time on the screen of the display unit Aa of the image display device A, and even when the doctor, etc. does not specify the order of transmission of the medical image p each time on the console C, the string of medical images p are automatically transmitted to the image display device A and displayed in the order which the doctor, etc. desires to interpret. Therefore, the string of medical images p can be interpreted in the order of display which matches the interpretation style of the doctor, etc. and the medical image system 100 is easy to use for the doctor, etc.

The above example describes modifying the order of transmission with the console C or the interpretation image management device S so that the order of transmission reflects the order of display of the string of medial images p changed on the interpretation image management device S and the image display device A. Other than the above, the operator such as the radiation technologist, etc. can change the order of transmission of the string of medical images p regarding the patient M on the console C side before transmitting the string of medical images p.

For example, when the operator such as the radiation technologist, etc. finds that the attending doctor of the patient M changed to a different doctor and the operator knows the order of display of the interpretation style of the new doctor, it is preferable that the operator can change the order of transmission of the string of medical images p regarding the patient M on the screen H2 of the console C in advance before the order of display is changed on the image display device A by the new doctor.

With such configuration, there is no need to transmit and receive information of the changed order of display or the changed order of transmission between the console C and the interpretation image management device S. Therefore, the burden on the medical image system 100 is reduced. Moreover, the new doctor does not have to rearrange the order of display of the string of medical images p and can immediately interpret the string of medical images p in the order of display which matches his interpretation style. Therefore, the medical image system 100 is easy to use for the new doctor.

In order to achieve the above, as shown in FIG. 28, on the console C of the present embodiment, when all of the radiation image capturing finishes based on all of the selected image capturing order information, in other words, in the example shown in FIG. 28, based on each piece of image capturing order information corresponding to the icons I1 to I4, and each medical image p1 to p4 is displayed in the corresponding position where each icon I1 to I4 was displayed, "transmission preview" button Bp is displayed above each medical image p1 to p4 of the screen H2.

Then, when the operator clicks the "transmission preview" button Bp, the screen switches and the transmission preview screen H3 as shown in FIG. 32 is displayed. On the transmission preview screen H3, according to the history table T of the transmission order, each preview image corresponding to the medical images p1 to p4 is displayed arranged in order from, for example, the left side. Below, the description is described as medical image p, etc. however, in the present embodiment, actually, each preview image corresponding to each medical image p is displayed on the transmission preview screen H3.

According to the history table T in the order of transmission shown in FIG. 29, the string of medial images p1 to p4 are displayed on the transmission preview screen H3 in the order of display shown in FIG. 32. In this case, as described above, according to the history table T of the order of transmission, the medical images p1 to p4 for diagnosis are displayed in the order of the medical image p3 of head region front face, the medical image p2 of chest region front face, the medical image p1 of abdomen region front face and the medial image p4 of leg portion R.

Then, below the above display, a message is displayed to ask whether or not the images should be transmitted in the order displayed and the operator such as the radiation technologist, etc. can select whether or not to transmit the string of medical images p1 to p4 in the order displayed.

Then, when the operator clicks the "OK" button, each medical image p1 to p4 is transmitted to the interpretation image management device S in the order of display, in other words, in the order of [p3, p2, p1, p4] according to the history table T of the order of transmission regarding the patient M shown in FIG. 29.

Figure 33:
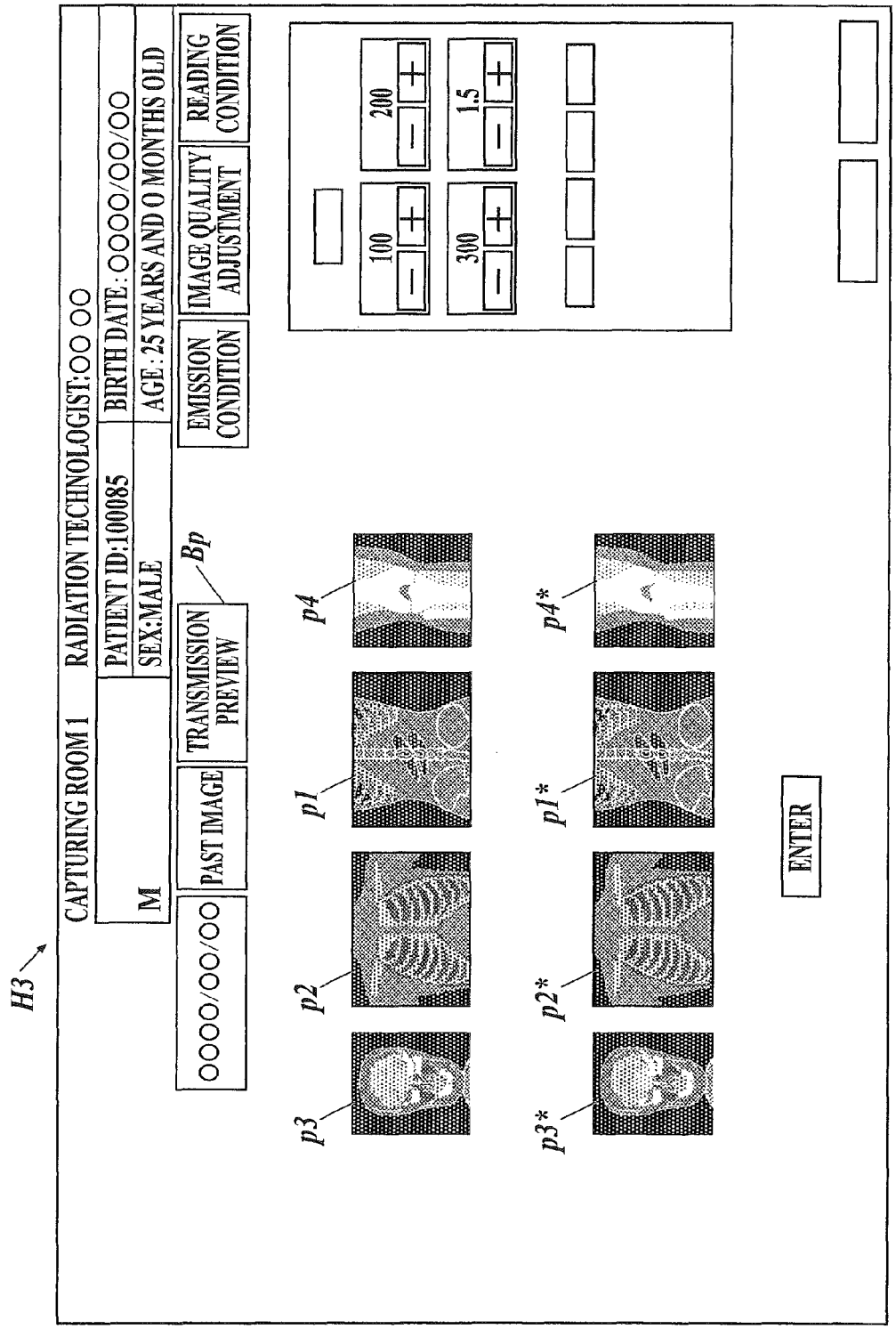
FIG. 33 is a diagram showing each medical image displayed below each medical image when the "NG" button is clicked in the transmission preview screen shown in FIG. 32.

When the images are not transmitted in the order of display, the "NG" button is clicked. When the "NG" button is clicked, as shown in FIG. 33, at the bottom of each medical image p1 to p4 displayed in the transmission preview screen H3, each medical image p1* to p4* is displayed in the same order as the medical images p1 to p4 of the upper side.

However, for example, by drag and drop, the order of display of each medical image p1* to p4* displayed on the lower side can be changed as shown in FIG. 34.

Then, when the operator changes the order of display of each medical image p1* to p4*, and the "enter" button at the bottom is clicked, as shown in FIG. 35, the console C displays each medical image p1 to p4 in the changed display order [p2, p1, p4, p3] and similar to the above modifies the order of the capturing portion and the capturing condition determining the order of transmission of the medical images p based on the changed display order [p2, p1, p4, p3].

In this case, a new history table T of the order of transmission is generated as shown in FIG. 31. Then, the console C overwrites and stores the modified history table T on the history table T of the transmission order regarding the patient M stored in the storage unit Cc and also transmits to the interpretation image management device S each medical image p in the order of [p2, p1, p4, p3] according to the changed history table T of the order of transmission.

Regarding when the order of transmission of the medical images p1 to p4 on the console C side is modified, instead of or in addition to after each medical image p1 to p4 is generated, it is possible to perform the modification when each image capturing order information is selected on the selection screen H1 and when each icon I1 to I4 corresponding to each piece of image capturing order information is displayed on the screen H2 using each icon I1 to I4.

In this case, although illustration is omitted, "transmission preview" button Bp as shown in FIG. 28 is displayed on the screen H2. Then, when the "transmission preview" button Bp is clicked at this time, the transmission preview screen H3 as shown in FIG. 32 is displayed.

In this case, on the transmission preview screen H3, instead of each medical image p1 to p4 as shown in FIG. 32, each icon I1 to I4 is displayed in the order of, for example, icons I3, I2, I1, I4 according to the history table of the order of transmission. Then, the icons I1 to I4 can be displayed rearranged as in each medical image p1 to p4 and p1* to p4* shown in FIG. 33 to FIG. 35, and the order of transmission of the medical images p1 to p4 can be modified on the console C side.

In this case, each icon I1 to I4 is rearranged in the order of [I2, I1, I4, I3] on the transmission preview screen H3, and then, when the screen is switched to the screen H2, according to the above change in order, it is possible to display each icon I2, I1, I4, I3 in the order of upper left, upper right, bottom left, bottom right on the screen H2. With such configuration, the radiation image capturing can be sequentially performed according to the changed order of transmission of the medical images p1 to p4 which is [p2, p1, p4, p3].

The above embodiments and modifications describe providing a bucky device 51 in the image capturing room Ra (see FIG. 25) of the radiation image capturing system 100 of the medical image system 100. However, the present invention can be applied to a state such as where only a dedicated device where the radiation image capturing device 1 is formed as one with a supporting stage, etc. is provided or where the bucky device 51 and the dedicated device are mixed in the image capturing room Ra.

The bucky device 51 and the dedicated device of the above embodiments include other types of radiation image capturing devices such as a radiation image capturing device which can perform image capturing in a long length where an image is captured in a wide range of the body of the patient while changing the position of the radiation image capturing device in the height direction of the patient or a mammography device which can capture images of the breast of the patient. In this case also the present invention can be applied.

The present invention is not limited to the above embodiments, and suitable changes are possible.

Industrial Applicability

The present invention can be applied to the field of radiation image capturing (specifically, the field of medicine).

The invention claimed is:

1. An x-ray radiation image capturing system comprising:
an x-ray radiation source which emits x-ray radiation on an object;
a portable x-ray radiation image capturing device which includes a plurality of x-ray radiation detecting elements which are two dimensional, and which reads charge generated in each x-ray radiation detecting element by the x-ray radiation emission as image data;
a bucky device into which the portable x-ray radiation image capturing device can be loaded; and
a console which manages at least whether or not the portable x-ray radiation image capturing device is loaded into the bucky device and which registers in advance a plurality of pieces of image capturing order information including information of whether or not to perform image capturing in a state where the portable x-ray radiation image capturing device is loaded into the bucky device or which is possible to obtain the registered plurality of pieces of image capturing order information,
wherein the console includes a display unit which displays an icon corresponding to each piece of image capturing order information;
the console displays each icon corresponding to each piece of image capturing order information in a predetermined order on the display unit;
when the portable radiation image capturing device is loaded into the bucky device, regardless of the predetermined sequence, the console displays the icon corresponding to the image capturing order information including information showing that the portable x-ray radiation image capturing device is loaded into the bucky device in a manner different from the other icons; and
when the portable radiation image capturing device is not loaded into the bucky device, regardless of the predetermined sequence, the console displays the icon corresponding to the image capturing order information including information showing that the portable x-ray radiation image capturing device is not loaded into the bucky device in a manner different from the other icons.

2. The x-ray radiation image capturing system of claim 1, further comprising either a bucky device for image capturing in a standing position, a bucky device for image capturing in a lying position or both of the above as the bucky device.

3. The x-ray radiation image capturing system of claim 1, wherein the bucky device transmits to the console information showing that the portable x-ray radiation image capturing device is loaded when the portable x-ray radiation image capturing device is loaded.

4. The x-ray radiation image capturing system of claim 3, wherein when the console receives information from the bucky device showing the portable x-ray radiation image capturing device is loaded, the console displays the icon corresponding to the image capturing order information including information showing that the portable x-ray radiation image capturing device is loaded into the bucky device in a manner different from the other icons.

5. The x-ray radiation image capturing system of claim 4, wherein, when a specific icon is to be displayed in a manner different from the other icons and an icon other than the specific icon is displayed in a manner different from the other icons, the console returns the display of the icon displayed in the manner different from the other icons to a display in a manner same as the other icons.

6. The x-ray radiation image capturing system of claim 1, wherein,
other than the portable x-ray radiation image capturing device, a CR cassette can be loaded into the bucky device and the bucky device includes a reading unit which reads identification information of the CR cassette; and
when the console receives from the bucky device the identification information of the CR cassette read with the reading unit of the bucky device, the console displays the icon corresponding to the image capturing order information including information showing that the portable x-ray radiation image capturing device is loaded into the bucky device in a manner different from the other icons.

7. The x-ray radiation image capturing system of claim 6, wherein,
the console starts the x-ray radiation source to a state where x-ray radiation can be emitted based on the image capturing order information corresponding to the icon displayed in a manner different from the other icons on the display unit and the identification information of the CR cassette; and
after image capturing, when the image data read from the CR cassette with the image reading device is transmitted, a preview image is created based on the image data, and the console displays the created preview image in a position where the icon displayed in a manner different from the other icons is displayed on the display unit.

8. The x-ray radiation image capturing system of claim 1, further comprising,
a plurality of the portable x-ray radiation image capturing devices,
wherein each portable x-ray radiation image capturing device includes a selection unit which notifies to the console a selection signal that the portable x-ray radiation image capturing device is selected when operated; and
when the console receives the selection signal from one of the portable radiation image capturing devices, the console displays the icon corresponding to the image capturing order information including information showing that the portable x-ray radiation image capturing device is not loaded into the bucky device in a manner different from the other icons.

9. The x-ray radiation image capturing system of claim 1, further comprising
a plurality of portable x-ray radiation image capturing devices,
wherein the console manages which portable x-ray radiation image capturing device among the plurality of portable x-ray radiation image capturing devices is in a state where image capturing is possible;
when the portable radiation image capturing device where image capturing is possible is loaded into the bucky device, regardless of the predetermined sequence, the console displays the icon corresponding of the image capturing order information including information showing that the portable x-ray radiation image capturing device is loaded into the bucky device in a manner different from the other icons; and
when the portable x-ray radiation image capturing device in a state where image capturing is possible is not loaded into the bucky device, regardless of the predetermined sequence, the icon corresponding to the image capturing order information including information showing that the portable x-ray radiation image capturing device is not loaded into the bucky device is displayed in a manner different from the other icons.

10. The x-ray radiation image capturing system of claim 9, wherein,
the console obtains from the x-ray radiation source and manages at least one piece of information among a present starting state of the x-ray radiation source and a present emission direction of the x-ray radiation source; and
when there are a plurality of portable x-ray radiation image capturing devices in a state where image capturing is possible, based on at least one piece of information among information of a present starting state of the x-ray radiation source and information of a present emission direction of the x-ray radiation source, the image capturing order information with which image capturing is performed is determined, and when there are a plurality of pieces of image capturing order information with which image capturing is performed, the console displays the plurality of icons corresponding to the plurality of pieces of image capturing order information in a manner different from the other icons and notifies that one icon can be selected from the plurality of icons.

11. The x-ray radiation image capturing system of claim 1, wherein,
the console starts the x-ray radiation source to a state where x-ray radiation can be emitted based on the image capturing order information corresponding to the icon displayed in a manner different from the other icons on the display unit; and
after image capturing, when the read image data, or the thinned out data created based on the image data is transmitted from the portable x-ray radiation image capturing device, a preview image is created based on the image data or the thinned out data and the console displays the created preview image in a position where the icon displayed in a manner different from the other icons is displayed on the display unit.

12. The x-ray radiation image capturing system of claim 11, wherein, when the final x-ray radiation image is generated based on the image data, the console displays the x-ray radiation image in the position where the preview image is displayed on the display unit.

13. The x-ray radiation image capturing system of claim 11, wherein, when the preview image or the x-ray radiation image is displayed on the display unit, the console controls so that the icon displayed in the position on the display unit where the preview image or the x-ray radiation image is displayed cannot be selected.

* * * * *